(12) United States Patent
Sugita et al.

(10) Patent No.: US 8,204,300 B2
(45) Date of Patent: Jun. 19, 2012

(54) IMAGE FORMING METHOD AND OPTICAL COHERENCE TOMOGRAPH APPARATUS USING OPTICAL COHERENCE TOMOGRAPHY

(75) Inventors: Mitsuro Sugita, Tokyo (JP); Koji Nozato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 893 days.

(21) Appl. No.: 12/296,400

(22) PCT Filed: Apr. 3, 2008

(86) PCT No.: PCT/JP2008/057048
§ 371 (c)(1),
(2), (4) Date: Oct. 7, 2008

(87) PCT Pub. No.: WO2008/139799
PCT Pub. Date: Nov. 20, 2008

(65) Prior Publication Data
US 2010/0166293 A1 Jul. 1, 2010

(30) Foreign Application Priority Data

May 2, 2007 (JP) ................................. 2007-121745
Mar. 14, 2008 (JP) ................................. 2008-066055

(51) Int. Cl.
*G06K 9/00* (2006.01)
*G01B 9/023* (2006.01)
(52) U.S. Cl. ........................................ 382/154; 356/479
(58) Field of Classification Search .................. 382/128, 382/130–132, 154; 356/479
See application file for complete search history.

(56) References Cited

U.S. PATENT DOCUMENTS

| 5,321,501 A | 6/1994 | Swanson et al. ............... 356/345 |
| 6,137,585 A | 10/2000 | Hitzenberger et al. ........ 356/484 |
| 6,288,784 B1 | 9/2001 | Hitzenberger et al. ........ 356/485 |
| 6,293,674 B1 | 9/2001 | Huang et al. ................... 351/221 |
| 6,307,634 B2 | 10/2001 | Hitzenberger et al. ........ 356/484 |
| 2003/0199769 A1 | 10/2003 | Podoleanu et al. ............ 600/476 |

(Continued)

FOREIGN PATENT DOCUMENTS
EP  1 775 545  4/2007
(Continued)

OTHER PUBLICATIONS

Christoph K. Hitzenberger et al., "Three-dimensional imaging of the human retina by high-speed optical coherence tomography," Optics Express, vol. 11, No. 21, Oct. 20, 2003, pp. 2753-2761.

(Continued)

*Primary Examiner* — Irakli Kiknadze
(74) *Attorney, Agent, or Firm* — Fitzpatrick, Cella, Harper & Scinto

(57) ABSTRACT

An image forming method uses an optical coherence tomography as to an optical axis direction of plural pieces of image information of an object. First image information of an object is obtained at a first focus with respect to an optical axis direction to then object. A focusing position is changed by dynamic focusing from the first focus to a second focus along the optical axis. The second image information of the object is obtained at the second focus. A third image information, tomography image information of the object and including a tomography image of the first focus or the second focus, is obtained by Fourier domain optical coherence tomography. A tomography image or a three-dimensional image of the object is formed in positional relation, in the optical axis direction, between the first image information and the second image information using the third image information.

19 Claims, 45 Drawing Sheets

U.S. PATENT DOCUMENTS

| | | | |
|---|---|---|---|
| 2006/0077395 A1 | 4/2006 | Chan et al. | 356/497 |
| 2007/0002276 A1 | 1/2007 | Hirohara et al. | 351/206 |
| 2007/0076217 A1 | 4/2007 | Baker et al. | 356/498 |
| 2007/0086011 A1 | 4/2007 | Toida | 356/450 |
| 2007/0236699 A1* | 10/2007 | Chou et al. | 356/489 |

FOREIGN PATENT DOCUMENTS

| | | |
|---|---|---|
| JP | 2002-515593 | 5/2002 |
| JP | 2006-112864 | 4/2006 |
| JP | 2006-158547 | 6/2006 |
| JP | 2007-101250 | 4/2007 |
| WO | 03/105678 | 12/2003 |
| WO | 2006/077107 | 7/2006 |
| WO | 2007/039267 | 4/2007 |

OTHER PUBLICATIONS

M. Pircher et al., "Dynamic focus in optical coherence tomography for retinal imaging," Journal of Biomedical Optics, vol. 11, No. 5, Sep./Oct. 2006, pp. 054013-1-054013-6.

Handbook of Optical Coherence Tomography, 2006, Fig. 2 on p. 145, Fig. 3 on p. 149, and Fig. 1 on p. 338.

International Search Report and Written Opinion from counterpart Int'l Appl. No. PCT/JP2008/057048, Mar. 4, 2008.

Mechanical Translation of JP 2006-158547, Jun. 22, 2006.

* cited by examiner

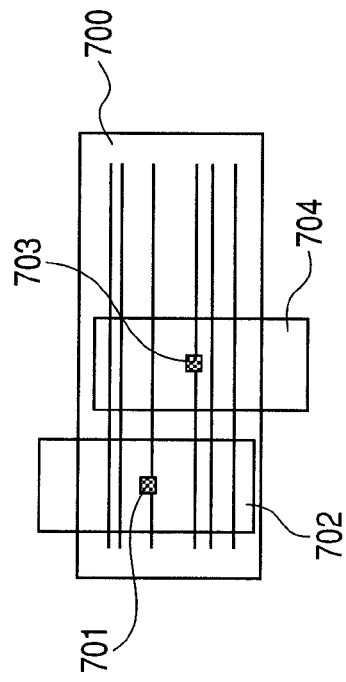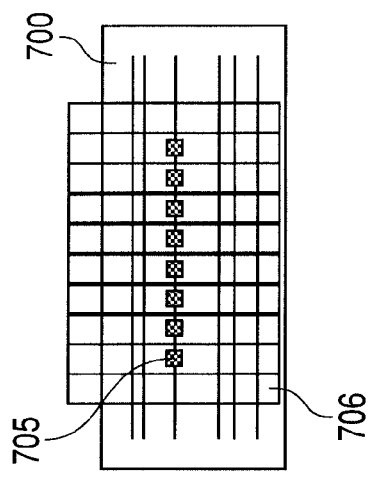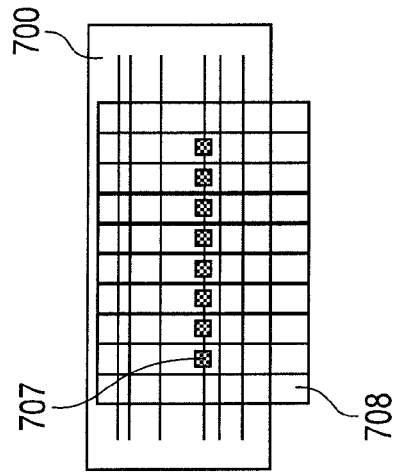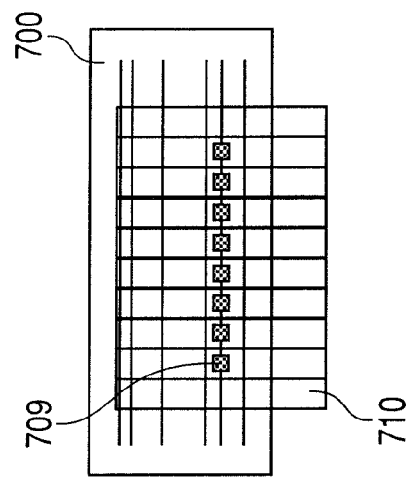

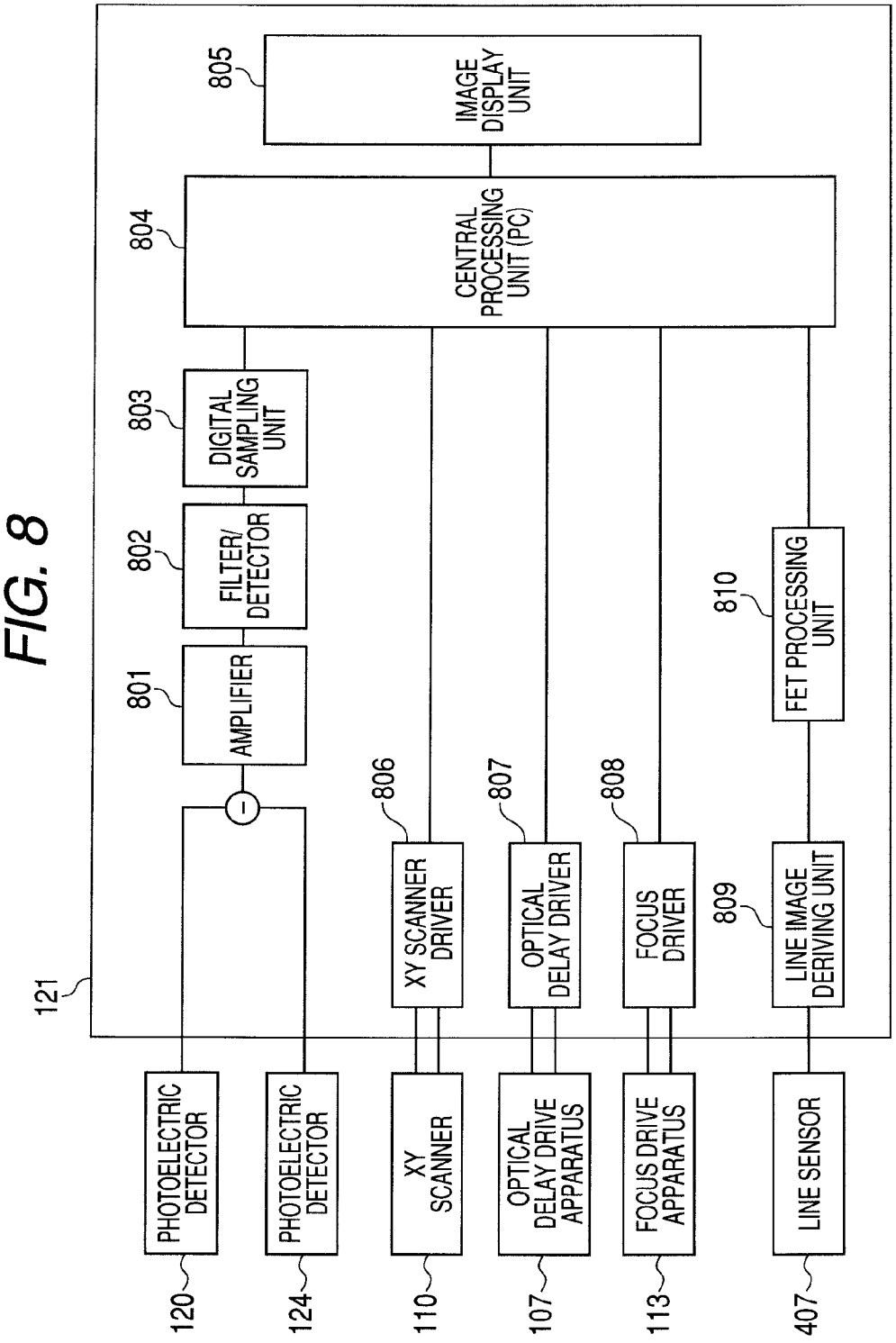

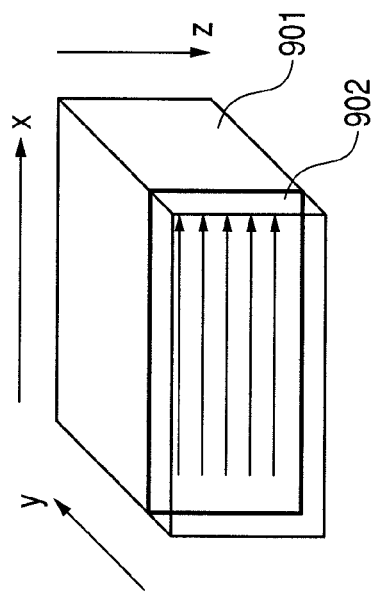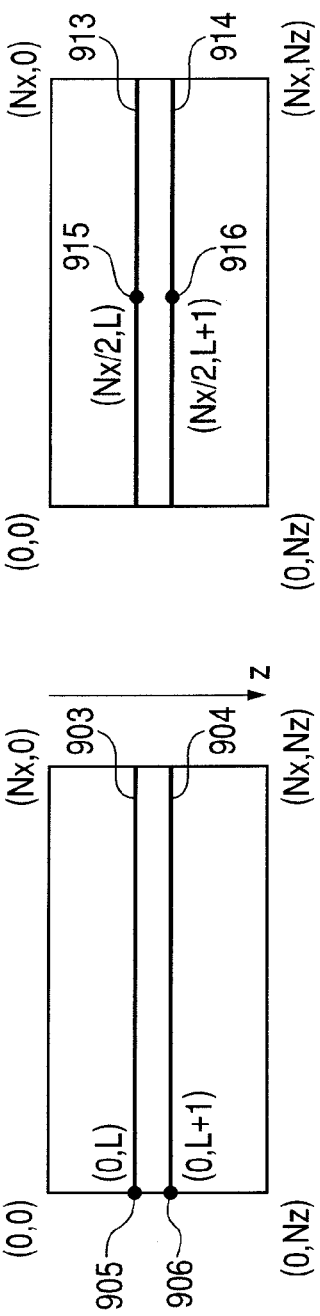

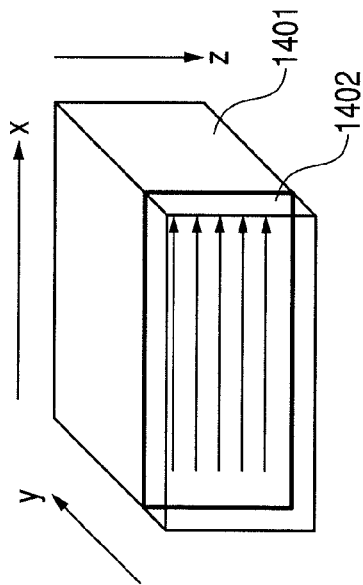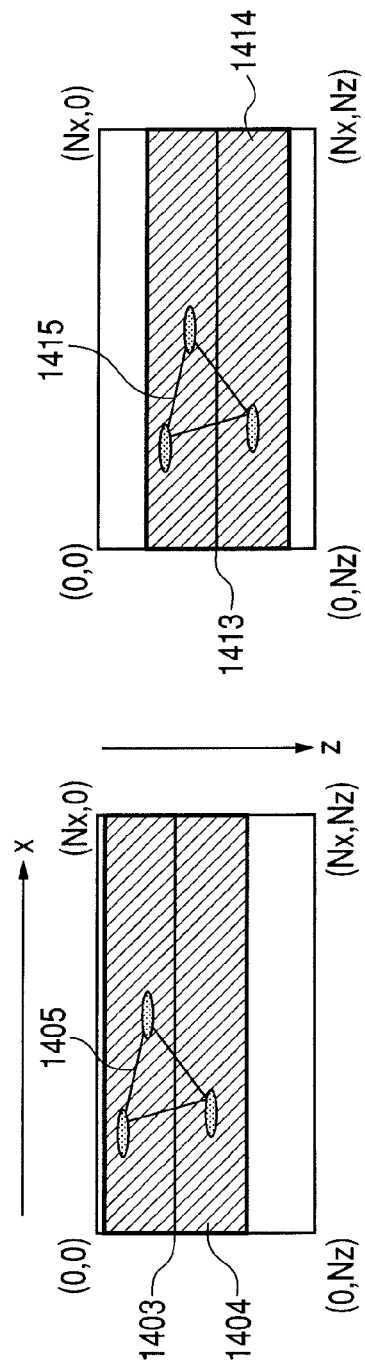

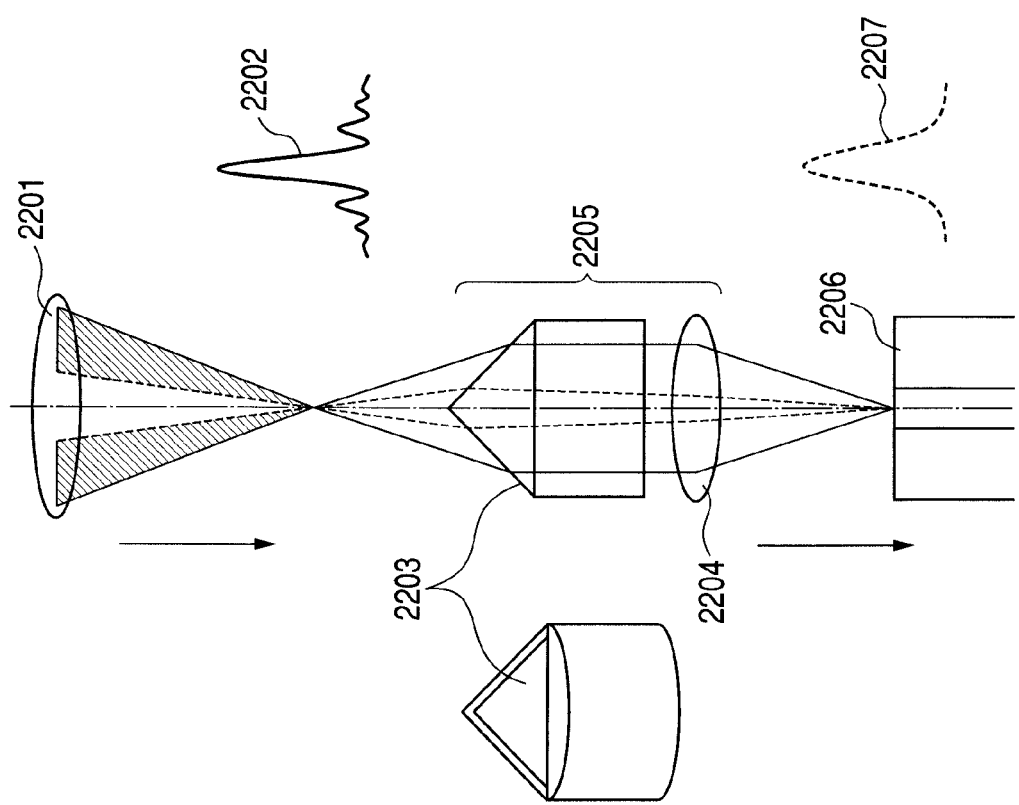
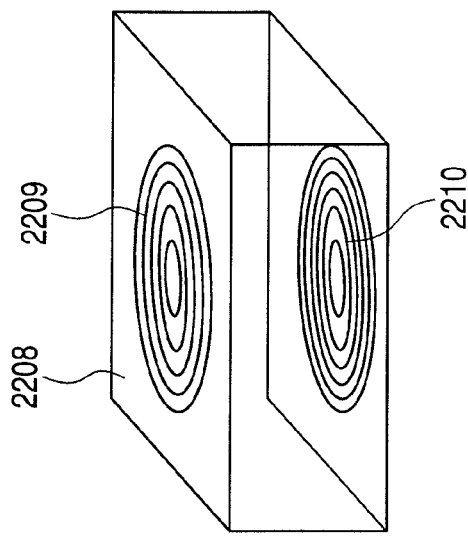

FIG. 25A
FIG. 25B
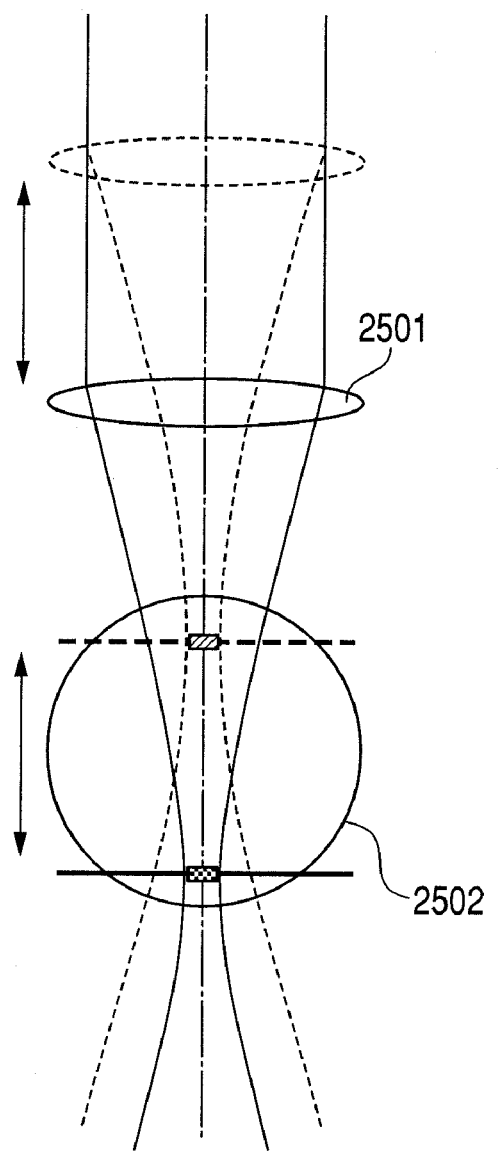
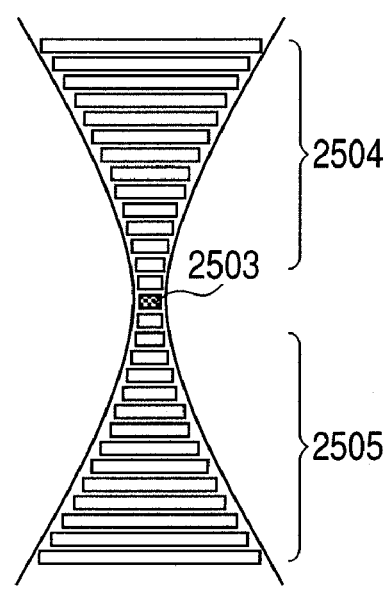

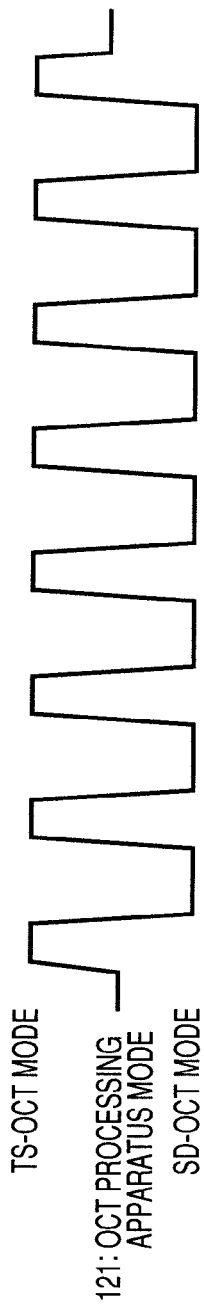
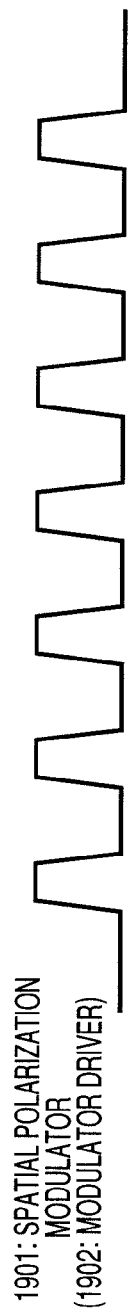
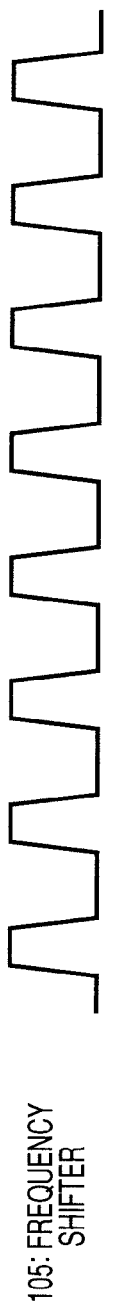
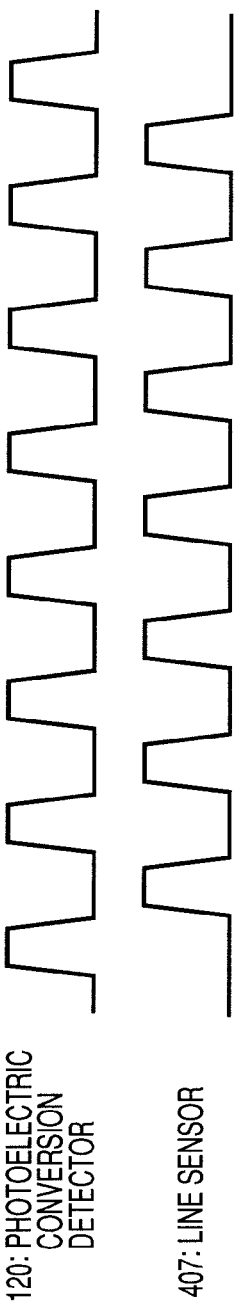
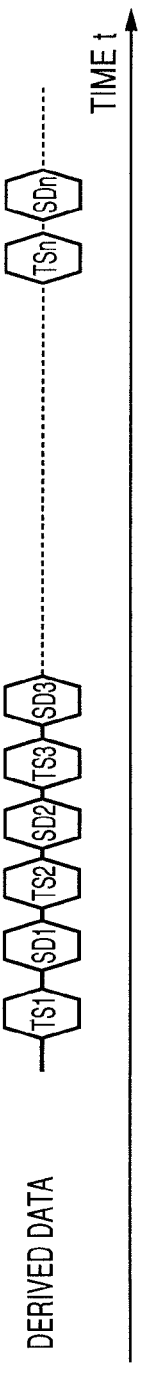
FIG. 42A  121: OCT PROCESSING APPARATUS MODE
FIG. 42B  1901: SPATIAL POLARIZATION MODULATOR (1902: MODULATOR DRIVER)
FIG. 42C  105: FREQUENCY SHIFTER
FIG. 42D  120: PHOTOELECTRIC CONVERSION DETECTOR
FIG. 42E  407: LINE SENSOR
FIG. 42F  DERIVED DATA

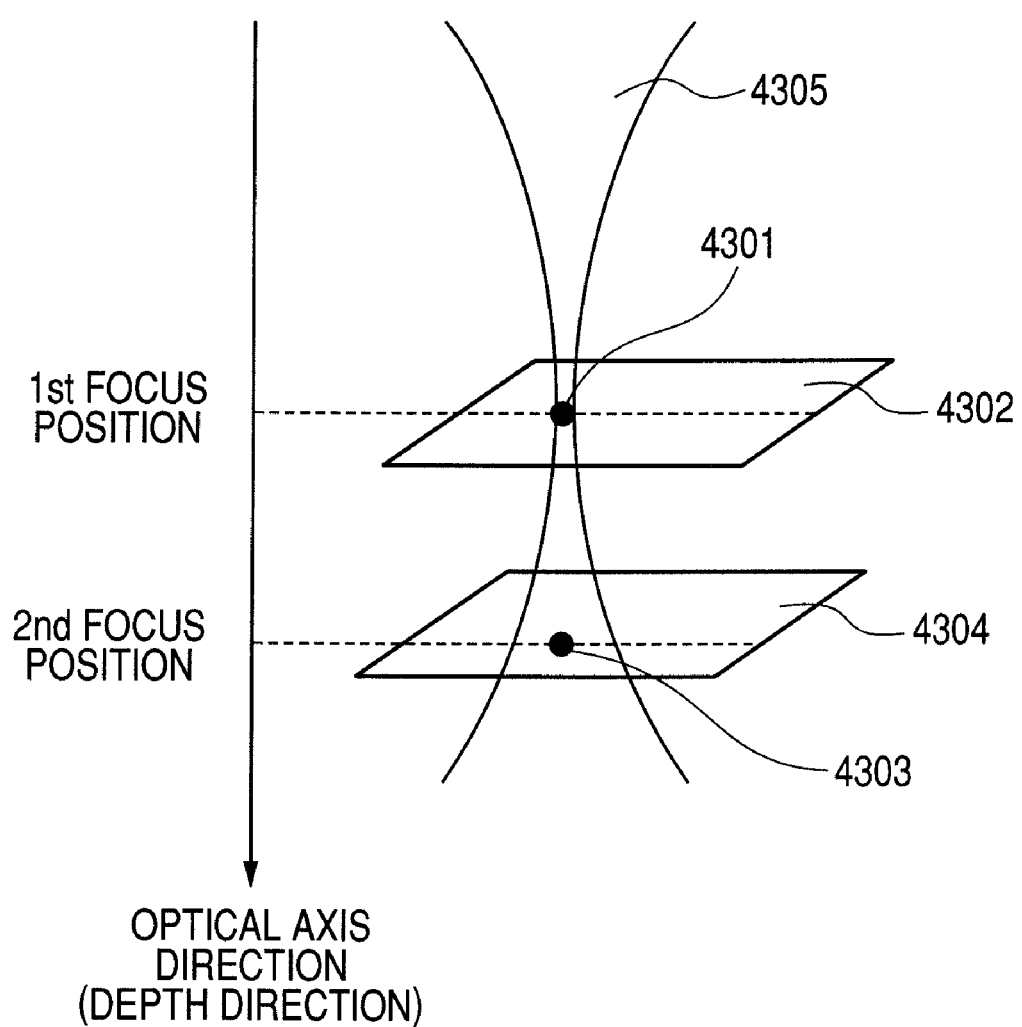

though the A-scan by causing the light beam scanning optical system 3204 to scan the inspection object 3205 with the signal light incident on the inspection object in one direction (for example, x-direction) in a plane of the object.
IMAGE FORMING METHOD AND OPTICAL COHERENCE TOMOGRAPH APPARATUS USING OPTICAL COHERENCE TOMOGRAPHY

TECHNICAL FIELD

The present invention relates to an image forming method and an optical coherence tomograph apparatus which use an optical coherence tomography.

BACKGROUND ART

Recently, imaging apparatuses using low coherence interferometry have been put in practical use. This is called an OCT (Optical Coherence Tomography or Optical Coherence Tomographic method).

In an opthalmologic field, the OCT is used in order to obtain a tomography image of a fundus of the eye or its vicinity. In addition to the opthalmologic field, the OCT is used in an attempt to observe a tomography image of a skin, or to capture a wall surface tomography image of a digestive organ, a circulatory organ, and the like by incorporating the OCT in an endoscope or a catheter.

As a type of the OCT, a method called TD-OCT (Time Domain OCT: a TIME DOMAIN method) is disclosed in U.S. Pat. No. 5,321,501. This method will be described briefly with reference to FIG. 32.

Here, FIG. 32 is a schematic diagram illustrating a TD-OCT.

Light radiated by a radiation unit 3201 is divided into reference light and signal light by a division unit 3202. The reference light is reflected by a movable reference mirror 3203. As illustrated in the figure, the movable reference mirror 3203 is moved in a one-dimensional direction mechanically to define a measured position inside an inspection object 3205 in an optical axis direction of signal light incident on the inspection object 3205.

Through a light beam scanning optical system 3204, the signal light impinges on and is reflected by the inspection object 3205. The light beam scanning optical system 3204 uses the signal light incident on the inspection objects 3205 to scan in a predetermined direction. Reflected light from the movable reference mirror 3203 and that from the inspection object 3205 interfere with each other, and the interference light is detected by a detection unit 3207 to determine information with respect to the inspection object 3205.

TD-OCT is a method of constructing image data based on strength data of the successively obtained interference light by performing an A-scan (axis-directional scanning of incident light into an inspection object, or depth-directional scanning in the inspection object) by the movable reference mirror 3203.

One-dimensional data can be obtained continuously through the A-scan by causing the light beam scanning optical system 3204 to scan the inspection object 3205 with the signal light incident on the inspection object in one direction (for example, x-direction) in a plane of the object.

Then, a two-dimensional tomography image can be obtained using images obtained continuously. In addition, a three-dimensional image can be obtained by using the above-mentioned signal light to scan in two directions (e.g., an x-direction and a y-direction) within the above-mentioned plane.

Here, although it is necessary to move the movable reference mirror 3203 at high speed in order to increase measuring speed by the TD-OCT, there is a mechanical limit in acceleration of the movable reference mirror 3203.

In addition, as another type of OCT, a method called an SD-OCT (Spectral Domain OCT: Spectral domain method) is disclosed in "Handbook of Optical Coherence Tomography" (2006) (FIGS. 2 and 3 in pages 145 and 149, and FIG. 1 in page 338). This method will be described briefly with reference to FIG. 33.

Here, FIG. 33 is a schematic diagram illustrating the SD-OCT. In FIG. 33, constructions different from FIG. 32 are a point that a movable reference mirror is a fixed reference mirror 3308, a point of using a spectroscopes 3309, such as a diffraction grating, and a point that a detection unit is a spectral detection unit 3310, such as a line sensor. Reference numeral 3305 denotes an inspection object, reference numeral 3306 does a measurement region, reference numeral 3304 does a scanning optical system, reference numeral 3302 does a light dividing unit, reference numeral 3308 does a reflection unit, and reference numeral 3301 does a light source.

SD-OCT is a method of acquiring image data temporally in a lump by detecting a spectrum, dispersed by the spectroscope 3309, by the spectral detection unit 3310, and performing Fourier transformation of the coherent light intensity information with respect to a wavelength axis into information with respect to a tomographic position axis. Since this SD-OCT can obtain image data in a depth direction inside the inspection object 3305 in a lump, it is possible to increase measuring speed in comparison with the TD-OCT which performs serial scanning temporally in the depth direction.

Here, the SD-OCT (Spectral Domain method) is one kind of an FD-OCT (Fourier domain optical coherence tomography), and, besides this, there is an SS-OCT (Source Swept-OCT).

SUMMARY OF THE INVENTION

It is pointed out typically that there is a difficulty in increasing a lateral resolution of a tomography image in an SD-OCT (a lateral resolution is a resolution with respect to an image in an in-plane direction in each depth position against a depth direction of an inspection object being called a longitudinal resolution).

The present inventors reached the following idea in view of a circumstance that there is a difficulty in mechanically moving the reference mirror 3203 at high speed whether a tomography image is to be formed by the TD-OCT or the SD-OCT.

Thus, first, with respect to a depth direction (a z-direction) of an inspection object, a one-dimensional image (an x-directional or a y-directional image) or a two-dimensional image (xy plane) at a position including a specific focus is obtained. Then, with respect to the above-mentioned depth direction, a tomography image and three-dimensional image are formed by sequentially acquiring a one-dimensional image and a two-dimensional image including each focusing position while changing the above-mentioned position of a focus, and stacking those images along the depth direction.

Nevertheless, when acquiring a one-dimensional image or a two-dimensional image while changing a focusing position, an inspection object is scanned in a one-dimensional direction (or a two-dimensional direction) with respect to a depth direction within the inspection object at a specific focusing position, followed by the next focusing position, and the scanning is repeated. A problem found was that the distance in the depth direction is likely to have a large shift between data obtained at one focusing position and data obtained at another focusing position due to movement of the inspection object as well as disturbance or vibration on the measuring system.

For example, in tomography imaging of an eyeground, a change in a layer thickness of a nerve or a cell is used as a diagnostic index of an illness, and the like. For this reason, we have realized that it is necessary to associate pieces of the positional information in the respective image information of the inspection object with each other with respect to the depth directions. At this time, it is possible to use tomography information in the depth direction collectively obtained using the FD-OCT (Fourier domain optical coherence tomography).

As described above, the present invention aims at providing an image forming method and an optical coherence tomograph apparatus which use a new optical coherence tomographic method which can associate positional relation, with respect to the depth direction (optical axis direction which is a direction where light is incident into an inspection object), between the respective image information of the inspection object.

An image forming method using an optical coherence tomography which relates to a first present invention includes:

a first image information obtaining step of obtaining first image information of an inspection object at a first focusing position with respect to an optical axis direction which is a direction in which light is directed onto the inspection object;

a step of changing a focusing position by dynamic focusing from the first focusing position to a position of a second focus which is different from the first focus with respect to the optical axis direction;

a second image information obtaining step of obtaining second image information of the inspection object at the second focusing position; and a step of obtaining third image information, which is tomography image information of the inspection object and includes a tomography image of the inspection object at least one focusing position of the first focusing position or the second focusing position, by Fourier domain optical coherence tomography, and is characterized by associating positional relation, with respect to the optical axis direction, between the first image information and the second image information using the third image information, and forming a tomography image or a three-dimensional image of the inspection object.

An image forming method using an optical coherence tomography which relates to a second present invention includes:

a first image information obtaining step of obtaining first image information, which is a C-scan image of an inspection object at a first focusing position, with respect to an optical axis direction which is a direction in which light is directed onto the inspection object by a time domain optical coherence tomography;

a step of changing a focusing position by dynamic focusing from the first focusing position to a position of a second focus which is different from the first focus with respect to the optical axis direction;

a second image information obtaining step of obtaining second image information, which is a C-scan image of the inspection object, at the second focusing position by the time domain optical coherence tomography; and a step of obtaining third image information, which is tomography image information of the inspection object and includes a tomography image of the inspection object at a position of at least one focus of the first focus or the second focus, by a spectral domain optical coherence tomography, and is characterized by associating positional relation, with respect to the optical axis direction, between the first image information and the second image information using the third image information, and forming a tomography image or a three-dimensional image of the inspection object.

An image forming method using an optical coherence tomography which relates to a third present invention includes:

a first image information obtaining step of obtaining first image information of an inspection object at a first focusing position with respect to an optical axis direction which is a direction in which light is directed onto the inspection object by Fourier domain optical coherence tomography;

a step of changing a focusing position by dynamic focusing from the first focusing position to a position of a second focus which is different from the first focus with respect to the optical axis direction;

a second image information obtaining step of obtaining second image information of the inspection object at the second focusing position by the Fourier domain optical coherence tomography; and is characterized by associating positional relation, with respect to the optical axis direction, between the first image information and the second image information using tomography information of the inspection object which is obtained by at least one step of the first or second image information obtaining step, and forming a tomography image or a three-dimensional image of the inspection object.

An image forming method using an optical coherence tomography which relates to a fourth present invention includes:

a first image information obtaining step of obtaining first image information of an inspection object at a first focusing position with respect to an optical axis direction which is a direction in which light is directed onto the inspection object;

a step of changing a focusing position by dynamic focusing from the first focusing position to a position of a second focus which is different from the first focus with respect to the optical axis direction;

a second image information obtaining step of obtaining second image information of the inspection object at the second focusing position; and a step of obtaining tomography image information with respect to the optical axis direction of the inspection object by the Fourier domain optical coherence tomography, and is characterized by associating positional relation, with respect to the optical axis direction, between the first image information and the second image information using the tomography image information, and forming a tomography image or a three-dimensional image of the inspection object.

In addition, an image forming method using an optical coherence tomography which relates to the another present invention includes:

a first image information obtaining step of obtaining a one-dimensional or two-dimensional image of an inspection object at a position including a first focus with respect to an optical axis direction which is a direction in which light is directed onto the inspection object;

a second image information obtaining step of obtaining a one-dimensional or two-dimensional image of the inspection object at a position including a second focus different from the first focus with respect to the optical axis direction; and a step of obtaining third image information, which is tomography image information of the inspection object and includes a tomography image of the inspection object at least one focusing position of the first focus or the second focus, by Fourier domain optical coherence tomography, and is characterized by correcting positional relation between both of image information, obtained by the first and the second image information obtaining steps respectively, using the third image information, and forming a tomography image or a three-dimensional image of the inspection object.

In addition, an image forming method using an optical coherence tomography which relates to another present invention includes:

a first image information obtaining step of obtaining a C-scan image of an inspection object at a position including a first focus, with respect to an optical axis direction which is a direction in which light is directed onto the inspection object by a time domain optical coherence tomography;

a second image information obtaining step of obtaining a C-scan image of the inspection object at a position including a second focus different from the first focus with respect to the optical axis direction by the time domain optical coherence tomography;

a step of obtaining third image information, which is tomography image information of the inspection object and includes a tomography image of the inspection object at a position of at least one focus of the first focus or the second focus, by a spectral domain optical coherence tomography, and is characterized by correcting positional relation between both of image information, obtained by the first and the second image information obtaining steps respectively, using the third image information, and forming a tomography image or a three-dimensional image of the inspection object.

In addition, an image forming method using an optical coherence tomography which relates to another present invention includes:

a first image information obtaining step of obtaining a one-dimensional or two-dimensional image of an inspection object at a position, including a first focus with respect to an optical axis direction which is a direction in which light is directed onto the inspection object, by a spectral domain optical coherence tomography;

a second image information obtaining step of obtaining a one-dimensional or two-dimensional image of the inspection object at a position, including a second focus different from the first focus with respect to the optical axis direction, by a spectral domain optical coherence tomography, and is characterized by correcting positional relation, with respect to the optical axis direction, between both of image information obtained respectively by the first and second image information obtaining steps using tomography information of the inspection object which is obtained by at least one step of the first or second image information obtaining step, and forming a tomography image or a three-dimensional image of the inspection object.

In addition, an image forming method using an optical coherence tomography which relates to another present invention includes:

a first image information obtaining step of obtaining a one-dimensional or two-dimensional image of an inspection object at a position including a first focus with respect to an optical axis direction which is a direction in which light is directed onto the inspection object;

a second image information obtaining step of obtaining a one-dimensional or two-dimensional image of the inspection object at a position including a second focus different from the first focus with respect to the optical axis direction; and a step of obtaining tomography image information with respect to the optical axis direction of the inspection object by the Fourier domain optical coherence tomography, and is characterized by correcting positional relation between both of image information, obtained by the first and the second image information obtaining steps respectively, using the tomography image information, and forming a tomography image or a three-dimensional image of the inspection object.

In addition, an image forming method using an optical coherence tomography which relates to another present invention is characterized by obtaining by a spectral domain optical coherence tomography a one-dimensional or two-dimensional image of an inspection object in regard to an optical axis direction, which is a direction in which light is directed onto the inspection object, respectively while changing a focusing position with respect to the optical axis direction, and forming a tomography image or a three-dimensional image of the inspection object.

In addition, an optical coherence tomograph apparatus which relates to another present invention is an apparatus for performing image formation in the above-described present invention, and is characterized by having a light source for causing light to impinge on an inspection object, a light dividing unit for dividing the light from the light source into signal light and reference light, and a detection unit for dispersing and detecting coherent light of the reference light and signal light.

According to the present invention described above, it is possible to associate positional relations with each other, with respect to a depth direction (an optical axis direction which is a direction in which light is directed onto an inspection object), in the respective image information of an inspection object.

Further features of the present invention will become apparent from the following description of exemplary embodiments with reference to the attached drawings.

BRIEF DESCRIPTION OF THE DRAWINGS

FIGS. 7A, 7B, 7C and 7D are schematic diagrams illustrating tomography images which are obtained and processed by the second example of the present invention.

FIG. 8 is a schematic diagram illustrating functional blocks of an OCT processing unit in the second example of the present invention.

FIGS. 9A, 9B and 9C are schematic diagrams illustrating alignment positions between line images in the second example of the present invention.

FIGS. 14A, 14B and 14C are schematic diagrams illustrating alignment locations between two-dimensional SD-OCT images in the second example of the present invention.

FIGS. 22A and 22B are schematic diagrams illustrating an example of optical mode conversion in the seventh example of the present invention.

FIGS. 25A and 25B are schematic diagrams illustrating SD-OCT pixel construction in the ninth example of the present invention.

FIGS. 42A, 42B, 42C, 42D, 42E and 42F are examples of timing charts in the fifth example of the present invention.

FIG. 43 is a schematic diagram for describing an example of a method of correcting positional relation between both tomography images with respect to a depth direction by an optical coherence tomography which relates to the present invention.

BEST MODE FOR CARRYING OUT THE INVENTION

Preferred embodiments of the present invention will now be described in detail in accordance with the accompanying drawings.

First Embodiment

An image forming method using an optical coherence tomography (in other words, an optical coherent tomographic method) which relates to a first embodiment has at least the following steps 1 to 4.

1. A first image information obtaining step of obtaining first image information (a one-dimensional, two-dimensional, or three-dimensional image) of an inspection object at a position including a first focus with respect to an optical axis direction which is a direction in which light is directed onto the inspection object 2. A second image information obtaining step of obtaining second image information (a one-dimensional, two-dimensional, or three-dimensional image) of the inspection object at a position including a second focus different from the first focus with respect to the optical axis direction 3. A step of obtaining third image information, which is tomography image information of the inspection object and includes a tomography image of the inspection object at least at one focusing position of the first focus or the second focus, by Fourier domain optical coherence tomography 4. A step of correcting positional relation between both of image information, obtained by the first and second image information obtaining steps respectively, using the third image information, and forming a tomography image or a three-dimensional image of the inspection object.

Figure 1:
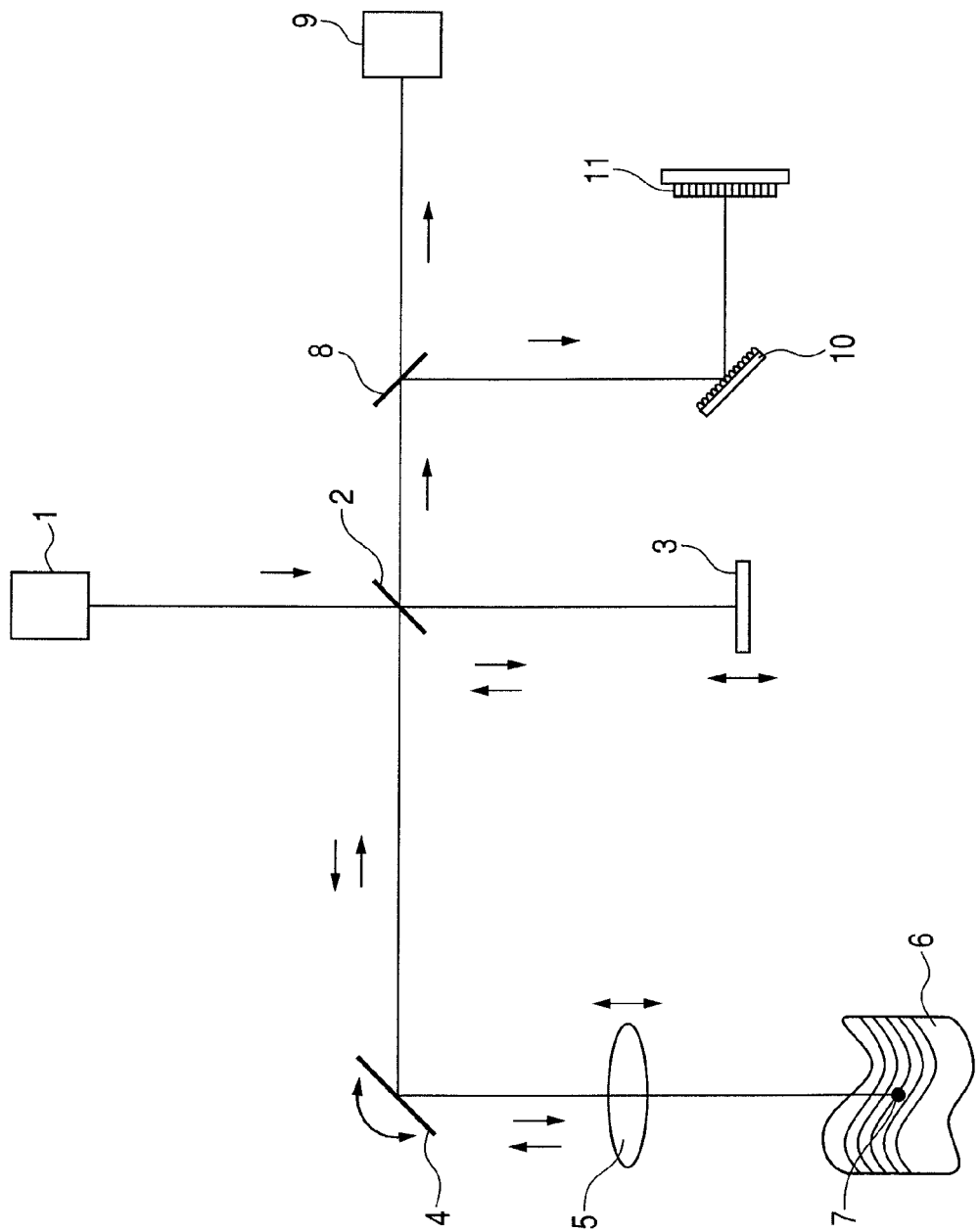
FIG. 1 is a schematic diagram for describing an optical coherence tomography which relates to the present invention.

The above-mentioned steps will be described with reference to FIG. 1. In addition, the step order of the above-mentioned steps 1, 2, and 3 is not limited particularly, however, it may be, for example, an order of 1, 2, and 3, an order of 1, 3, and 2, or an order of 3, 2, and 1.

In the diagram, although a wavelength of a light source (e.g., a low coherent light source, SLD, etc.) 1 is not limited particularly, it is in a range of 400 nm to 2 micrometers. Then, a wavelength interval for achieving the OCT may be, for example, 1 pm or more, suitably 10 pm or more, and further suitably 30 pm or more. Ultrashort pulsed laser, such as a titanium sapphire laser, can also be used for a light source.

A light dividing unit 2 divides input light from the light source 1 into signal light (light incident on a detected object), and reference light (light which goes to a reflector plate 3) here. A unit 4 is for scanning the signal light in a one-dimensional direction or a two-dimensional direction. Reference numeral 5 denotes a lens, reference numeral 6 denotes an inspection object, and reference numeral 7 denotes a predetermined focusing position where focusing is performed with the lens 5, and its vicinity. A unit 8 is for dividing coherent light of the signal light and reference light, a spectroscope 10 is for dividing input light into every wavelength, and a sensor array 11 is for performing detection every wavelength. A detection unit 9 is for detecting coherent light.

Here, the first focus in step 1 has a finite width. In addition, a size of a focus is not limited particularly. A second focus and a third focus which are mentioned later are the same.

In addition, the one-dimensional image means an image in one direction (it is an x-direction or a y-direction, and is a direction orthogonal to a depth direction) in a plane of an inspection object at a certain focusing position, for example. Furthermore, the two-dimensional image means an image in two directions (it is the x-direction or y-direction, and is the direction orthogonal to the depth direction) in a plane of the inspection object at a certain focusing position, for example, and it may be called a C-scan image. In addition, the same thing can be said also for step 2. An OCT used to obtain a C-scan image is called a TS-OCT, and this will be mentioned later.

In addition, although it is desirable that a one-dimensional or two-dimensional image of an inspection object at a position including a first focus and a one-dimensional or two-dimensional image at a position including a second focus are substantially parallel, it is not always necessary that they are parallel. For example, it is also sufficient to be in such relationship between images that both images intersect.

The above-mentioned third image information is obtained by a spectral domain optical coherence tomography (SD-OCT) which is one in the above-described Fourier domain optical coherence tomography. In addition, similarly, an SS-OCT (Source Swept-OCT) which is one in the Fourier domain optical coherence tomography can be also used. In particular, since a tomography-directional image by the Fourier domain optical coherence tomography has a high longitudinal resolution, the present invention corrects depth-directional positional relation between the above-mentioned first image information and second image information with respect to an inspection object using it. The correction of positional relation in step 4 means, for example, correction of both images obtained by the first and second image information obtaining steps with respect to a depth direction of an inspection object or correction with respect to the above-mentioned optical axis direction.

The above-mentioned correction will be described below.

(Types of Correction Control)

There are two types of correction control; one of which is called a closed loop and the other of which is called an open loop, depending on whether a control loop is closed or opened.

The closed loop is a method of correcting positional relation between both image information with respect to a depth direction while obtaining the image information, and may be called tracking. In addition, the open loop is a method of correcting positional relation between both image information with respect to a depth direction after obtaining the image information.

Here, the above-mentioned two controls are applicable to all three detection methods described below.

In addition, the present invention is not limited to these corrections.

Next, correction detection methods will be described. In addition, although the example of alignment (example using a correlation function, etc.) described in detail in the second example is suitable as a correction detection method, the detection methods of the present invention are not limited to these.

(First Correction Detection Method)

A first correction detection method will be described with reference to FIG. 43.

The above-mentioned third image information is tomography image information 4305 along the above-mentioned optical axis direction at a position of the above-mentioned first focus 4301. Here, in the present invention, it can be also said that the image information of the inspection object at a focusing position is image information of the inspection object at a position including the focus. In addition, the focus in the present invention is a point at which focusing is performed by dynamic focusing, and it is not limited particularly for a focal size.

The above-mentioned third image information includes tomography information of the above-mentioned inspection object at a position of the above-mentioned second focus 4303.

Furthermore, positional relation with respect to the above-mentioned optical axis direction between the above-mentioned first image information 4302 and the above-mentioned second image information 4304 is corrected using the above-mentioned third image information.

Here, when the above-mentioned second image information 4304 is obtained, a depth-directional positional offset of the above-mentioned second image information 4304 can be detected by using the above-mentioned tomography image information 4305 already obtained. A tomography image or three dimensional image of the above-mentioned inspection object can be formed while correcting (tracking) this positional offset. Of course, it is mentioned above that the tomography image or three dimensional image of the above-mentioned inspection object could be formed while correcting a positional offset, also in the following detection methods.

(Second Correction Detection Method)

Figure 44:
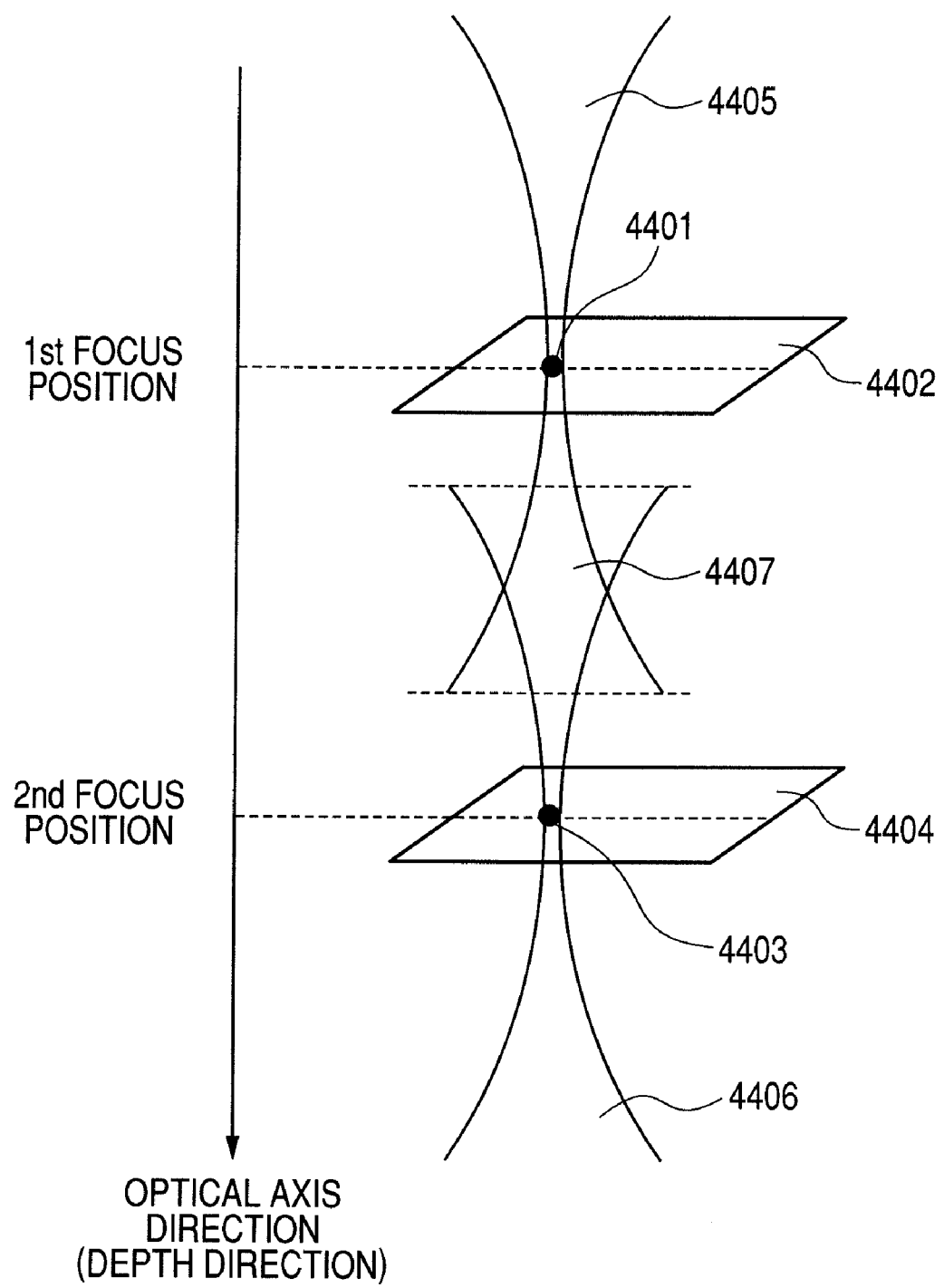
FIG. 44 is a schematic diagram for describing an example of a method of correcting positional relation between both tomography images with respect to a depth direction by an optical coherence tomography which relates to the present invention.

A second correction detection method will be described with reference to FIG. 44.

The above-mentioned third image information is obtained by the Fourier domain optical coherence tomography, and includes the first tomography image 4405 along the above-mentioned optical axis direction at a position of the above-mentioned first focus 4401 of the above-mentioned inspection object.

In addition, the above-mentioned third image information is obtained by the Fourier domain optical coherence tomography, and includes the second tomography image 4406 along the above-mentioned optical axis direction at a position of the above-mentioned second focus 4403 of the above-mentioned inspection object.

Next, the above-mentioned correction is performed using information in a duplicating region 4407 of the above-mentioned first tomography image 4405 and the above-mentioned second tomography image 4406. That is, the positional relation with respect to the optical axis direction between the above-mentioned first image information 4402 and the above-mentioned second image information 4404 which are related to the above-mentioned first and second tomography images 4405 and 4406 respectively is corrected.

Another second correction is as follows.

That is, the tomography images 4405 and 4406 of the inspection object in both positions of the above-mentioned first focus 4401 and the above-mentioned second focus 4403 are obtained by the Fourier domain optical coherence tomography as the above-mentioned third image information respectively. Then, the above-mentioned correction is performed using information on the region 4407 in which respective tomography images duplicate.

(Third Correction Detection Method)

Figure 45:
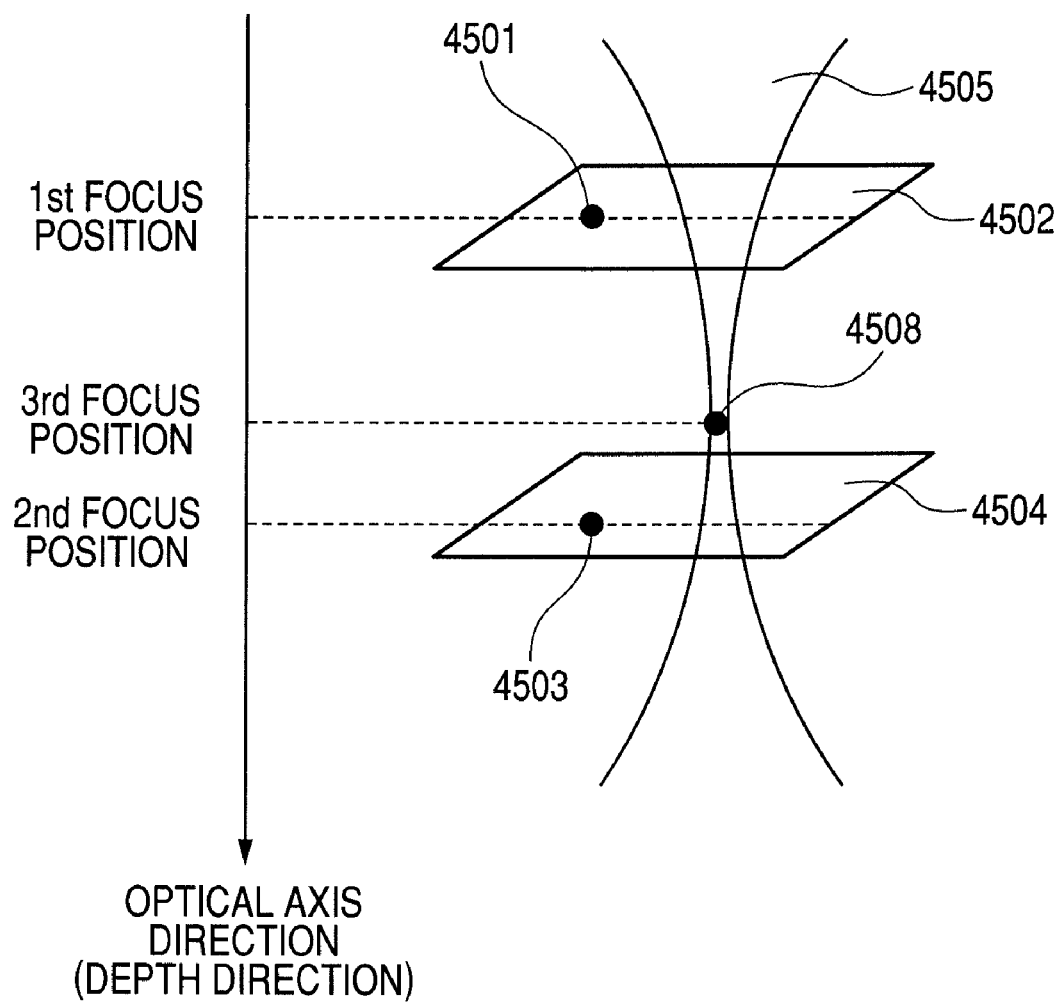
FIG. 45 is a schematic diagram for describing an example of a method of correcting positional relation between both tomography images with respect to a depth direction by an optical coherence tomography which relates to the present invention.

A third correction detection method will be described with reference to FIG. 45.

Firstly, what is obtained is first image information (a one-dimensional, two-dimensional, or three-dimensional image) 4502 of an inspection object at a position of a first focus 4501 with respect to an optical axis direction which is a direction in which light is directed onto the inspection object.

Next, a focusing position is changed by dynamic focusing from the first focusing position 4501 to a position of a second focus 4503 which is different from the first focus 4501 with respect to the optical axis direction.

In addition, what is obtained is second image information (a one-dimensional, two-dimensional, or three-dimensional image) 4504 of the inspection object at a position of the second focus 4503.

Furthermore, what is obtained is tomography image information 4505 with respect to the optical axis direction of the inspection object by the Fourier domain optical coherence tomography.

Here, the above-mentioned tomography image information 4505 can be obtained at a position of a third focus 4508 which is different from the positions of the above-mentioned first and second focuses 4501 and 4503, with respect to the above-mentioned optical axis direction. At this time, the above-mentioned tomography image information 4505 can be obtained, including the image information of the inspection object at the positions of the first and second focuses 4501 and 4503.

Thereby, the tomography image information 4505 is used to associate positional relations with respect to the optical axis direction with each other between the first image information 4502 and the second image information 4504 to form a tomography image or a three-dimensional image of the inspection object.

(Another Correction)

Here, another correction is as follows.

Thus, the above-mentioned third image information is obtained by the spectral domain optical coherence tomography, and is tomography image information along the above-mentioned optical axis direction including the position of the above-mentioned first focus of the above-mentioned inspection object. Then, the above-mentioned correction can be performed using the tomography image information and the image obtained at the above-mentioned second image information obtaining step.

Here, another correction is as follows.

Thus, the above-mentioned third image information is obtained by the spectral domain optical coherence tomography, and includes at least a part of a first tomography image along the above-mentioned optical axis direction including the position of the above-mentioned first focus of the above-mentioned inspection object.

In addition, the above-mentioned third image information is obtained by the spectral domain optical coherence tomography, and includes at least a part of a second tomography image along the above-mentioned optical axis direction including the position of the above-mentioned second focus of the above-mentioned inspection object.

Here, what can be corrected is positional relation between both image information, which are associated with the first and second tomography images respectively and are obtained at the above-mentioned first and second image information obtaining step, using information in a duplicating region of the above-mentioned first tomography image and the above-mentioned second tomography image.

Furthermore, another correction is as follows.

That is, the tomography images of the inspection object in both positions of the above-mentioned first focus and the above-mentioned second focus are obtained by the Fourier domain optical coherence tomography as the above-mentioned third image information respectively. Then, the above-mentioned correction is performed using information on a region in which respective tomography images duplicate.

In addition, although a specific correction method is described in detail in each embodiment, correction provided according to the present invention is not limited to the method concerned.

(a) First and Second Image Information=TD-OCT

The above-mentioned first and second image information obtaining steps can be made into steps of obtaining a one-dimensional or two-dimensional image of the above-mentioned inspection object by the time domain optical coherence tomography.

(b) Correction of TS-OCT with SD-OCT Image

Specifically, an image forming method using the optical coherence tomography which relates to this first embodiment can be performed at the following steps.

1. A first image information obtaining step of obtaining a C-scan image of an inspection object at a position including a first focus, with respect to an optical axis direction which is a direction in which light is directed onto the inspection object by a time domain optical coherence tomography 2. A second image information obtaining step of obtaining a C-scan image of the inspection object at a position including a second focus different from the first focus with respect to the optical axis direction by the time domain optical coherence tomography 3. A step of obtaining third image information, which is tomography image information of the inspection object and includes a tomography image of the inspection object at a position of at least one focus of the first focus or the second focus, by a spectral domain optical coherence tomography, and 4. A step of correcting positional relation between both of the image information, obtained by the first and second image information obtaining steps respectively, using the third image information, and forming a tomography image or a three-dimensional image of the inspection object.

(c) Pattern Using Non-Limited Focusing Positions at the Time of SD-OCT

In addition, the invention which relates to this first embodiment can be performed also in the following steps.

1. A first image information obtaining step of obtaining a one-dimensional or two-dimensional image of an inspection object at a position including a first focus with respect to an optical axis direction which is a direction in which light is directed onto the inspection object 2. A second image information obtaining step of obtaining a one-dimensional or two-dimensional image of the inspection object at a position including a second focus different from the first focus with respect to the optical axis direction 3. A step of obtaining tomography image information with respect to the optical axis direction of the inspection object by the Fourier domain optical coherence tomography 4. A step of correcting positional relation between both of the image information, obtained by the first and second image information obtaining steps respectively, using the tomograph image information, and forming a tomography image or a three-dimensional image of the inspection object.

In addition, when correction is performed using SD-OCT as the Fourier domain optical coherence tomography, it is good to take the following points into consideration. In the case of using a frequency shifter, such as an AOM, when obtaining a tomography image by the time domain optical coherence tomography, light intensity input into a spectroscope also deviates relatively by the reference signal from the drive circuit of the frequency shifter. In order to avoid this, using a spectroscope, it is good to use a value obtained by integrating light intensity information obtained in an integral or half-integral multiple of time when obtaining tomography information by the spectral domain optical coherence tomography. Alternatively, it may be made to detect intensity by the spectral domain optical coherence tomography by synchronizing it with the reference signal of the above-mentioned frequency shifter.

Correction is performed by superimposing duplicated regions in tomography images in an optical axis direction at two focusing positions.

(d) Application of DF (Dynamic Focusing)

When obtaining image data through the OCT, high resolution is requested in both an in-plane direction (xy direction) and a depth direction (z-axial direction) of an inspection object.

Here, let a depth resolution of an inspection object be a longitudinal resolution (Rz), and let an in-plane resolution, which is orthogonal to the depth direction of the inspection object, be a lateral resolution (Rxy). The longitudinal resolution is expressed as follows:

$$Rz = kz \times (\lambda^2/\Delta\lambda) \quad (1)$$

and is in inverse proportion to a wavelength interval ($\Delta\lambda$) of a light source. Here, kz is a constant of about 0.4. The lateral resolution is expressed as follows:

$$Rxy = k1 \times (\lambda/NA) \quad (2)$$

and is in inverse proportion to a numerical aperture NA (Numerical Aperture) of a condensing system such as a lens. Here, k1 is a constant of about 0.5. Furthermore, a depth of focus DOF (Depth of Focus) of a condensing system is expressed as follows:

$$DOF = k2 \times (\lambda/NA^2) \quad (3)$$

and is in inverse proportion to the square of an aperture of the condensing system. Here, k2 is a constant of about 0.6.

As shown in the formulas (2) and (3), making the lateral resolution high (a value of Rxy becomes small at this time), and making the depth of focus deep has relationship of optically theoretic trade-off. In an eyeground diagnostic system in which OCT is put in practical use, for example, values of $\lambda = 0.84$ micrometer and NA=0.02 are used, and, when these numerical values are substituted for (formulas 2) and (formula 3), Rxy=20 micrometer and DOF=2 mm hold.

A method called DF (dynamic focusing) is disclosed in U.S. Pat. No. 5,321,501 as a method of obtaining a high lateral resolution while keeping a depth of focus in a depth direction of an inspection object. Here, the DF will be described with reference to FIGS. 34A and 34B.

Figure 34B:
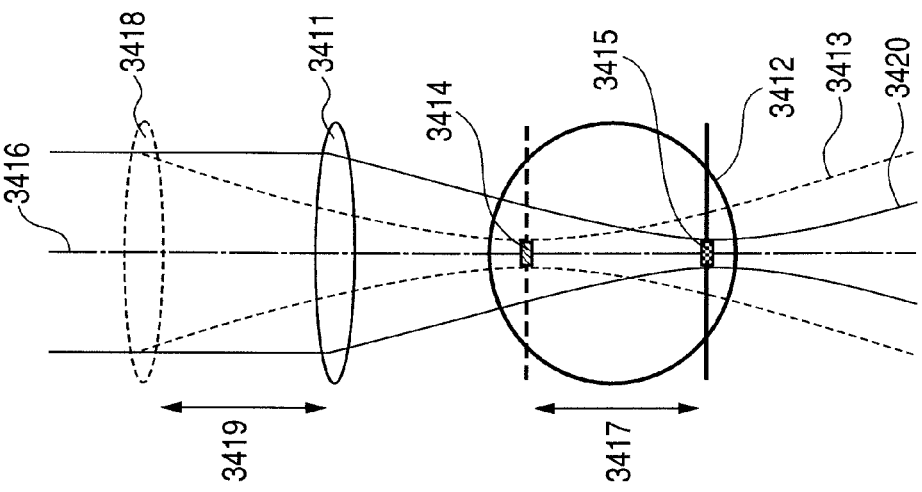
FIGS. 34A and 34B are schematic diagrams illustrating aspects of luminous fluxes incident on fundus examination object sites.
Figure 34A:
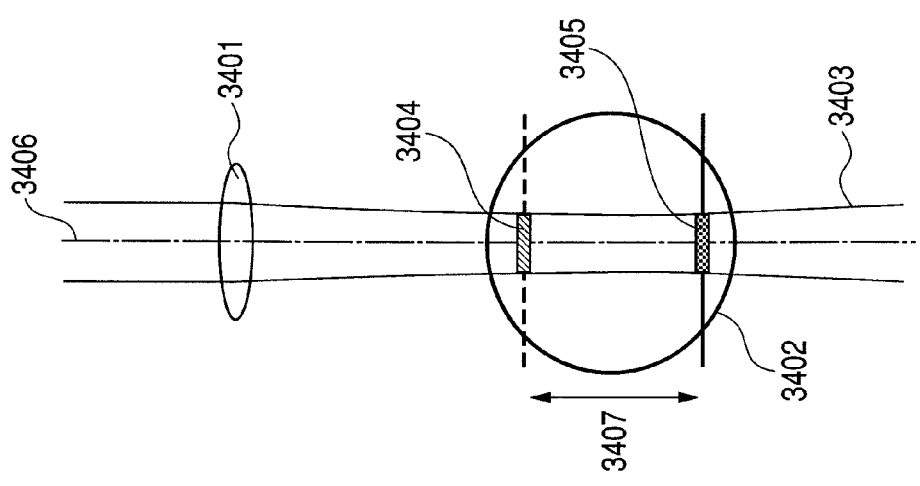
Figure 35B:
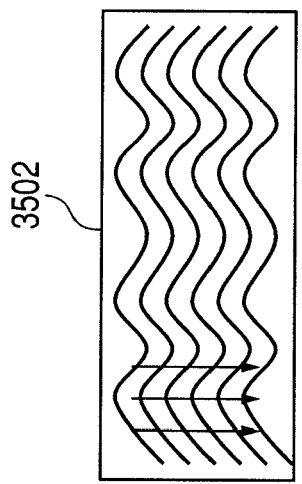
FIGS. 35A, 35B and 35C are schematic diagrams illustrating a positional offset between both images.
Figure 35C:
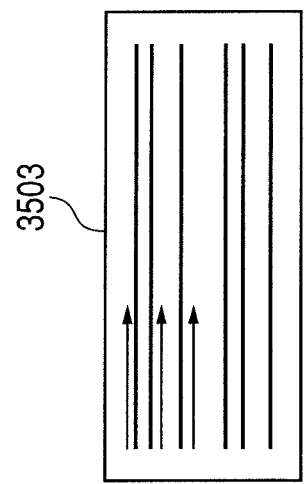
Figure 35A:
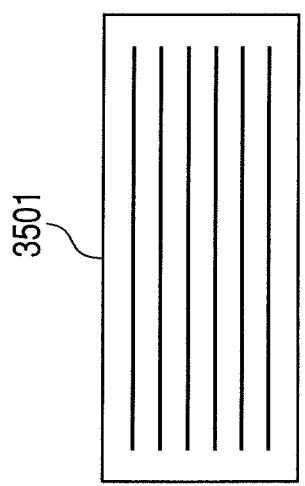

FIG. 34A is a schematic diagram at the time when not being the DF. At this time, a lens 3401 is fixed and is made to generate luminous flux 3403 whose main light is 3406. Thereby, a first focus 3404 and a second focus 3405 become almost the same size, and although a lateral resolution is low, a depth of focus 3407 can be made deep.

On the other hand, FIG. 34B is a schematic diagram at the time when being the DF. At this time, a lens (alternatively, a focusing optical system) can be made movable for a range of 3419 from 3418 to 3411. In addition, when a lens makes 3416 main light, luminous flux becomes 3413 when it is at a position 3418, and luminous flux becomes 3420 when it is at a position of 3411. Thereby, since focusing can be continued by the focusing optical system, the lateral resolutions of the first focus 3414 and the second focus 3415 are high, and depth of focus 3417 can be made deep.

Here, regions 3402 and 3412 illustrated by a circle in FIGS. 34A and 34B expresses a sectional view of an inspection object 5.

When the DF is applied to TD-OCT, obtaining measurement data can be continued in a high lateral resolution by making the focusing optical system perform focusing by synchronizing it with an operation of a movable reference mirror.

Also in the invention which relates to this embodiment, the dynamic focusing (DF) can be used to define the above-mentioned first focus and a second focus and obtain tomography image information including each of the focuses. In addition, it is needless to say that the DF is applicable also in other embodiments mentioned later.

(e) TS-OCT

A method called TS-OCT (Transversal Scan OCT) is disclosed in U.S. Pat. No. 5,321,501 and Japanese Application Laid-open No. 2002-515593 (pages 9 to 19, FIG. 1, and FIG. 2)). Also in the invention which relates to this embodiment, a tomography image at each focusing position can be obtained by the TS-OCT at the first image information obtaining step or second image information obtaining step.

Figure 32:
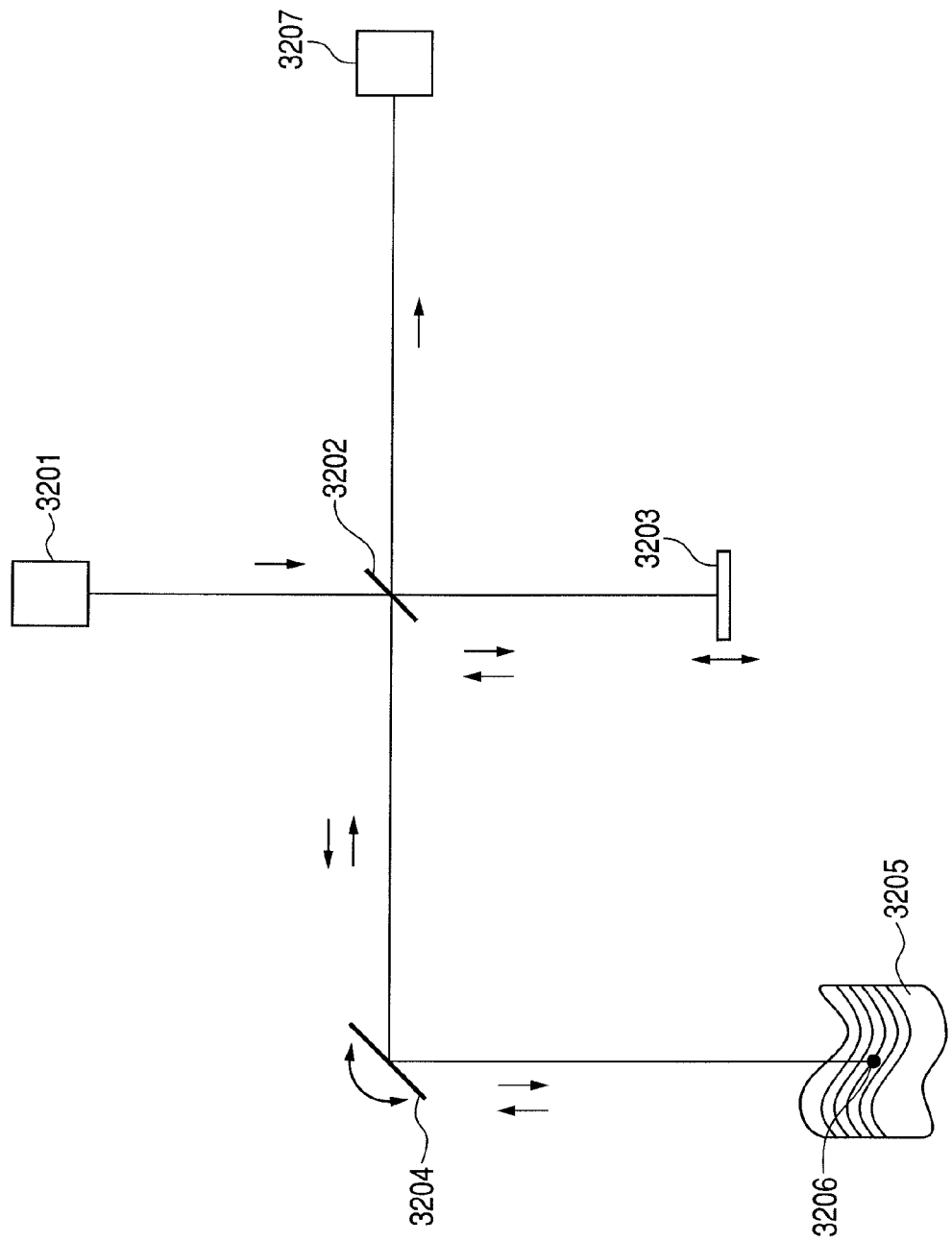
FIG. 32 is a schematic diagram illustrating construction of a conventional light interference measuring apparatus (TD).
Figure 33:
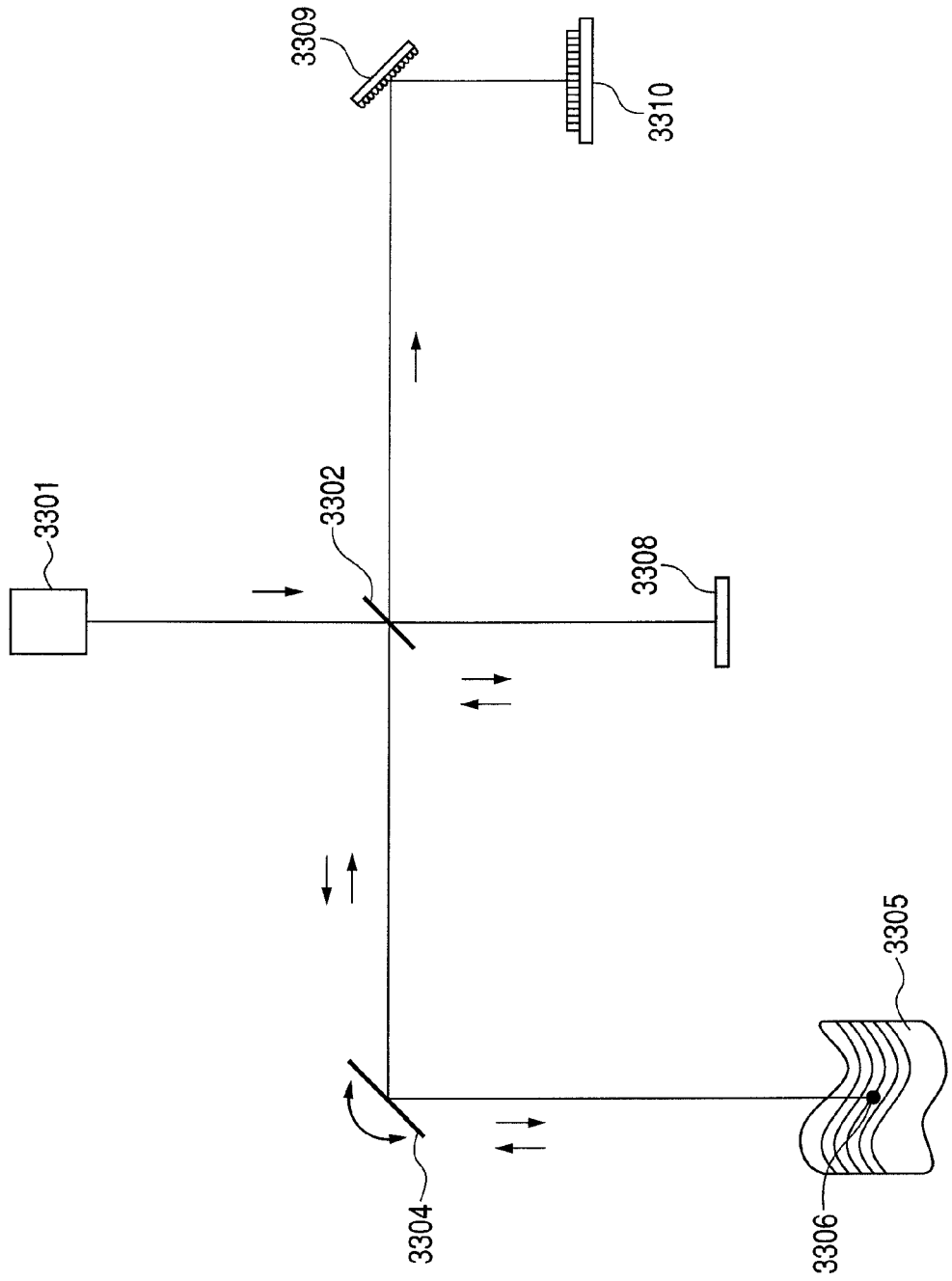
FIG. 33 is a schematic diagram illustrating construction of a conventional light interference measuring apparatus (SD).

Although this method is achieved by construction similar to the construction in FIG. 32 mentioned above, a frequency shifter, such as an AOM (acoustooptical modulator), is suitably used from difference in its scanning method. A phase of reference light can be linearly changed by generating a compressional traveling wave by a frequency shifter and using it as a moving diffraction grating. A carrier which is a carrier of image data is generated by using this frequency shifter.

Unlike a scanning method based on an A-scan of the above-described TD-OCT or SD-OCT, the scanning method of the TS-OCT is based on obtaining a two-dimensional image by a C-scan (scanning in an in-plane direction which is orthogonal to a depth direction inside an inspection object). Then, a plurality of these two-dimensional images is obtained in the depth direction inside a seen object, and a three-dimensional image is formed using it.

In this scanning method, since the movable reference mirror moves in the depth direction inside the inspection object after obtaining a two-dimensional image, there is a temporal margin from certain movement to the next movement in comparison with the A-scan. For this reason, the TS-OCT is easy to synchronize a focusing optical system with the movable reference mirror when moving it, and it can be said that it is a scanning method suitable for the above-mentioned DF.

Second Embodiment

Correction of SD-OCT Image with SD-OCT Image

An image forming method using an optical coherence tomography which relates to this embodiment has the following steps.

1. A first image information obtaining step of obtaining a one-dimensional or two-dimensional image of an inspection object at a position, including a first focus, with respect to an optical axis direction, which is a direction in which light is directed onto the inspection object, by a spectral domain optical coherence tomography 2. A second image information obtaining step of obtaining a one-dimensional or two-dimensional image of the inspection object at a position, including a second focus different from the first focus, with respect to the optical axis direction by a spectral domain optical coherence tomography 3. A step of correcting positional relation, with respect to the optical axis direction, between both of the image information obtained respectively by the first and second image information obtaining steps using tomography information of the inspection object which is obtained by at least one step of the first or second image information obtaining step, and forming a tomography image or a three-dimensional image of the inspection object.

Figure 2:
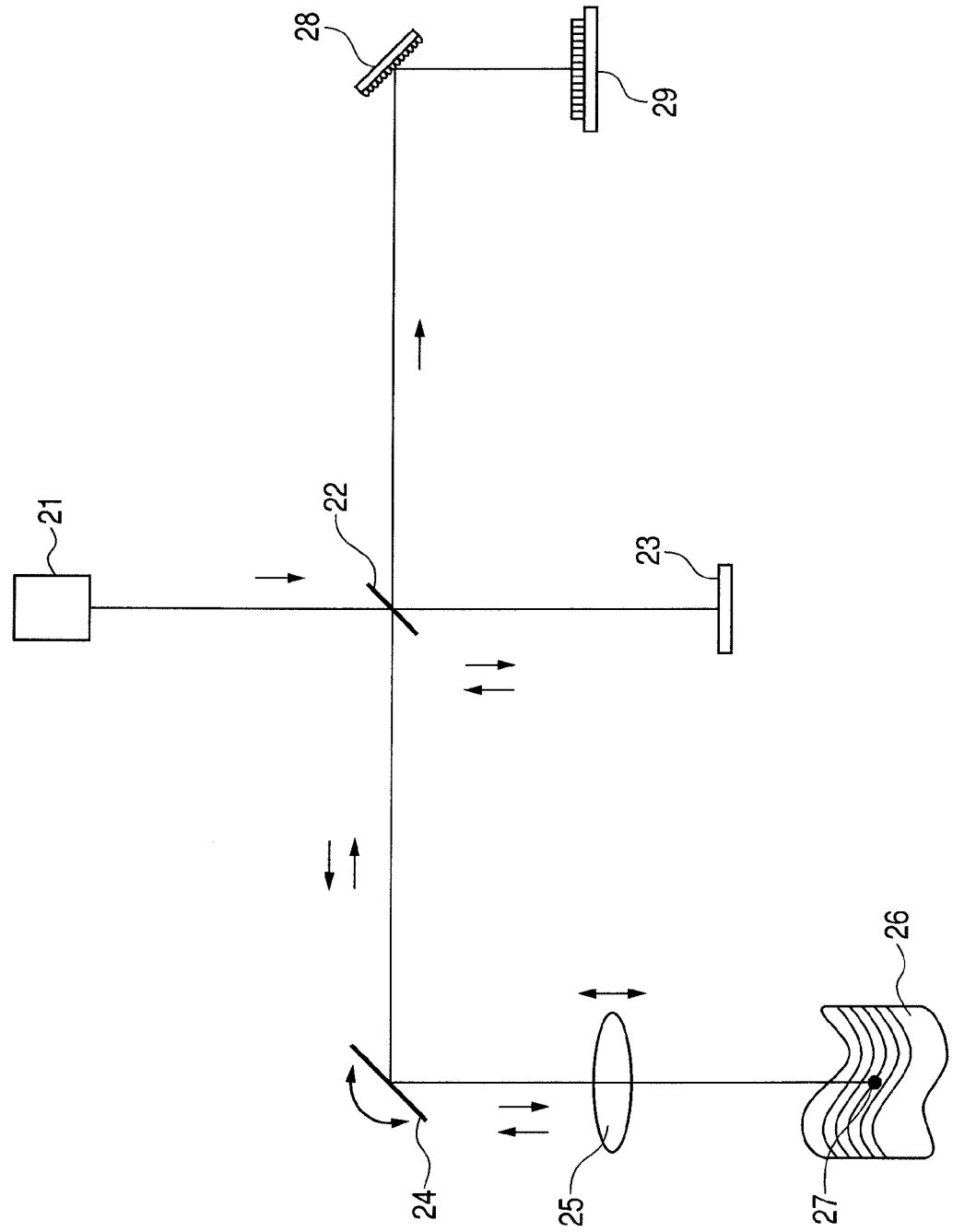
FIG. 2 is a schematic diagram for describing an optical coherence tomography which relates to the present invention.

Construction for performing the image forming method which relates to this embodiment is illustrated in FIG. 2. Reference numeral 21 denotes a light source, reference numeral 22 denotes light dividing means (although it serves also as a synthesis function, respective separate members can also serve), reference numeral 23 denotes a reflection plate, reference numeral 24 denotes light scanning means (it scans in a one-dimensional or two-dimensional direction), and reference numeral 25 denotes a lens. Reference numeral 26 denotes an inspection object and reference numeral 27 denotes a focusing position by the lens 25 and its vicinity. Reference numeral 28 denotes a spectroscope, and reference numeral 29 denotes a sensor array for performing detection every wavelength. The above-mentioned first and second image information can be acquired with the sensor array 29.

In the image forming method in this embodiment, unless a matter described in the above-described first embodiment is contradictory, it is applicable as it is.

Third Embodiment

SD-OCT with DF

In addition, an image forming method using an optical coherence tomography which relates to this embodiment is characterized by obtaining by a spectral domain optical coherence tomography a one-dimensional or two-dimensional image of an inspection object in an optical axis direction, in which light is directed onto the inspection object, respectively while changing a focal position with respect to an optical axis direction, and forming a tomography image or a three-dimensional image of the inspection object.

A focusing position can be defined by applying the above-described dynamic focusing mechanism.

In particular, data volume is reducible by leaving image information at a focusing position selectively, and eliminating the image information in other portions serially.

In the image forming method in this embodiment, unless a matter described in the above-described first embodiment is contradictory, it is applicable as it is.

Fourth Embodiment

Apparatus

An apparatus which relates to this embodiment is an optical coherence tomograph apparatus for performing the image forming methods described in the embodiments as stated above.

Specifically, it has at least a light source for causing light to impinge on an inspection object, a light dividing unit for dividing the light from the above-mentioned light source into signal light and reference light, and a detection unit for dispersing and detecting coherent light of the reference light and signal light. In the following embodiment, each unit will be described in detail.

In addition, it can be also constructed as follows as an apparatus which relates to this embodiment.
(Apparatus 1)

The first apparatus is equipped with a division optical system which divides light from a light source into reference light and signal light, a test optical system which guide the signal light to a specimen and changes an inspection position inside the specimen, and a synthesis optical system which synthesizes the reflected light from the specimen concerned with the reference light.

Then, it is equipped with an amplitude dividing unit in an approximate pupil position of an optical system which condenses and collimates the reflected light which spreads from a predetermined inspection point, belonging to the above-mentioned specimen, and its vicinity, or a position which is other than a pupil and in which area division of luminous flux passing the pupil concerned can be performed. Alternatively, it can be also said to be a luminous flux division unit for having an action of pupil division.

The amplitude dividing unit is a unit which performs amplitude division of the above-mentioned reflected light in a predetermined partial area. It is equipped with a non-spectral interference signal detection unit to detect at least one of the respective divided luminous fluxes concerned as an interference signal non-spectral with the above-mentioned reference light, and a spectral interference signal detection unit to detect at least one of the other luminous fluxes as an interference signal spectral with the above-mentioned reference light. Then, it includes a numeric conversion unit to perform predetermined numeric conversion to a function of the coherent light signal, which is the above-mentioned spectral interference signal obtained by the spectral interference signal detection unit concerned versus the wavelength. The above-mentioned spectral interference signal is converted into a function of the coherent light signal versus the light arrival position by the numeric conversion unit concerned.

In this apparatus, it is recognized as follows that an origin of the specimen moved because of a turbulence when different inspection positions were measured, with respect to the function of the coherent light signal versus the inspection position obtained by the above-mentioned non-spectral interference signal detection unit about a plurality of inspection positions by a test optical system. Specifically, it is desirable to recognize it using the above-mentioned function of the coherent light signal versus the light arrival position obtained by performing numerical conversion from the above-mentioned spectral interference signal which is an output of the above-described other spectral interference signal detection unit, and to adjust inspection position information of the above-mentioned function of the coherent light signal versus the inspection position.

(Apparatus 2)

The second apparatus is equipped with a division optical system which divides light from a light source into reference light and signal light, a test optical system which guide the signal light to a specimen and changes an inspection position inside the specimen, and a synthesis optical system which synthesizes the reflected light from the specimen concerned with the reference light.

Then, it is equipped with an amplitude dividing unit in an approximate pupil position of an optical system which condenses and collimates the reflected light which spreads from a predetermined inspection point, belonging to the above-mentioned specimen, and its vicinity, or a position which is other than a pupil and in which area division of luminous flux passing the pupil concerned can be performed. The amplitude dividing unit is a unit which performs amplitude division of the above-mentioned reflected light in a predetermined partial area. Furthermore, it is equipped with a spectral interference signal detection unit to detect at least one of the respective divided luminous fluxes concerned as an interference signal spectral with the above-mentioned reference light, and another spectral interference signal detection unit to detect at least one of the other luminous fluxes as an interference signal spectral with the above-mentioned reference light. Then, it includes a numeric conversion unit to perform predetermined numeric conversion to a plural number of a function of the coherent light signal, which is the plurality of above-mentioned spectral interference signal obtained by the plurality of spectral interference signal detection units, versus the wavelength. The plurality of above-mentioned spectral interference signals can be converted into a plurality of functions of the coherent light signal versus the light arrival position by the numeric conversion unit concerned.

Here, it is recognized as follows that original specimen moved because of turbulence when different inspection positions were measured with respect to the function of the coherent light signal versus the inspection position obtained by one of the above-mentioned non-spectral interference signal detection units about the plurality of inspection positions by the test optical system. Specifically, it is recognized using the function of the above-mentioned coherent light signal versus the light arrival position obtained by numeric conversion from the above-mentioned spectral interference signal which is an output of the above-described other spectral interference signal detection unit. Then, it can be adjusted about inspection position information of the above-mentioned function of the coherent light signal versus the inspection position.

In addition, in the above-mentioned apparatus 1 or apparatus 2, an amplitude dividing unit which performs amplitude division of reflected light from the above-mentioned specimen can be also constructed by a time sharing system of division unit.

(Apparatus 3)

The Fourier domain method needs a light source for the TD-OCT for obtaining the above-mentioned first and second image information, and a light source for the SS-OCT for obtaining the above-mentioned third image information, in the case of the SS-OCT.

In addition, the above-mentioned light sources are a first light source for radiating a plurality of center wavelengths, and a second light source for radiating a single center wavelength.

Furthermore, when the TD-OCT was used, it was already described that it was suitable to have a frequency shifter for giving a difference between a frequency of the above-mentioned reference light and a frequency of the above-mentioned signal light.

At this time, the above-mentioned frequency shifter is arranged in a path of light which the above-mentioned second light source radiates, and a path of light which the above-mentioned first light source radiates is arranged so as to be different from the path of the light which the above-mentioned second light source radiates. By this construction, the light which the above-mentioned first light source radiates is never influenced by the above-mentioned frequency shifter. The influence by the above-mentioned frequency shifter will be mentioned later.

Fifth Embodiment

Application of Dynamic Focusing to Each Embodiment

An image forming method using an optical coherence tomograph apparatus which relates to this embodiment can be performed at the following steps.

In addition, this embodiment is obtained by applying the above-mentioned dynamic focusing to the first embodiment.

1. A first image information obtaining step of obtaining first image information (a one-dimensional, two-dimensional, or three-dimensional image) of an inspection object at a first focusing position with respect to an optical axis direction which is a direction in which light is directed onto the inspection object 2. A step of changing a focusing position by dynamic focusing from the first focusing position to a position of a second focus which is different from the first focus with respect to the optical axis direction 3. A second image information obtaining step of obtaining second image information (a one-dimensional, two-dimensional, or three-dimensional image) of the inspection object at a position of the second focus 4. A step of obtaining third image information, which is tomography image information of the inspection object and includes a tomography image of the inspection object at least at one focusing position of the first focus or the second focus, by Fourier domain optical coherence tomography 5. A step of associating positional relation, with respect to the optical axis direction, between the first image information and the second image information using the third image information, and forming a tomography image or a three-dimensional image of the inspection object.

Here, the above-mentioned positional relation, with respect to the above-mentioned optical axis direction, between the above-mentioned first image information and the above-mentioned second image information which are associated can be corrected. In addition, with respect to the above-mentioned correction, the correction method described in the first embodiment can be used suitably so as not to be contradictory. Thereby, the positional relation between both image information with respect to the depth direction can be corrected. In addition, image information in a high lateral resolution can be acquired by the dynamic focusing.

In addition, the above-mentioned first and second image information obtaining steps can be made into a step of obtaining a one-dimensional or two-dimensional image of the above-mentioned inspection object by the above-mentioned time domain optical coherence tomography. Furthermore, the above-mentioned third image information can be acquired by the above-mentioned spectral domain optical coherence tomography. Of course, the above-mentioned third image information can also be acquired by using the above-mentioned SS-OCT.

(a) Correction of TS-OCT Image with SD-OCT Image

Next, an image forming method using an optical coherence tomography which relates to another embodiment will be described.

Here, the above-mentioned TS-OCT (Transversal Scan OCT) and SD-OCT (Spectral Domain OCT: spectral domain optical coherence tomography) are applied. They can be performed by the following steps.

1. A first image information obtaining step of obtaining first image information, which is a C-scan image of an inspection object at a first focusing position, with respect to an optical axis direction, which is a direction in which light is directed onto the inspection object, by the time domain optical coherence tomography 2. A step of changing a focusing position by the dynamic focusing from the first focusing position to a position of a second focus, which is different from the first focus, with respect to the optical axis direction 3. A second image information obtaining step of obtaining second image information, which is a C-scan image of the inspection object, at the second focusing position by the time domain optical coherence tomography 4. A step of obtaining third image information, which is tomography image information of the inspection object and includes a tomography image of the inspection object at a position of at least one focus of the first focus or the second focus position, by the spectral domain optical coherence tomography 5. A step of associating positional relation, with respect to the optical axis direction, between the first image information and the second image information using the third image information, and forming a tomography image or a three-dimensional image of the inspection object.

Here, the above-mentioned positional relation, with respect to the above-mentioned optical axis direction, between the above-mentioned first image information and the above-mentioned second image information which are associated can be corrected. In addition, with respect to the above-mentioned correction, the correction described in the first embodiment can be used suitably so as not to be contradictory. Thereby, the positional relation between both image information with respect to the depth direction can be corrected. In addition, image information in a high lateral resolution can be acquired by the dynamic focusing.

Nevertheless, the correction according to the present invention is not limited to these.

In addition, the following units can be used for an image forming method using an optical coherence tomography which relates to this embodiment.

(a-1) Influence by Frequency Shifter

Here, as described in the first embodiment, when correction is performed using the spectral domain optical coherence tomography, it is good to take the following points into consideration.

A frequency shifter such as an AOM can be used when obtaining a tomography image by the time domain optical coherence tomography. The above-mentioned frequency shifter shifts a phase (frequency) linearly to time. In this embodiment, it is suitable to give a difference to the respective frequency of the reference light and the signal light which were divided by the light dividing unit (first light dividing unit). Thereby, when the above-mentioned reference light and the above-mentioned signal light interfere, a beat (a difference frequency) can be generated.

Here, it is called heterodyne detection to detect light obtained by different frequencies being made to interfere.

In order to obtain image information of an inspection object, a change in light by reflection by the inspection object is detected. However, light changes also by refractive indices in a path which light passes besides the change by the above-mentioned reflection. Causes by which a refractive index changes are a swing of an apparatus, temperature variation of the air in the path of light, etc., for example. A change of a refractive index appears in the above-mentioned beat as a change in a wavelength of light, and a change in light by reflection by the above-mentioned inspection object appears as a change in an amplitude. Thereby, the image information of an inspection object can be acquired with good accuracy by seeing the change in an amplitude of a beat.

In addition, coherent light is divided using the light dividing unit, and one side of the light is given phase inversion. When a difference is taken between information on detection of this phase-inverted light, and light detecting another side of light, information that a DC component obtained from light generated from the light source is eliminated can be acquired. Thereby, an S/N ratio can be increased.

By the way, when obtaining tomography information by the spectral domain optical coherence tomography, a spectroscope is used as this detection unit. As for the above-mentioned beat input into the above-mentioned spectroscope, while dispersed by the spectroscope, respective dispersed frequencies are shifted relatively, and the above-mentioned tomography information becomes detection including noise. Here, a time interval of the frequency shift of light by the above-mentioned frequency shifter is generally shorter than a time when light is input into the above-mentioned spectroscope.

In order to avoid the influence by the above-mentioned frequency shifter which poses a problem at the time of the above detection by the spectral domain optical coherence tomography, the following methods can be used.

(a-2) Reference Signal and Synchronization

First, there is a method of performing synchronization with a reference signal from a drive circuit of the above-mentioned frequency shifter. Thereby, in the detection with the spectral domain optical coherence tomography, the above-mentioned frequency shifter can be controlled so that a signal obtained by a detection unit of the spectral domain optical coherence tomography may become stronger than a signal obtained by a detection unit of the time domain optical coherence tomography.

For example, the above-mentioned frequency shifter can be controlled as follows.

That is, when obtaining the above-mentioned first or second image information, the control is made to shift a frequency of the above-mentioned reference light or the above-mentioned signal light. Specifically, a power supply of the above-mentioned frequency shifter is turned on, and it is operated.

Then, when obtaining the above-mentioned tomography information, the control is made to prevent the frequency of the above-mentioned reference light or the above-mentioned signal light from shifting. Specifically, the power supply of the above-mentioned frequency shifter is turned off, and operation is stopped.

Of course, the present invention is not limited to using the above-mentioned frequency shifter. In addition, even if the above-mentioned frequency shifter is used, the present invention is not limited to performing the above-mentioned control.

(a-3) Adjustment of Ratio of Intensities of Light Transmitted and Reflected

In addition, there is also a method of converting a path of light using an optical path conversion unit.

For example, the above-mentioned optical path conversion unit can be controlled as follows.

First, when obtaining the above-mentioned first or second image information, the control is made so that light may pass a path for obtaining an image by the above-mentioned time domain optical coherence tomography. In addition, when obtaining the above-mentioned third image information, the control is made so that light may pass a path for obtaining an image by the above-mentioned spectral domain optical coherence tomography.

Here, an optical switch can be used for the above-mentioned optical path conversion unit. The optical switch can switch a light path in high speed and low loss, and is used for optical communication etc. In types of optical switches, there are what switch a light path mechanically, and what switch an advantageous effect of light using a thermooptic effect (a change in a refractive index by temperature). Although an optical fiber is applicable to a light path at this time, the present invention is not limited to this.

At this time, the control can also be made as follows using the above-mentioned frequency shifter. That is, when obtaining the above-mentioned first or second image information, the control can be made to shift a frequency of the above-mentioned reference light or the above-mentioned signal light. Furthermore, when obtaining the above-mentioned third image information, the control can be made to prevent a frequency of the above-mentioned reference light or the above-mentioned signal light from shifting.

Of course, the present invention is not limited to using the above-mentioned frequency shifter. In addition, even if the above-mentioned frequency shifter is used, the present invention is not limited to performing the above-mentioned control.

(a-4) Spatial Polarization Modulator

Furthermore, there is also a method of adjusting the ratio of intensities of light transmitted through and reflected on the light dividing unit. The above-mentioned adjustment can be performed by using a spatial polarization modulator for converting polarization. By controlling the above-mentioned spatial polarization modulator and converting polarization at high speed, a reflectance (transmittance) of the light dividing unit (second light dividing unit) can be adjusted. Here, the above-mentioned second light dividing unit is a unit for dividing coherent light of the above-mentioned reference light and the above-mentioned signal light into two. That is, it divides the above-mentioned coherent light into light for obtaining an image by the above-mentioned time domain optical coherence tomography, and light for obtaining an image by the above-mentioned spectral domain optical coherence tomography. Then, the above-mentioned second light dividing unit is controlled as follows.

For example, the above-mentioned spatial polarization modulator is controlled as follows. That is, when obtaining the above-mentioned first or second image information, the control is made so that the light for obtaining an image by the time domain optical coherence tomography may become stronger than the light for obtaining an image by the above-mentioned spectral domain optical coherence tomography.

Furthermore, when obtaining the above-mentioned third image information, the control is made so that the light for obtaining an image by the spectral domain optical coherence tomography may become stronger than the light for obtaining an image by the above-mentioned time domain optical coherence tomography. Of course, although it can be also combined with the control of a frequency shifter mentioned above, the present invention is not limited to this.

Here, the above-mentioned spatial polarization modulator can be constructed of a PEM (Photoelastic Modulator), an EOM (Electro optic modulator), etc.

(a-5) Optical Coherence Tomograph Apparatus

An optical coherence tomography apparatus for performing an image forming method which relates to this embodiment will be described.

First, it has a light source for causing light to impinge on an inspection object, a first light dividing unit for dividing the light from the above-mentioned light source into signal light and reference light, and a detection unit for detecting coherent light of the reference light and signal light.

A light source that generates light whose center wavelength is 840 nm which is shorter than a wavelength band which is influenced by absorption by water largely, and which is longer than a wavelength band of visible light is suitable for the above-mentioned light source. In addition, the above-mentioned first light dividing unit and the above-mentioned detection unit will be described in detail in the following embodiment.

In addition, a control unit for controlling this embodiment can be provided.

Furthermore, as mentioned above, the above-mentioned frequency shifter, the above-mentioned second light dividing unit, and the spatial polarization modulator can be used.

The above-mentioned construction is described in detail in a fifth Embodiment.

(b) Correction of SD-OCT Image with SD-OCT Image

In addition, an image forming method using an optical coherence tomography which relates to another embodiment will be described. In addition, this embodiment is obtained by applying the above-mentioned dynamic focusing to the second embodiment.

1. A first image information obtaining step of obtaining first image information (a one-dimensional, two-dimensional, or three-dimensional image) of an inspection object at a first focusing position with respect to an optical axis direction which is a direction in which light is directed onto the inspection object by the Fourier domain optical coherence tomography 2. A step of changing a focusing position by dynamic focusing from the first focusing position to a position of a second focus which is different from the first focus with respect to the optical axis direction 3. A second image information obtaining step of obtaining second image information (a one-dimensional, two-dimensional, or three-dimensional image) of the inspection object at a position of the second focus by the Fourier domain optical coherence tomography 4. A step of associating positional relation, with respect to the optical axis direction, between the first image information and the second image information using tomography information of the inspection object which is obtained by at least one step of the first or second image information obtaining step, and forming a tomography image or a three-dimensional image of the inspection object.

Here, the above-mentioned positional relation, with respect to the above-mentioned optical axis direction, between the above-mentioned first image information and the above-mentioned second image information which are associated can be corrected. In addition, with respect to the above-mentioned correction, the correction described in the first embodiment can be used so as not to be contradictory. Thereby, the positional relation between both image information with respect to the depth direction can be corrected. In addition, image information in a high lateral resolution can be acquired by the dynamic focusing.

Furthermore, the above-mentioned first and second image information can be acquired by the above-mentioned spectral domain optical coherence tomography. Of course, the above-mentioned first and second image information can also be acquired by using the above-mentioned SS-OCT.

An optical coherence tomograph apparatus for performing an image forming method which relates to this embodiment has the following construction. That is, it includes a light source for causing light to impinge on an inspection object, a light dividing unit for dividing the light from the above-mentioned light source into signal light and reference light, and a detection unit for detecting coherent light of the reference light and signal light.

In addition, in the image forming method in this embodiment, unless a matter described in the above-described first and second embodiment is contradictory, it is applicable as it is.

(c) Pattern Using Non-Limited Focusing Positions at the Time of FD-OCT

Furthermore, an image forming method using an optical coherence tomography which relates to another embodiment will be described. In addition, this embodiment is obtained by applying the above-mentioned dynamic focusing to (c) of the first embodiment.

1. A first image information obtaining step of obtaining first image information (a one-dimensional, two-dimensional, or three-dimensional image) of an inspection object at a first focusing position with respect to an optical axis direction which is a direction in which light is directed onto the inspection object 2. A step of changing a focusing position by dynamic focusing from the first focusing position to a position of a second focus which is different from the first focus with respect to the optical axis direction 3. A second image information obtaining step of obtaining second image information (a one-dimensional, two-dimensional, or three-dimensional image) of the inspection object at a position of the second focus 4. A step of obtaining tomography image information with respect to the optical axis direction of the inspection object by the Fourier domain optical coherence tomography 5. A step of associating positional relation, with respect to the optical axis direction, between the first image information and the second image information using the tomography image information, and forming a tomography image or a three-dimensional image of the inspection object.

Here, the above-mentioned positional relation, with respect to the above-mentioned optical axis direction, between the above-mentioned first image information and the above-mentioned second image information which are associated can be corrected. In addition, with respect to the above-mentioned correction, the correction described in the first embodiment can be used so as not to be contradictory. Thereby, the positional relation between both image information with respect to the depth direction can be corrected. In addition, image information in a high lateral resolution can be acquired by the dynamic focusing.

Nevertheless, the correction according to the present invention is not limited to these.

In addition, in the above-mentioned embodiment, the focusing position at the time of obtaining tomography image information by the Fourier domain optical coherence tomography is not limited particularly.

Here, the above-mentioned tomography image information 4505 can be obtained at a position of a third focus 4508 which is different from the positions of the above-mentioned first and second focus 4501 and 4503, with respect to the above-mentioned optical axis direction. At this time, the above-mentioned tomography image information 4505 can be obtained, including the image information of the inspection object at the positions of the first and second focus 4501 and 4503.

Examples according to the present invention will be described below.

EXAMPLES

Example 1

TD-OCT Image+SD-OCT Image for Correction

Figure 3:
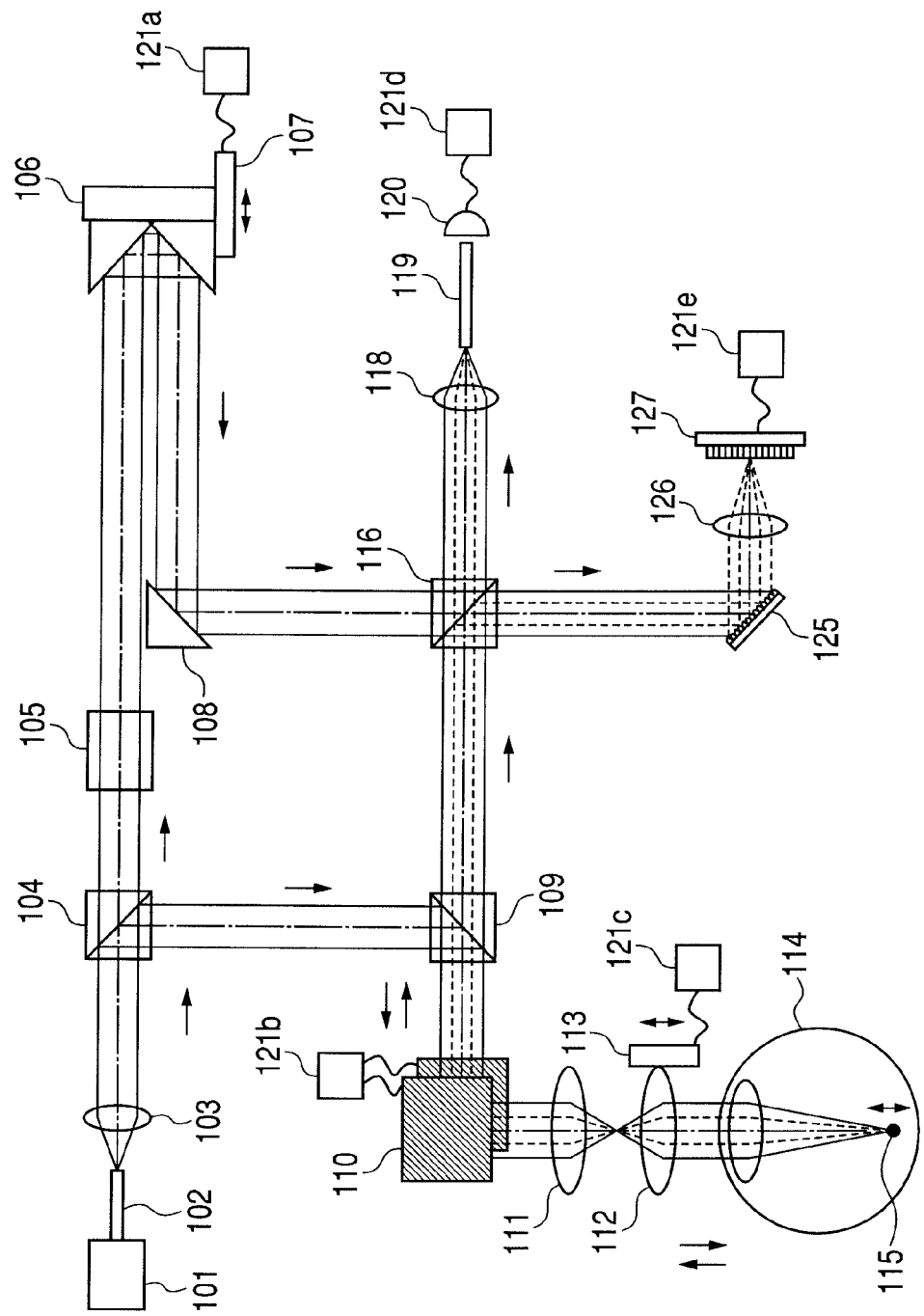
FIG. 3 is a schematic diagram illustrating construction of a light interference measuring apparatus in a first example of the present invention.

Example 1 will be described with reference to FIG. 3.

First, light emitted from a light source 101 is optically guided by a single-mode optical fiber 102, and the light emitted from a fiber edge is converted into parallel light by a collimator lens 103 to be divided into reference light and signal light by a division optical system 104.

The reference light is reflected by an optical delay unit 106 after its optical frequency is shifted by Δf by a frequency shifter 105, and is guided to a synthesis optical system 116 by a reflection mirror 108. Here, a position of the optical delay unit 106 is controlled by a position driving unit 107 so that an optical path may become a predetermined length.

After impinging on a light guiding division optical system 109, the signal light is guided to a test optical system for an eye 114 and a fundus examination object site 115 which are inspection objects. Here, the test optical system is formed by the light guiding division optical system 109, a light beam scanning optical system 110, a scanning lens 111, and a lens 112 for an eye. In addition, the lens 112 for an eye is driven to the optical axis direction of incident light by a focusing position driving unit 113. At this time, the focusing position driving unit 113 is driven while being synchronized with drive of an optical delay unit. Furthermore, the light beam scanning optical system 110 has an action of making main light of the signal light incline so as to make it form inclination angles in two orthogonal directions to an optical axis. Thereby, luminous flux which passes the scanning lens 111 and the lens 112 for an eye is given angle scan on a pupil (iris) of an eye. In consequence, it was constructed so as to scan an in-plane of a vertical plane (x-y plane) to the optical axis direction (depth direction) on an eyeground in the fundus examination object site 115 because of an optical action of an eye. A part of light passing through an approximately same optical path at the time of impinging on the fundus examination object site 115 among reflected light from the fundus examination object site 115, or back-scattered light, and proceeding to a direction reverse to incident light is guided to the synthesis optical system 116 by the light guiding division optical system 109.

Next, the reference light and signal light are synthesized by the synthesis optical system 116, and a part of coherent light with the synthetic amplitude added as a complex amplitude impinges on a condensing optical system 118. Then, it is optically coupled to a single-mode optical fiber 119, a component which coincides with a mode of the fiber is selected to propagate inside the fiber, and it impinges on a photoelectric conversion detector 120. Furthermore, it is converted into an electric signal and is transmitted to an OCT processing apparatus 121*d*. Here, the component which coincides with the mode of the fiber is a confocal component conjugate with divergent light from a point on the fundus examination site 115.

A synthetic amplitude added as a complex amplitude of coherent light of reference light and signal light has an amplitude of heterodyne interference which has a frequency difference $\Delta f$, generated by the frequency shifter 105, as a carrier frequency. Here, the wave by heterodyne interference is what an amplitude absolute value vibrates temporally at the frequency $\Delta f$. Furthermore, it is known that the temporal oscillation of the amplitude absolute value of this synthetic amplitude becomes an opposite phase. In this way, a C-scan image (when a depth direction is made a z-axial direction, image in xy in-plane directions which intersects it) at an individual focusing position can be acquired with respect to the depth direction of a detection object by the so-called TD-OCT method.

On the other hand, a part of coherent light by the synthesis optical system 116 impinges on a spectroscopic diffraction grating 125. Then, it is condensed by a wavelength division imaging lens 126, and spectral interference signal detection is performed by performing strength detection every wavelength by a line sensor 127. That is, image information including a tomography image of a detected object at a predetermined focusing position is obtained with respect to the depth direction of the detected object by the SD-OCT method which is one of the Fourier domain optical coherence tomography. Then, correction is performed using an SD-OCT image with respect to the depth direction of a plurality of C-scan images by the TD-OCT method. A correction method will be mentioned later.

In addition, the position driving unit 107, light beam scanning optical system 110, focusing position driving unit 113, photoelectric conversion detector 120, and line sensor 127 perform drive and detection by inputs and outputs by OCT processing apparatuses 121*a*, 121*b*, 121*c*, 121*d*, and 121*e*, respectively.

Example 2

Pupil Division (1)—Different Transmittance

Figure 4:
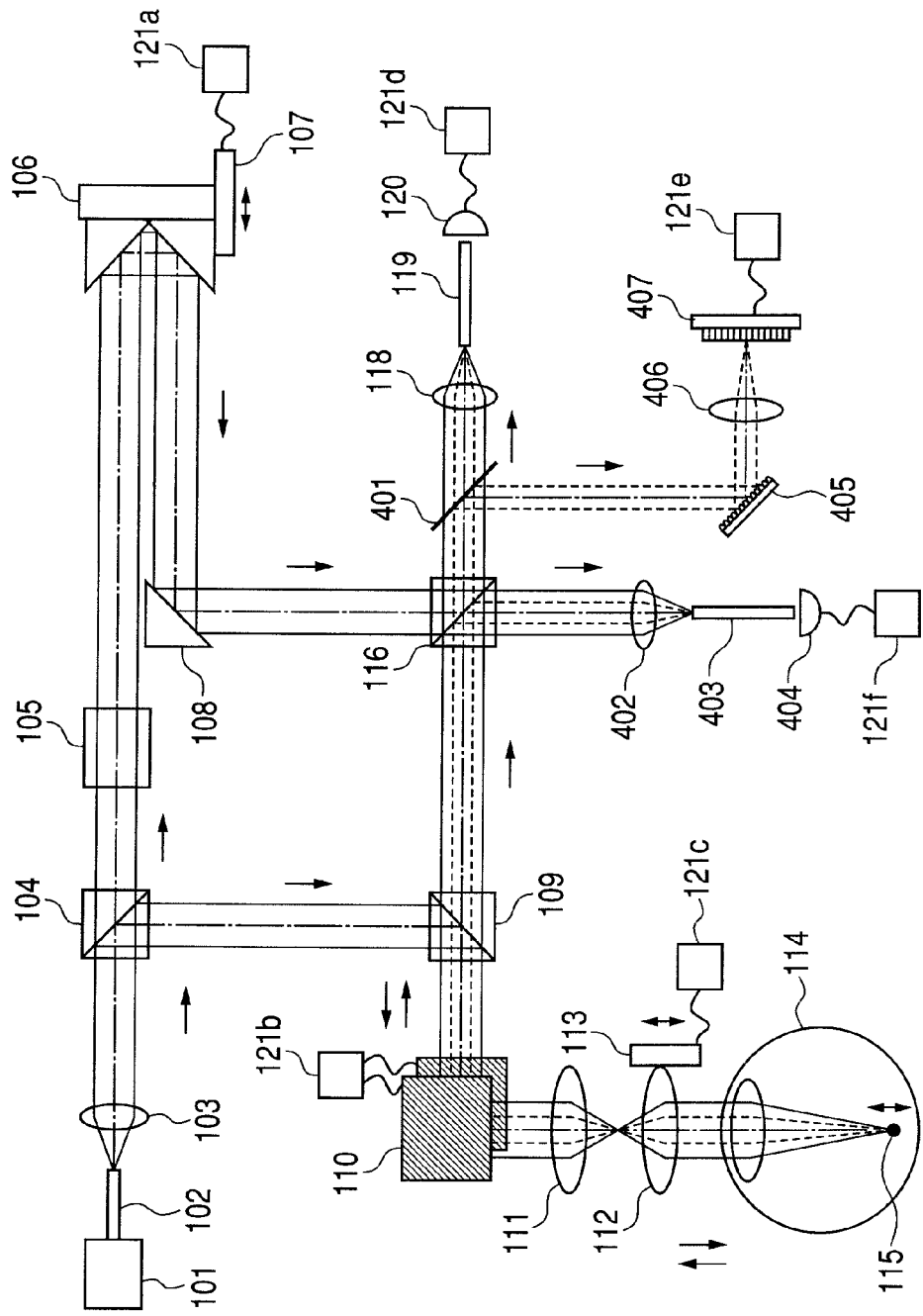
FIG. 4 is a schematic diagram illustrating construction of a light interference measuring apparatus in a second example of the present invention.

Example 2 will be described with reference to FIG. 4. Example 2 is a modified example of Example 1, and a pupil division optical system 401 is newly added to the construction. In addition, a condensing optical system 402, a single-mode optical fiber 403, and a light conversion detector 404 are also added to the construction.

A part of coherent light obtained by synthesizing reference light and signal light by the synthesis optical system 116 impinges on the condensing optical system 118, and a further part impinges on the condensing optical system 402. Here, the light which goes to the condensing optical system 118 from the synthesis optical system is divided by the pupil split optical system 401, and impinges on the spectroscopic diffraction grating 405. Then, it is condensed by a wavelength division imaging lens 406, and is given intensity detection every wavelength by a line sensor 407. The division by the pupil split optical system 401 can obtain the same advantageous effect as the division in the light beam scanning optical system 110.

Here, the light beam scanning optical system 110 is equivalent to a pupil position at which main light intersects. Images in the depth direction can be obtained in a deep depth of focus in batch by detecting spectral interference in a low NA using the pupil split optical system 401.

On the other hand, the light incident on the condensing optical system 402 is optically coupled to the single-mode optical fiber 403, and a component which coincides with a mode of the fiber is selected, propagates inside the fiber, impinges on the photoelectric conversion detector 404, is converted into an electric signal, and is transmitted to an OCT processing apparatus 121*f*. Here, optical intensity noise resulting from the set optical system 402, single-mode optical fiber 403, light source, and the like becomes in-phase in two of photoelectric conversion detectors 120 and photoelectric conversion detector 404. For this reason, noise reduction can be achieved by performing differential detection.

Figure 5A:
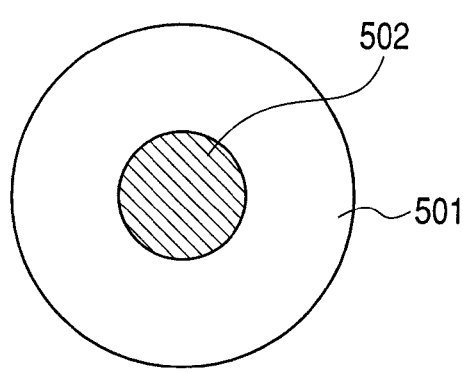
FIGS. 5A, 5B, 5C and 5D are schematic diagrams illustrating construction of a pupil division optical system in the second example of the present invention.

Next, the pupil division optical system 401 will be described using schematic diagrams in FIGS. 5A to 5D. FIG. 5A shows a pupil division method of this Example, and is constructed of a transparent portion 501 and a translucent half-reflection part 502. As for the pupil division optical system 401 used in this Example, as shown in FIG. 5B, the transparent portion 504 is specified with a predetermined effective diameter on a glass substrate, and its periphery becomes a holding unit 503. A center portion is constructed of the translucent half-reflection membrane 505 which is made of chromium being given vapor deposition on the glass substrate. A transmittance and a reflectance of the translucent and half-reflection membrane 505 are the same ratio approximately, and it is constructed at about 45% of transmission and 45% of reflection after subtraction of about 10% of absorption. Of course, transmittance and reflectance are not limited to these values.

Figure 5C:
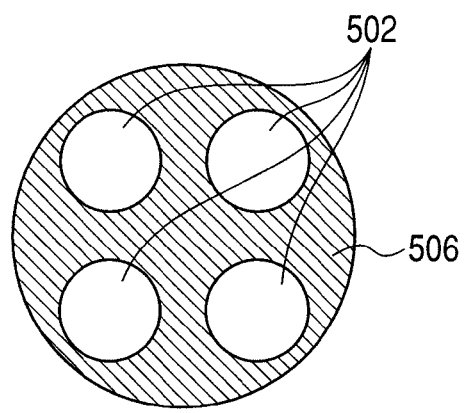
Figure 5B:
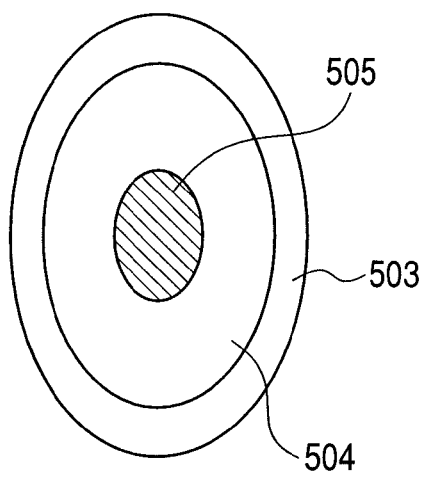
Figure 5D:
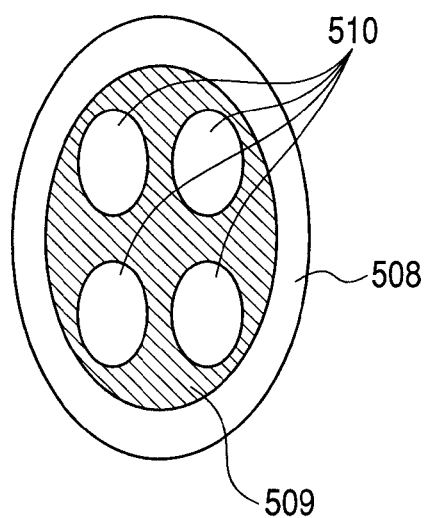

In addition, a pupil division method can be constructed as shown in FIG. 5C. It is constructed of a transparent portion 507 and a translucent half-reflection portion 506, and the transparent portion 507 is arranged in a quadrupole shape. Specifically, as shown in FIG. 5D, the pupil division optical system 401 is constructed of the transparent portions 510, which are arranged in the quadrupole shape, and a translucent half-reflection membrane 509, and a periphery of the translucent half-reflection membrane 509 becomes a holding unit 508. It is desirable to set a transmittance of a translucent half-reflection membrane higher than its reflectance since an area of transparent portions is small in this pupil division method. For example, although setting at 80% is desirable, it is not limited to this.

Next, an OCT processing unit 121 which performs signal processing, control, and imaging of an optical interference detection system of this Example will be described with reference to FIG. 8. FIG. 8 illustrates schematically a functional block diagram of the OCT processing unit 121.

First, an electric signal from the photoelectric conversion detectors 120 and 124 is given differential amplification by a circuit including an amplifier 801, and passes a filter/detector 802 having a band pass filter, whose center is the carrier frequency $\Delta f$, and a detection circuit. After that, after analog to digital conversion is performed by the digital sampling part 803, it is sent to a central process unit 804. The following comparison processing is performed in the central process unit 804.

A digital light interference signal after detection which is transmitted in time series is compared with the following signals.

Specifically, it is compared with a scanner position signal/synchronizing signal from an XY scanner driver 806, a delay position signal/synchronizing signal from an optical delay driver 807, and a focus position signal from a focus driver 808.

By this, the light interference signal and a position on a fundus examination object site are associated. Then, a light interference signal is assigned every predetermined pixel, and imaging is performed. This image is a so-called TS-OCT image. On the other hand, the spectral interference signal from the line sensor 407 is incorporated through the line image acquisition unit 809, a wavelength axis is converted into an axis of a tomography-directional position by an FFT (fast Fourier transform) processing unit, and tomography image data equivalent to one line of so-called A-scan is formed. This image is a so-called SD-OCT image.

Here, with reference to FIGS. 7A to 7D, difference between a TD-OCT image and an SD-OCT image in this Example will be described.

Reference numeral 700 denotes a tomography image with respect to a depth direction of an inspection object. In FIG. 7A, although the TD-OCT images 701 and 703 have high lateral resolutions, and obtain a size of one pixel in the depth direction, the SD-OCT images 702 and 704 have low lateral resolutions, and obtain an image for one scan line at one time in the depth direction.

Figure 6A:
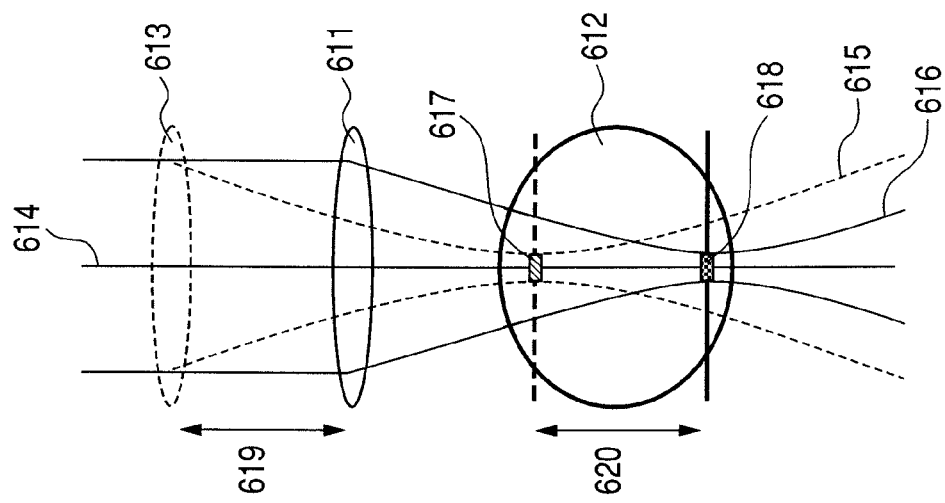
FIGS. 6A and 6B are schematic diagrams illustrating aspects of luminous fluxes incident on fundus examination object sites in the second example of the present invention.
Figure 6B:
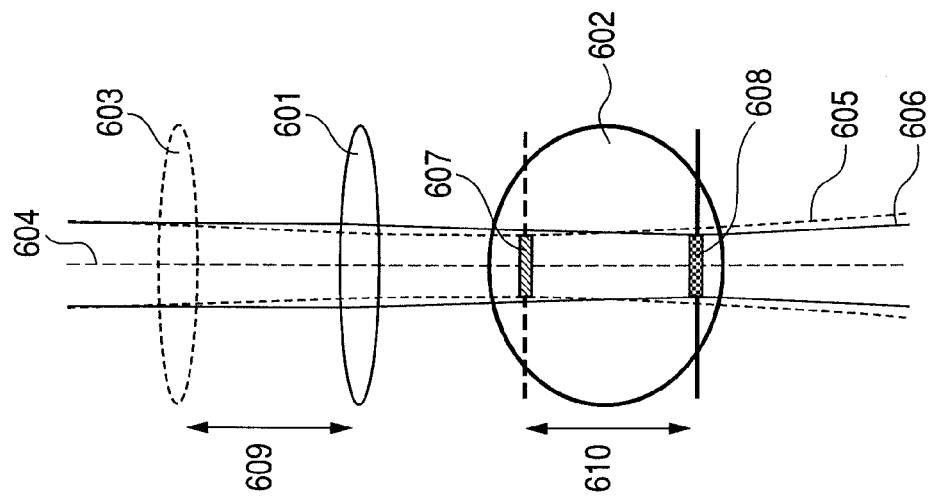

A height of the lateral resolution will be described with reference to FIGS. 6A and 6B. FIG. 6A and FIG. 6B are optically schematic diagrams corresponding to the SD-OCT and TD-OCT, respectively.

First, FIG. 6A will be described. The condensing optical system can move a range of 609 from 601 to 603. Furthermore, when the condensing optical system is in 603, luminous flux 605 whose main light is made 604 which transmits the condensing optical system 603 impinges on the fundus examination object site 602. At this time, reference numeral 607 is a first focus. Furthermore, when the condensing optical system is in 601, luminous flux 606 whose main light is made 604 which transmits the condensing optical system 601 impinges on the fundus examination object site 602. At this time, reference numeral 608 is a second focus. By performing construction as described above, the luminous fluxes 605 and 606 with low NAs can be made in a low lateral resolution and a deep depth of focus 610 like the first and second focuses 607 and 608.

Next, FIG. 6B will be described. The condensing optical system can move a range of 619 from 611 to 613. Furthermore, when the condensing optical system is in 613, luminous flux 615 whose main light is made 614 which transmits the condensing optical system 613 impinges on a fundus examination object site 612. At this time, reference numeral 617 is a first focus. Furthermore, when the condensing optical system is in 611, luminous flux 616 whose main light is made 614 which transmits the condensing optical system 611 impinges on the fundus examination object site 612. At this time, reference numeral 618 is a second focus. Here, each of the luminous fluxes 615 and 616 with high NAs impinges on the site in a high lateral resolution and a shallow depth of focus like the first and second focuses 617 and 618. However, since the condensing optical system is driven according to a depth of an observation site, the deep depth of focus 620 can be achieved.

In this way, in this Example, two kinds of different OCT images are obtained simultaneously. Actions of the central process unit 804 in FIG. 8 are further making a TS-OCT image and a SD-OCT image correspond and re-synthesizing the aligned images by comparing the images in different points of the fundus examination object site.

FIGS. 7B, 7C, and 7D illustrate concept of this alignment schematically. They are arranged images of a tomography image 700 at a plurality of points at the time of a lateral directional scanning in a certain depth, respectively. TD-OCT images 705, 707, and 709 correspond to SD-OCT images 706, 708, and 710, respectively. Although the TS-OCT images 705 and 707 do not have information on a depth direction in itself, there are the SD-OCT images 706 and 708 corresponding to them respectively, and these have the information on the depth direction in FIG. 7B and FIG. 7C. For this reason, by comparing the SD-OCT images and performing a correlation analysis, a positional offset in a certain depth direction between the time of FIG. 7B and the time of FIG. 7C can be corrected. Similarly, correction of FIG. 7C and FIG. 7D is also possible. Here, although an interlayer spacing spreads between FIG. 7B and FIG. 7C, and an interlayer spacing is narrow between FIG. 7C and FIG. 7D, this is corrected to original regular intervals by comparison of the SD-OCT images (e.g., 708 and 710).

Then, reconstruction of a three-dimensional image or reconstruction of a tomography image is performed without a positional offset also in a tomography direction about the TS-OCT images in a high lateral resolution. The reconstructed image is displayed on an image display unit 805.

Thereby, the OCT light interference measuring apparatus which constructs a TS-OCT image with a high lateral resolution without including image deterioration by a tomography-directional positional offset, and displays the TS-OCT image is provided.

In addition, although the central process unit 804 performs the comparison between SD-OCT images automatically in this Example, displaying this on the image display unit 805 and performing this manually can be also performed. In addition, in this Example, in order to reduce volume of data which memory storage of the central process unit 804 stores, the following methods are taken in. That is, as SD-OCT image data of FIG. 7B is eliminated after making interlayer spacing correction between FIG. 7B and FIG. 7C, such a method that position correction by SD-OCT images is performed serially and the SD-OCT data which becomes unnecessary is eliminated is used. Of course, preservation of all the SD-OCT image data is also possible by making the memory storage in large capacity.

(Example of Alignment)

A method of specific alignment between SD-OCT images in this Example will be described with reference to FIGS. 9A to 9C. Of course, the alignment of the present invention is not limited to this method.

First, a method of correcting a positional offset between line images with different z positions in the case of performing scanning in order of x scanning and z scanning and obtaining a two-dimensional x-z tomography image will be described with reference to FIGS. 9A to 9C.

FIG. 9A expresses a three-dimensional image space, and reference 902 is a two-dimensional tomography image of an inspection object 901. In addition, FIG. 9B illustrates a first line image 903 and a second line image 904, which are objects to be aligned, in the two-dimensional tomography image 902. A first alignment point 905 and a second alignment point 906 for alignment which correspond to the same x position are specified in these line images. Let pixel coordinates of the first alignment point 905 be $(0, L)$, let pixel coordinates of the second alignment point 906 be $(0, L+1)$, and a scanning start point at the time of obtaining a line image was selected as an alignment point. Here, let a full scan pixel count in the x direction be Nx, and let pixel coordinates be (x pixel number, z pixel number).

In addition, how to select a position of an alignment point in a scan line is possible otherwise. For example, as illustrated in FIG. 9C, a third alignment point 915 which is an almost center of a third line image can be also selected as (Nx/2, L), and a fourth alignment point 916 which is an almost center of a fourth line image can be also selected as (Nx/2, L+1).

When performing alignment in a scan start position and an end position at the time of obtaining a line image, there is an advantage that scanning speed is slow, image acquisition time becomes long, and an SN ratio of the image becomes high. On the other hand, when performing alignment in a center of a line image, the alignment is performed in a center of the image, and hence, there is an advantage that accuracy of position becomes high by focusing on an image center portion which is paid attention frequently.

Figure 10A:
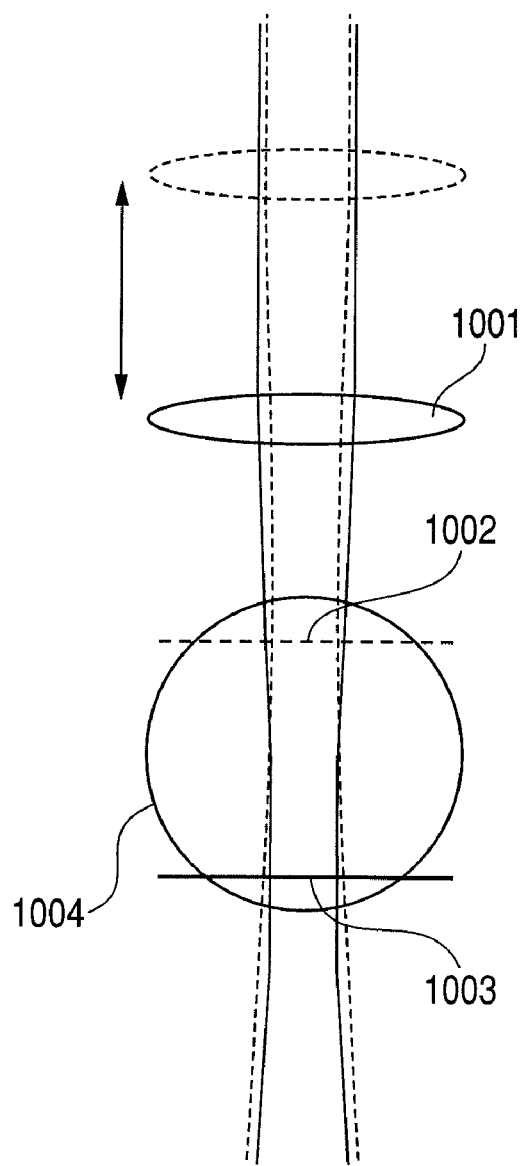
FIGS. 10A and 10B are schematic diagrams illustrating a TD-OCT pixel and an SD-OCT pixel in the second example of the present invention.
Figure 10B:
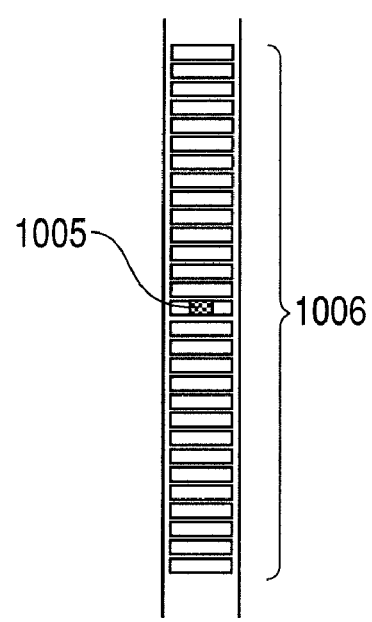

A summary of pixels of an SD-OCT image used for alignment will be described with reference to FIGS. 10A and 10B. FIG. 10A expresses an aspect that the luminous flux which transmits a condensing optical system 1001 impinges on a fundus examination object site 1004 and is condensed through the same optical path. The SD-OCT in this Example is loose because of luminous flux with a low NA, and DOF is widely imaged. This aspect is illustrated by reference numerals 1002 and 1003 in FIGS. 10A and 10B. In addition, a TS-OCT pixel 1005 and an SD-OCT pixel 1006 used for alignment are schematically illustrated in FIG. 10B.

Figure 11A:
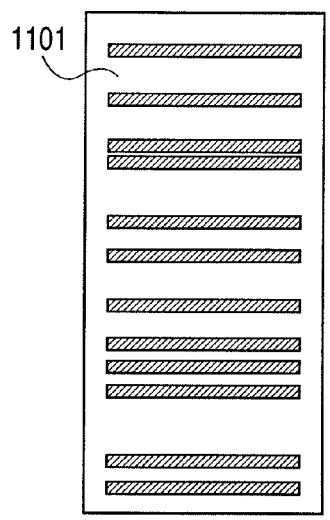
FIGS. 11A, 11B, 11C and 11D are schematic diagrams illustrating SD-OCT images in the second example of the present invention.
Figure 11C:
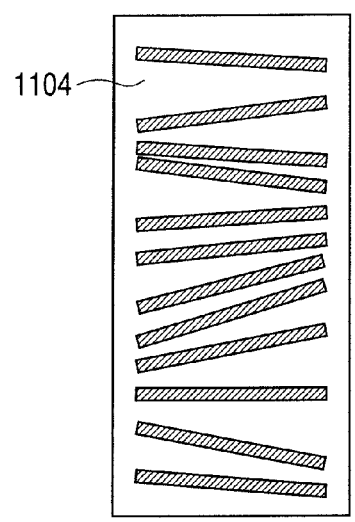
Figure 11B:
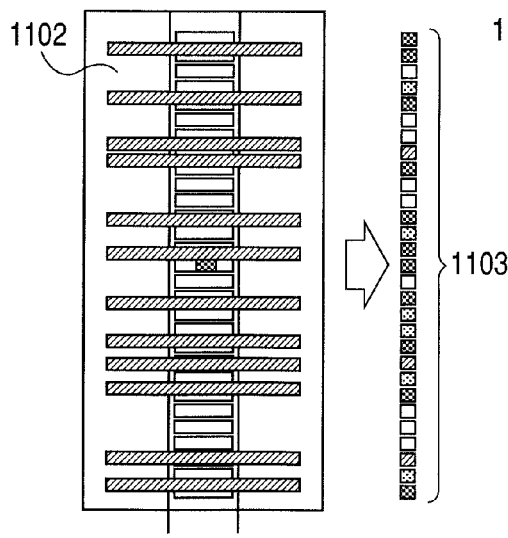
Figure 11D:
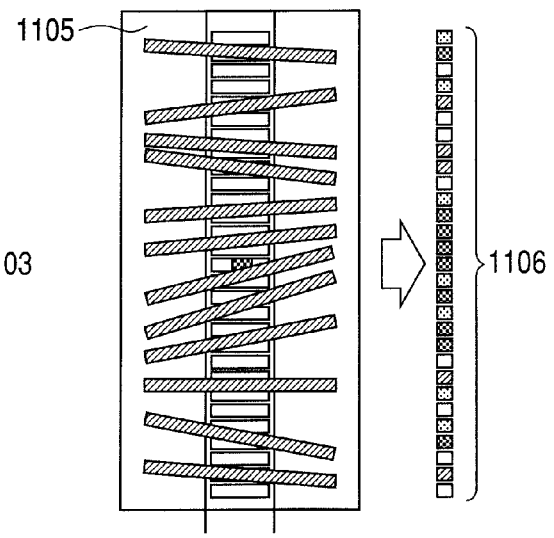

An example of an image pickup target which becomes an object is illustrated in FIG. 11A. What the SD-OCT pixel 1006 in FIG. 10B is superposed on an image pickup target 1101 is reference numeral 1102 in FIG. 11B. Then, a schematic diagram which visualizes signal strength obtained in each pixel is an SD-OCT image 1103. Here, although it is made an image pickup target approximately uniform in a lateral direction (x direction), it may not make an image pickup target approximately uniform in the lateral direction (x direction). For example, as shown in FIG. 11C, let it be an image pickup target 1104 which has elements which incline in the lateral direction (x direction). Here, the SD-OCT pixel 1006 in FIG. 10B superposed on an image pickup target 1104 is reference numeral 1105 in FIG. 10D. Then, a schematic diagram which visualizes signal strength obtained in each pixel is an SD-OCT image 1103.

Figure 12A:
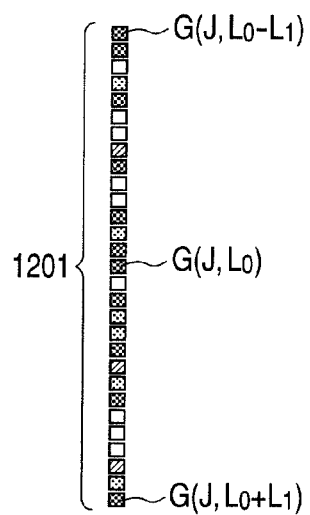
FIGS. 12A, 12B and 12C are schematic diagrams illustrating positional shifts between SD-OCT images in the second example of the present invention.

Next, a method of alignment and a detection method of a positional offset will be described with reference to FIGS. 12A to 12C. Reference numeral 1201 in FIG. 12A is an SD-OCT image including an alignment point of a first line image. Here, G (J, L) expresses image data, and J is an index showing a pixel number in an x direction and L is an index showing a pixel number in a z direction. Let an SD-OCT image center, which is a position of a TS-OCT pixel, be L=$L_0$, and let upward and downward pixels every $L_1$ be obtained.

Figure 12B:
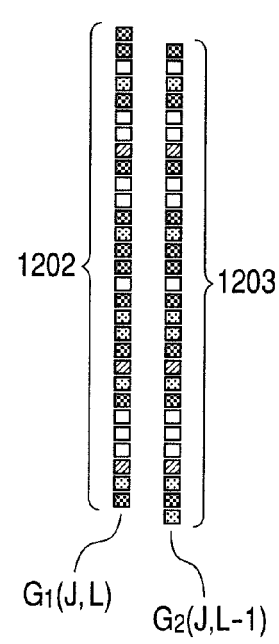
Figure 12C:
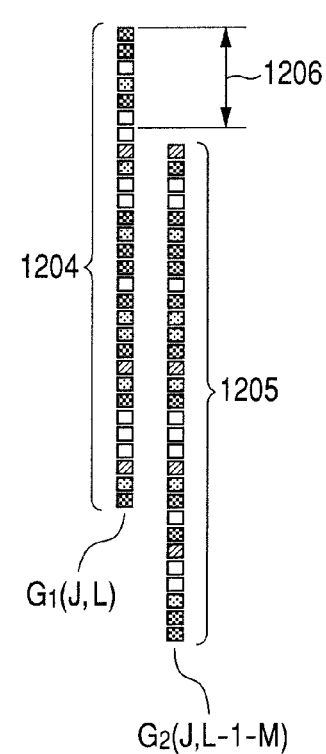

In FIG. 12B, let pixel coordinates of an SD-OCT image 1202, obtained at the alignment point of the first line image, be G1 (J, L). At this time, since pixel coordinates of the SD-OCT image 1203 obtained at the alignment point of the second line image are shifted by 1 pixel in the z direction to the z-coordinate of the SD-OCT image 1202, they become G2 (J, L−1).

When there is no positional offset, G1 (J, L) and G2 (J, L−1) have the same value, but it becomes different values when there is a positional offset. A case where there is a positional offset is illustrated in FIG. 12C. Let a pixel count of a positional offset 1206 be M. In order to evaluate a value of this positional offset, a correlation function was used in this Example. As for the value of the positional offset pixel count M, an optimum positional offset value is found by making M a parameter in the correlation function of G1 (J, L) and G2 (J, L−1−M) and maximizing this. The correlation function is given by the following formula using G1 (J, L), G2 (J, L−1−M), and respective average value.

$$\sum_L \frac{\{G_1(J,L) - \overline{G_1(J,L)}\}}{\sigma_1 \sigma_2} \{G_2(J,L-1-M) - \overline{G_2(J,L-1-M)}\} \quad (I)$$

Here, σ1 and σ2 are standard deviations of G1 and G2, respectively. In addition, a method of maximization can be suitably selected from various kinds of optimization methods, such as a 100 percent inspection and a linear optimization, and the like can be used.

In addition, an evaluation function besides the correlation function may be used. The evaluation function is given by the following formula.

$$\frac{\sqrt{\sum_L \{G_1(J,L) - G_2(J,L-1-M)\}^2}}{N} \quad (II)$$

In addition, when it is necessary to enhance accuracy of alignment, a correlation function, an evaluation function, etc. can be also calculated by making a shift amount by a half or a quarter of a pixel a parameter.

Figure 13A:
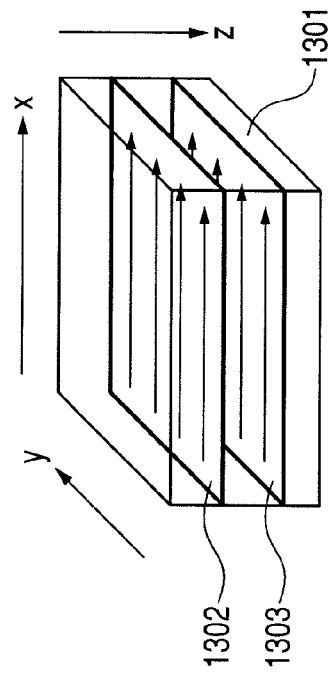
FIGS. 13A, 13B, 13C and 13D are schematic diagrams illustrating alignment points between two-dimensional images in the second example of the present invention.
Figure 13D:
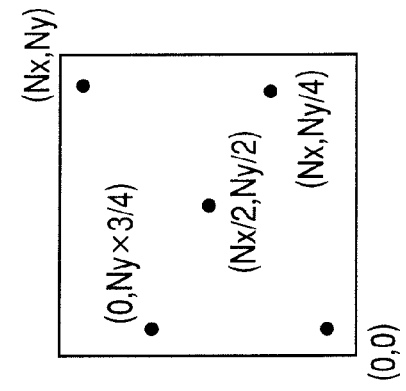

Next, an example of alignment of C-scan images will be described with reference to FIGS. 13A to 13D. Here, a method of correcting a positional offset of C-scan images, whose z positions are different, when performing pitch feed in the z direction after obtaining a two-dimensional x-y image, that is, a so-called C-scan image by x scanning and y scanning, and obtaining a three-dimensional xy-z image 1301 will be described. FIG. 13A expresses a three-dimensional image space, and reference numerals 1302 and 1303 express C-scan images in the inspection object 1301, respectively.

Figure 13C:
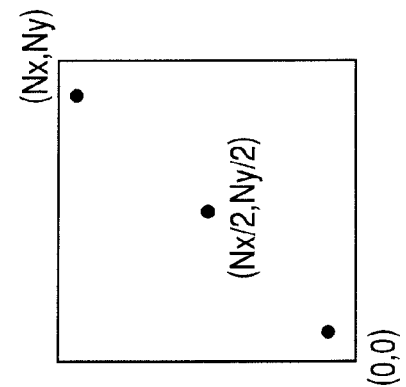
Figure 13B:
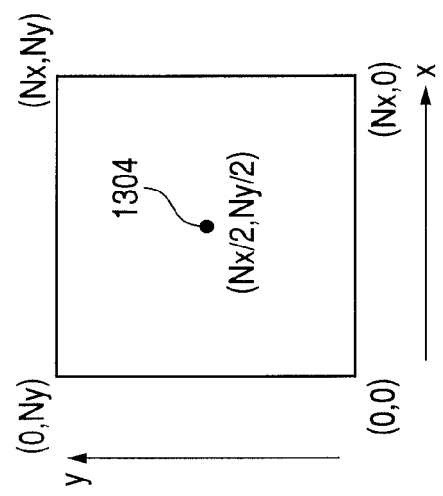

The first C-scan image 1302 or second C-scan image 1303 is illustrated in FIG. 13B. In addition, reference numeral 1304 illustrates an alignment point for alignment. Let a first alignment point in the first C-scan image 1302 be (Nx/2, Ny/2, L), let a second alignment point in the second C-scan image 1303 be (Nx/2, Ny/2, L+1), and a C-scan central point is selected as an alignment point. Here, let a full scan pixel count in an x direction be Nx, let a full scan pixel count in a y direction be Ny, and let pixel coordinates of an alignment point in the C-scan image be (x pixel number, y pixel number, z pixel number).

The same detection method and operation as the example of the alignment of scan lines, which are different in the above-described two-dimensional tomography image, using the SD-OCT image in which depth directional image information of respective alignment points is also obtained at the alignment points specified in this way are performed. Thereby, z-directional alignment of two C-scan images including pitch movement in the z direction is also performed.

In addition, how to select the alignment point in a C-scan image is possible otherwise, and, for example, as illustrated in FIG. 13C, a method of correcting whole C-scan is also possible after averaging positional offsets which are obtained using three points including an x-y scan start position and an x-y scan end position. In addition, as illustrated in FIG. 13C, further increase to five points is also possible. Furthermore, not only translation as a C-scan image, but also correction of skewness of its surface can be also performed by not averaging positional offset amounts of a plurality of alignment points, but by using respective positional offsets for correction of the vicinity of corresponding alignment points.

In the above, predetermined alignment points were determined and alignment was performed using depth-directional SD-OCT images, that is, one-dimensional images in a z direction. However, for example, as illustrated in FIGS. 14A to 14B, a two-dimensional image 1404 in FIG. 14B constructed of SD-OCT images obtained at all the points can be also compared with a two-dimensional image of a two-dimensional image 1414 in FIG. 14C without determining specific alignment points. Hereby, positional shifts can be detected. For example, depth relationship between both images is corrected in consideration of characteristic locations (1405 and 1415) in both images being in the same depth position. Here, FIG. 14A expresses a three-dimensional image space, and reference numeral 1402 expresses a depth-directional two-dimensional image in the inspection object 1401. In such a case, for example, a correlation function of two-dimensional images can be made an evaluation function and can be maximized, and, in that case, various kinds of parameters, such as extension and contraction, besides a whole translation shift can be included as parameters. In addition, a nonlinear optimization technique and other optimization techniques can be used for optimization about a plurality of parameters.

In addition, a method of extracting characteristic points and characteristic structures 1405 and 1415 in a two-dimensional image, and performing alignment based on this is also known widely, and, naturally these can be used. An ICP (Iterative Closest Point) algorithm etc. can be used suitably.

Similarly, about positional offset correction of C-scan images, since a three-dimensional SD-OCT image is obtained per C-scan image, a positional offset is also detectable with comparison of three-dimensional SD-OCT images.

In addition, according to comparison of the above-mentioned two-dimensional images or three-dimensional images, since information with respect to not only a positional offset or extension and contraction in a depth direction (z direction), but also a lateral direction (x direction) can be obtained, it does not matter even if a lateral image shift is corrected.

Other alignment methods may perform alignment with a pixel level of accuracy of the present invention, after performing coarse position corrective feedback by a hardware tracking system for a depth direction. As for the position corrective feedback, it is desirable to control it so as to make it stop when obtaining information on a depth direction. In this case, when calculating a correlation function, a frame-out is performed at an end and a count of pixels which becomes out of calculation objects reduces, and hence, more efficient and highly accurate alignment can be performed.

Example 3

Pupil Division (2)—Different Transmittance

Figure 15:
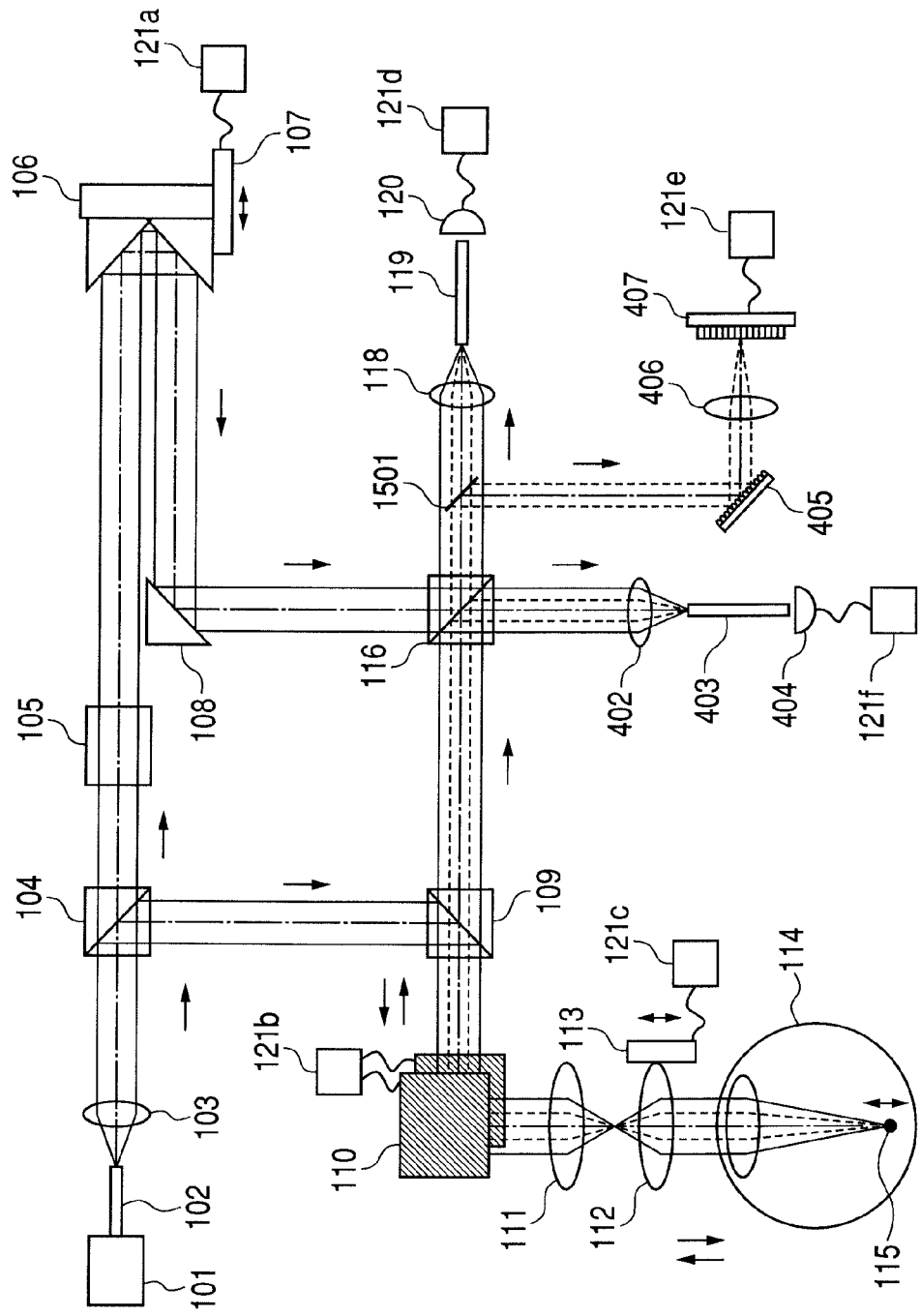
FIG. 15 is a schematic diagram illustrating construction of a light interference measuring apparatus in a third example of the present invention.
Figure 16A:
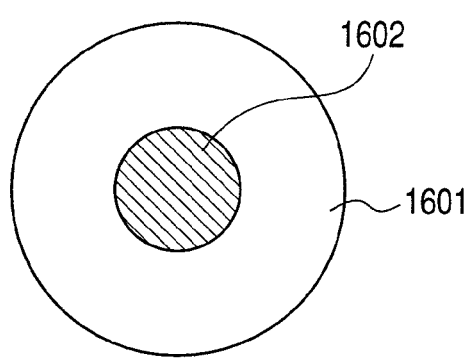
FIGS. 16A, 16B, 16C and 16D are schematic diagrams illustrating construction of a pupil division optical system in the third example of the present invention.

Example 3 will be described with reference to FIGS. 15 to 16D. Here, this embodiment is a modified example of the Example 2. In FIG. 15, construction that the pupil division optical system 401 in FIG. 4 is changed into a pupil division optical system 1501 is illustrated. The other construction in this Example is the same as that in Example 2.

Here, the pupil division optical system 1501 will be described with a schematic diagram in FIGS. 16A to 16D. FIG. 16A shows a pupil division method of this Example, and is constructed of a transparent portion 1601 and a reflection portion 1602. Specifically, as shown in FIG. 16B, a cavity is constructed on a glass substrate and, it is made a transparent portion 1604. In order to support a reflecting film 1605 in a center portion, three beams 1606 are constructed from a periphery. A surface of the center portion is constructed of a reflecting film which is made of chromium being given vapor deposition on a glass substrate, and a reflectance of the reflecting film 204 is constructed in about 90% after about 10% of absorption is subtracted. By the above-mentioned pupil division method and construction, this Example avoids an influence of undesired reflections or absorption in a pupil portion corresponding to a TS-OCT unit, and has construction of a high transmittance. On the other hand, by performing construction of a high reflectance in the pupil portion corresponding to an SD-OCT unit, signal-to-noise ratios are enhanced, respectively. Here, the number of beams is not limited to three.

Figure 16C:
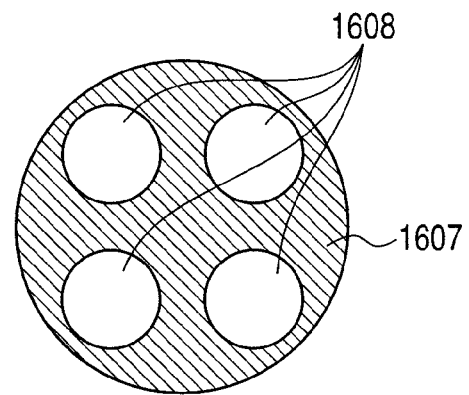
Figure 16B:
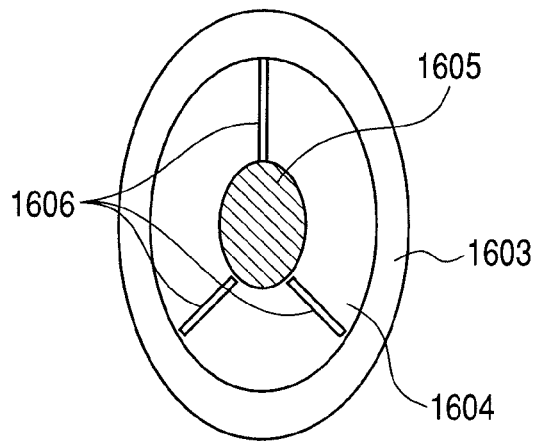
Figure 16D:
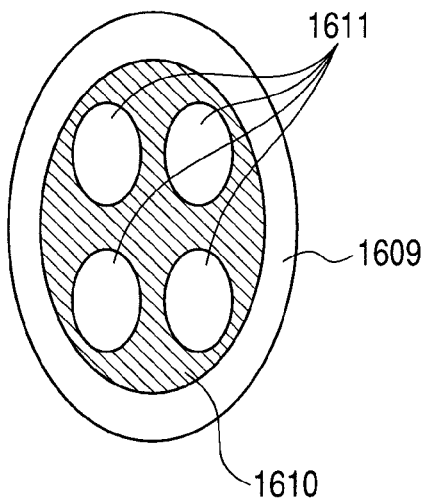

In addition, a method of pupil division can be also made into a quadrupole form as shown in FIG. 16C, etc. In this case, it becomes transparent portions 1608 and a reflection part 1607. Specifically, as illustrated in FIG. 16D, it has construction of cavities 1611 and a reflecting film portion 1610, and hence, construction without using a beam can be performed. In addition, reference numeral 1619 denotes a holding unit.

In addition, as other pupil division methods, there is also a method of changing the pupil division optical system into a simple beam splitter. A whole surface of the beam splitter is constructed without distinguishing a ratio of a transmittance to a reflectance intentionally. Thereby, luminous flux incident on an SD-OCT detection system, that is, the spectroscopic diffraction grating 405, wavelength division imaging lens 406, and line sensor 407 has a high NA similarly to luminous flux incident on a TS-OCT detection system.

Thereby, as for an SD-OCT image for position correction, only a depth-directional center portion has a high lateral resolution, but a depth-directional peripheral portion has a low lateral resolution. Hence, this SD-OCT image has many lateral constituents, and effective position correction is possible to an image pickup target which is constructed in structure with a small inclination. Thereby, position correction, keeping a distribution in a pupil of the TS-OCT uniform can be applied. In addition, the division optical system can be also made into a simple beam splitter.

Example 4

Pupil Division (3)—Polarization

Figure 17:
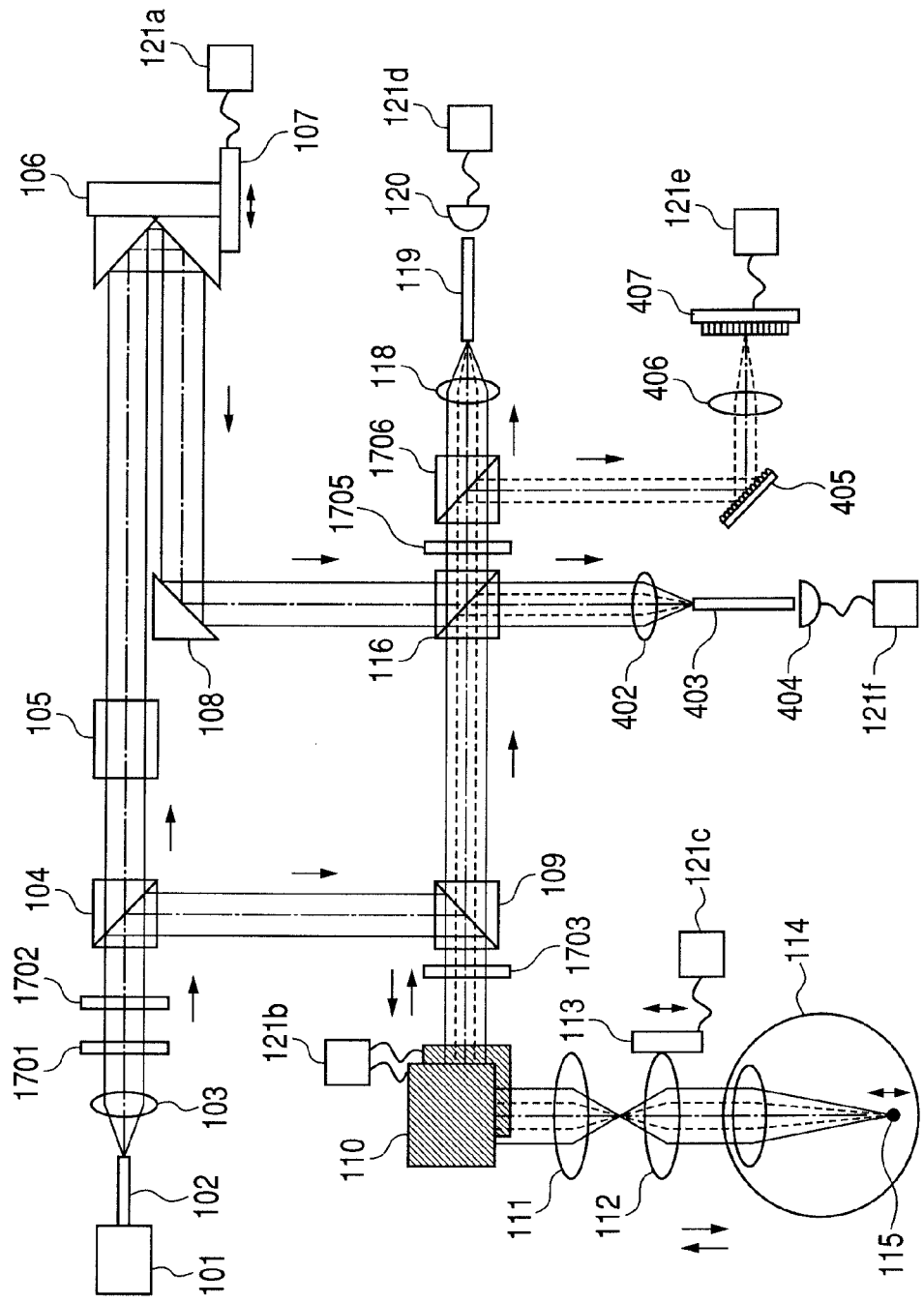
FIG. 17 is a schematic diagram illustrating construction of a light interference measuring apparatus in a fourth example of the present invention.
Figure 18A:
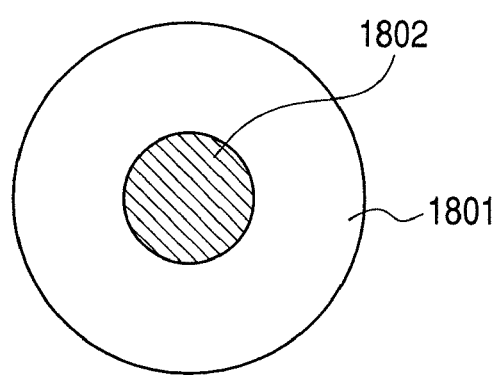
FIGS. 18A, 18B, 18C and 18D are schematic diagrams illustrating construction of a pupil division optical system in the fourth example of the present invention.

Example 4 will be described with reference to FIGS. 17 to 18D. Here, this Example is a modified example of Example 2, and performed pupil division using a polarization characteristic of light.

First, FIG. 17 will be described. Light emitted from the light source 101 is optically guided by the single-mode optical fiber 102, and the light emitted from a fiber edge is converted into parallel light by a collimator lens 103 and propagates in a space. Luminous flux which became linearly polarized light by a polarization specification optical system 1701 became in 45 degrees polarization, that is, a polarization state that p-polarized light and s-polarized light were added in phase by halves by a half wavelength plate 1702, and impinged on the division optical system 104. Here, the division optical system 104 in this Example was constructed of a polarization beam splitter. For this reason, reference light of p-polarized light transmits, signal light of s-polarized light is reflected, and is divided.

Although the reference light is shifted by Δf for its optical frequency by the frequency shifter 105, and, next, it is reflected by the optical delay unit 106, a position of the optical delay unit is controlled by the position driving unit 107 so that an optical path may become a predetermined length. Next, the reference light is guided to the synthesis optical system 116 by the reflection mirror 108.

On the other hand, after impinging on a light guiding division optical system 109, the signal light was guided to the test optical system for the eye 114 and fundus examination object site 115, which were inspection objects, by the division optical system 104. Here, the test optical system is formed by the light guiding division optical system 109, light beam scanning optical system 110, scanning lens 111, and lens 112 for an eye. In addition, the light beam scanning optical system 110 has an action of making main light of the signal light flux incline so as to make it form inclination angles in two orthogonal directions to an optical axis. Thereby, luminous flux which passes the scanning lens 111 and the lens 112 for an eye is given angle scan on a pupil (iris) of an eye. In consequence, it was constructed so that the fundus examination object site 115 might scan an in-plane of a vertical plane (x-y plane) to the optical axis direction (depth direction) on an eyeground because of the optical action of an eye. Here, the light guiding division optical system 109 in this Example is constructed of a polarization beam splitter. For this reason, the signal light which is s-polarized light is reflected toward the inspection object. In addition, in this Example, a quarter wavelength plate 1703 is arranged between the light guiding division optical system 109 and light beam scanning optical system 110, and orientations of a phase-advancing axis and a phase-lagging axis to an optical axis are suitably adjusted so that incident s-polarized light may become circularly polarized light in an inspection object side. Light passing through an approximately same optical path at the time of impinging on the fundus examination object site 115 among reflected light from the fundus examination object site 115, or backscattered light, and proceeding to a direction reverse to incident light is converted to p-polarized light from the circularly polarized light at this time by the quarter wavelength plate 1703 again. Then, it transmits a polarization beam splitter of the light guiding division optical system 109, and it is guided to the synthesis optical system 116.

Next, the reference light and signal light are synthesized by the synthesis optical system 116, and a part of coherent light with the synthetic amplitude added as a complex amplitude impinges on a condensing optical system 118. Then, the luminous flux whose polarization is partially adjusted by a partial area polarization adjustment plate 1705, and transmits a polarization beam splitter 1706 which is a luminous flux division optical system is guided to the condensing optical system 118, single-mode optical fiber 119, and photoelectric conversion detector 120 which are included in a non-spectrum interference signal detection system. In addition, the reflected luminous flux impinges on the spectroscopic diffraction grating 405 which is included in a spectrum interference signal detection system, condenses by the wavelength division imaging lens 406, and is given strength detection every wavelength by the line sensor 407.

On the other hand, a part of coherent light by the synthesis optical system 116 impinges on the condensing optical system 402, is given differential detection with a non-spectrum interference signal through the single-mode optical fiber 403 and photoelectric conversion detector 404, and removes a common mode noise component, and thereafter, is given TS-OCT imaging. In addition, SD-OCT imaging of the spectrum interference signal is performed, and an OCT image with a high lateral resolution which is given position correction suitably and is reconstructed is obtained.

Here, construction of the partial area polarization adjustment plate 1705 will be described with reference to FIGS. 18A to 18D. FIG. 18A is a schematic diagram of the partial area polarization adjustment plate 1705 where a polarization non-adjustable portion 1801 and a half wavelength plate action portion 1802 are constructed of concentric circles. The partial area polarization adjustment plate 1705 in this Example is made by performing surface junction of a transmission region 1804 in an effective diameter set on a glass substrate, and a half wavelength plate 1805, constructed of a circular crystal plate in its center, with the glass substrate, as illustrated in FIG. 18B. An orientation of a phase-advancing axis is set at 45 degrees, and this has an action of rotating a plane of polarization of linearly polarized light by 90 degrees.

Figure 18C:
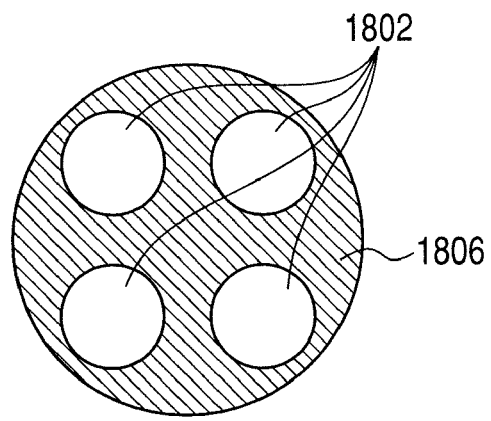
Figure 18B:
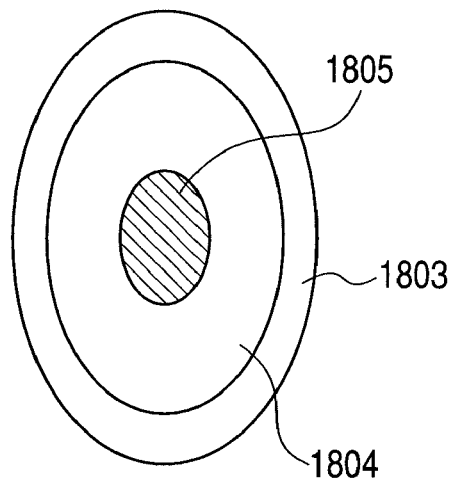
Figure 18D:
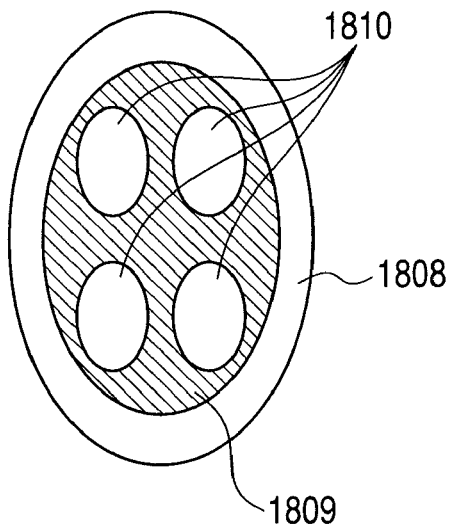

In addition, as shown in FIG. 18C, the polarization non-adjustable portion 1807 can be also constructed in a quadrupole shape. At this time, reference numeral 1806 denotes a half wavelength plate action portion. Specifically, as shown in FIG. 18D, it can be constructed of a holding unit 1808, the half wavelength plate action portion 1809, and the polarization non-adjustable portion 1807.

In addition, although a rotation angle of polarization is made into 90 degrees using a half wavelength plate in this Example, non half wavelength plate may be used, and the rotation angle may be except 90 degrees, and in that case, a ratio of a transmission to a reflection in the polarization beam splitter 1706 which is a luminous flux division optical system can be adjusted suitably.

Example 5

Time Sharing

Figure 19:
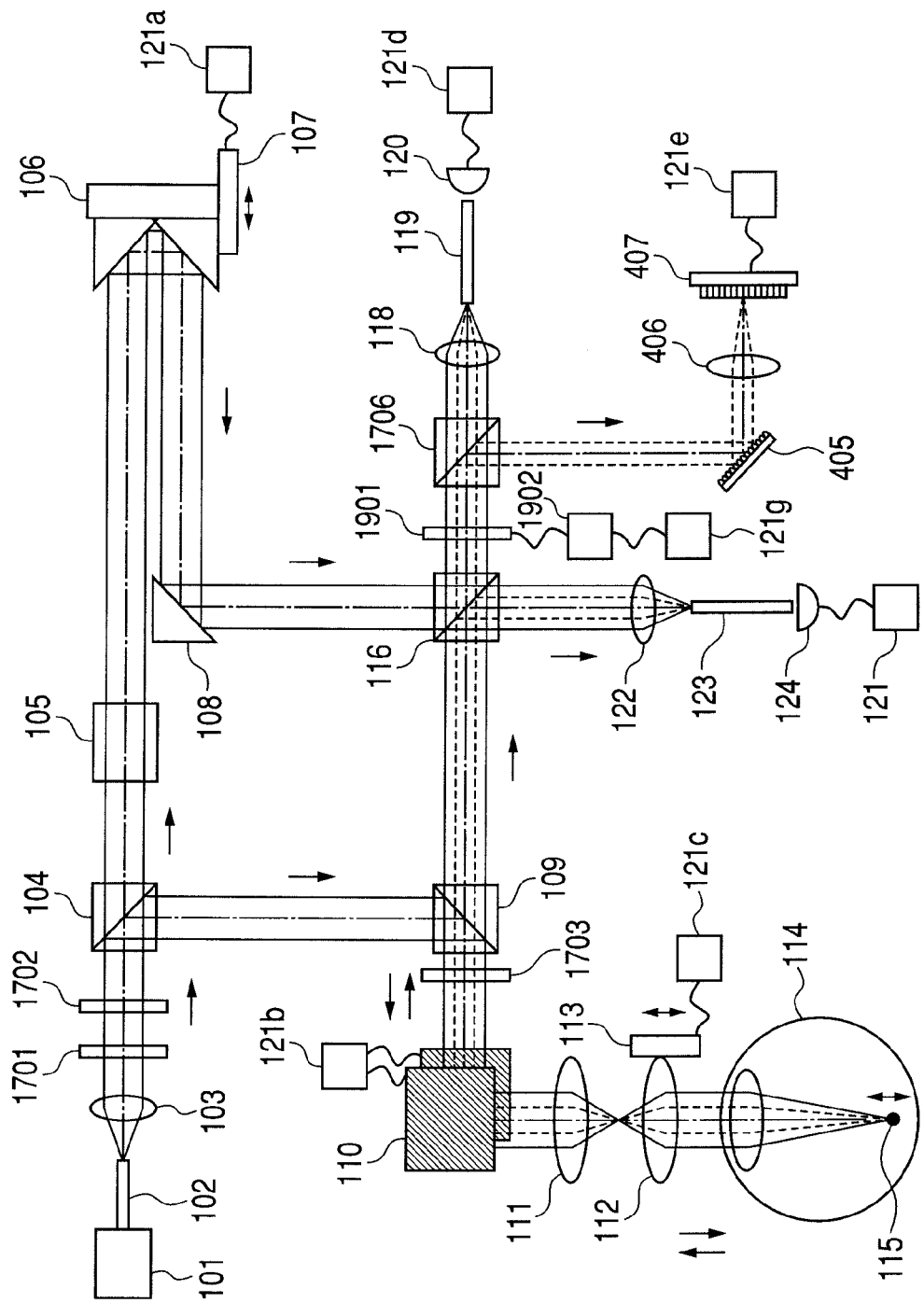
FIG. 19 is a schematic diagram illustrating construction of a light interference measuring apparatus in a fifth example of the present invention.

A fifth example of the present invention will be described with reference to FIG. 19. Here, this example is a modified example of a fourth example, and is an example of performing pupil division in time sharing at high speed. In FIG. 19, construction that the partial area polarization adjustment plate 1705 in FIG. 17 is changed into a spatial polarization modulator 1901 is illustrated. In addition, the spatial polarization modulator 1901 is connected to a modulator driver 1902, and is further connected to the OCT processing apparatus 121g. The other construction in this example is the same as that in the fourth example.

Here, an action of the spatial polarization modulator 1901 is to generate polarization conversion, which is an action of a half wavelength plate, in a predetermined partial area, and to switch this polarization conversion at high speed according to time, in order to perform area division of the luminous flux which passes a pupil. The spatial polarization modulator 1901 is constructed of elements such as a PEM (Photoelastic Modulator) and an EOM (Electro optic modulator), and further, optical elements such as a quarter wavelength plate may be put together and used. The PEM and EOM are devices which modulate a phase and the like of light to transmit them by applying a voltage or an external force to a crystal, and can perform optical modulation at very high speed. When the spatial polarization modulator 1901 is operated, a polarization state of a part of transmitted light changes, and a reflectance in the polarization beam splitter 1706 changes. For example, an SD-OCT image can be obtained by making polarization of a partial area into s-polarized light by operating the spatial polarization modulator 1901, and making it reflect to the spectroscopic diffraction grating 405 from the polarization beam splitter 1706. When stopping an operation of the spatial polarization modulator 1901, a large portion of luminous flux can transmit the polarization beam splitter 1706, and a highly sensitive TS-OCT image can be obtained.

Here, the OCT processing apparatus 121g controls the modulator driver 1902 according to a processing mode controlled internally, and switches the spatial polarization modulator 1901. In this example, it switched presence of the polarization conversion by turns every approximately microsecond. Timing charts at this time are illustrated in FIGS. 42A to 42F:

FIG. 42A: OCT processing apparatus 121 controls a TS-OCT obtaining mode and an SD-OCT obtaining mode internally; FIG. 42B: The OCT processing apparatus 121 makes the spatial polarization modulator 1901 act through the modulator driver 1902 in the SD-OCT obtaining mode; FIG. 42D: Here, at the time of the TS-OCT mode, a signal of TS-OCT is obtained by a 120 photoelectric conversion detector; FIG. 42E: a signal of SD-OCT is obtained by 407 line sensors at the time of the SD-OCT mode.

Thereby, non-spectral interference signal detection which generates TS-OCT information, and spectral interference signal detection which generates SD-OCT in FIG. 42F, as pixel data, data of TS-OCT and SD-OCT are obtained by turns. Time to finish measuring TS-OCT and SD-OCT data of one pixel is 2 microseconds in this example.

Thereby, the luminous flux division of a pupil in time sharing can be performed, and an OCT image can be obtained without losing the luminous flux in a partial area from all the pupils also in TS-OCT. Furthermore, by an SD-OCT image which can be regarded to be obtained approximately simultaneously, position correction can be performed.

In addition, although light division is performed using the spatial polarization modulator 1901 and polarization beam splitter 1706 in this example, high-speed light control can be performed without using the spatial polarization modulator 1901 or the polarization beam splitter 1706 by using an optical switching element using a MEMS (Micro Electro Mechanical Systems) technique and the like.

In addition, as described up to now, a frequency shifter is used in many cases in the TD-OCT as shown in FIG. 19. This is for performing heterodyne detection which makes a frequency difference Δf carrier frequency by giving the frequency difference Δf between the reference light and signal light using the frequency shifter. An interference signal at the time of TD-OCT measurement is measured as a time series change of the amplitude absolute value of the frequency Δf, and an influence of a noise signal with the other frequency can be excluded. On the other hand, in the SD-OCT, by dispersing light, synthesized by the polarization beam splitter 1706, by the spectroscopic diffraction grating 405 to detect a light intensity, and performing Fourier transformation of this spectrum interference streak, information on a depth direction is obtained. For this reason, it is necessary in SD-OCT to detect light in all the wavelength, and detection by limiting a wavelength or a frequency is not performed. Therefore, it is not necessary in SD-OCT to give the frequency difference Δf between the reference light and signal light by the frequency shifter 105, and further, by stopping the frequency shifter 105, mixing of an unnecessary signal is excluded and a more accurate SD-OCT signal can be taken. Therefore, construction of starting and stopping the frequency shifter 105 by performing approximate synchronization with polarization conversion is more desirable. In this case, as illustrated in FIG. 42C, a 105 frequency shifter is controlled according to an operation mode inside the OCT processing apparatus 121, becomes on at the time of the TS-OCT obtaining mode, and becomes off at the time of the SD-OCT obtaining mode.

Example 6

Luminous Flux Limitation Unit

An Example 6 of the present invention will be described with reference to FIG. 20. Here, this Example is a modified example of Example 4, and a luminous flux limitation unit is newly added to the construction.

Figure 20:
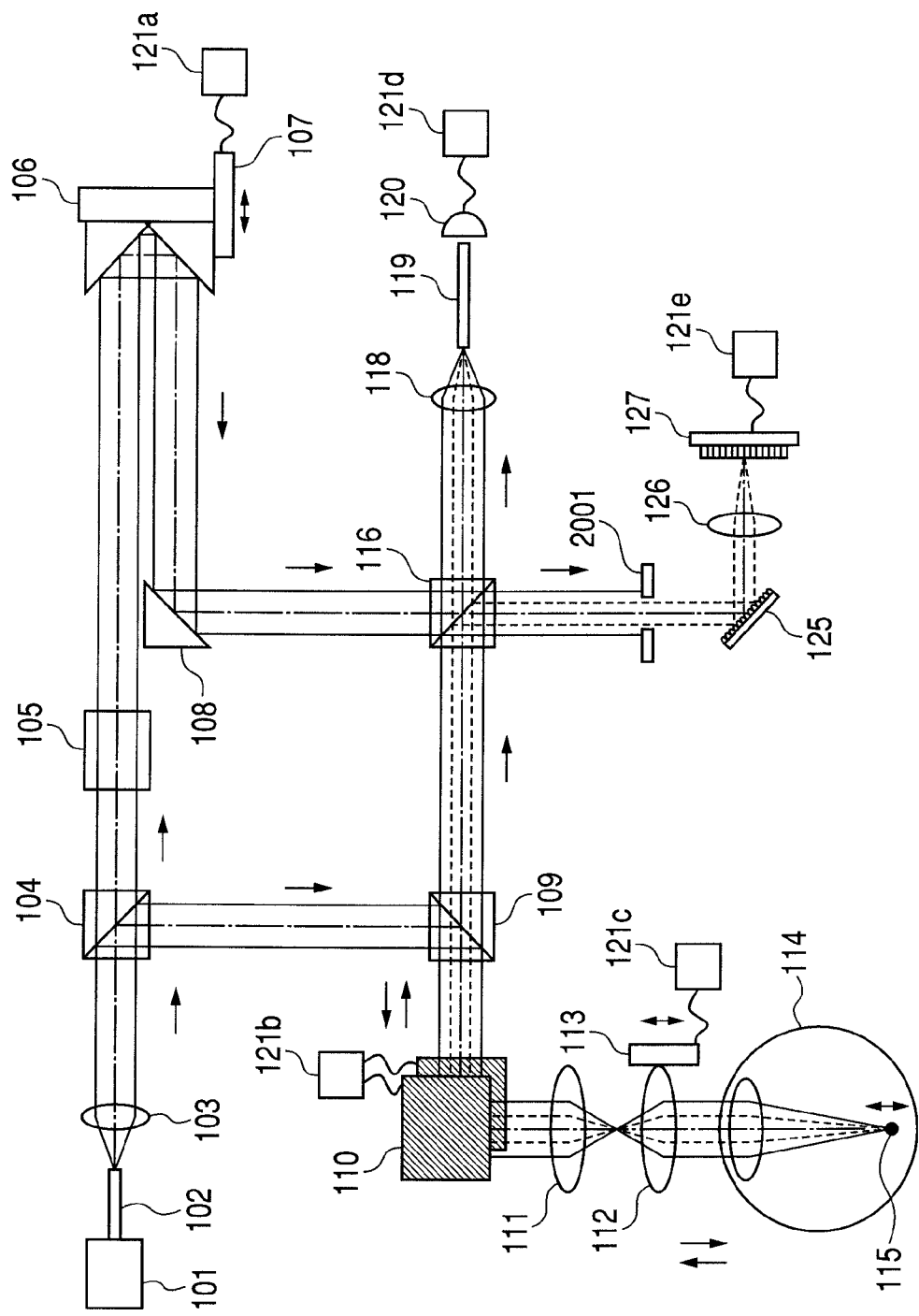
FIG. 20 is a schematic diagram illustrating construction of a light interference measuring apparatus in a sixth example of the present invention.

In FIG. 20, the luminous flux limitation unit 2001 as a stop was arranged in an optical path which arrived at the spectroscopic diffraction grating 125 for spectral interference signal detection, the wavelength division imaging lens 126, and the line sensor 127. An action of the luminous flux limitation unit 2001 is to make only a center portion of luminous flux selectively transmit and to block the remainder in order that a deep depth of focus may be obtained. Thereby, the SD-OCT image detected by the OCT processing unit 121e through spectral interference signal detection becomes an image with a deep depth of focus. For this reason, accuracy of position correction in a depth direction can be increased.

Example 7

This Example will be described with reference to FIGS. 21A to 21C and 22A, 22B. Here, this Example is an example applicable to other Examples of the present invention.

Figure 21A:
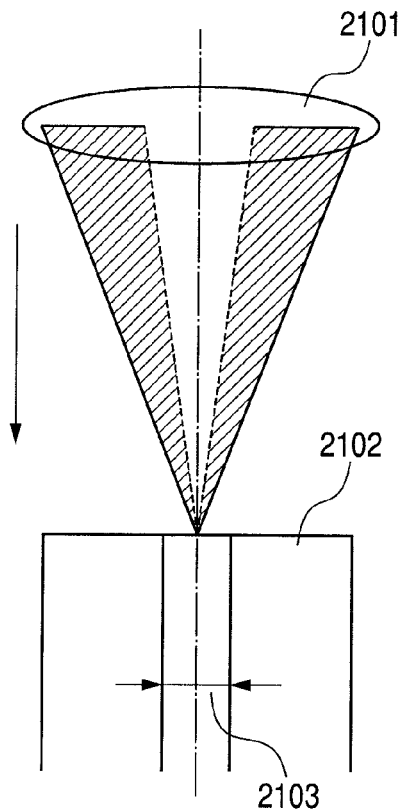
FIGS. 21A, 21B and 21C are a schematic diagram and graphs describing outlines of optical modes in a seventh example of the present invention.
Figure 21B:
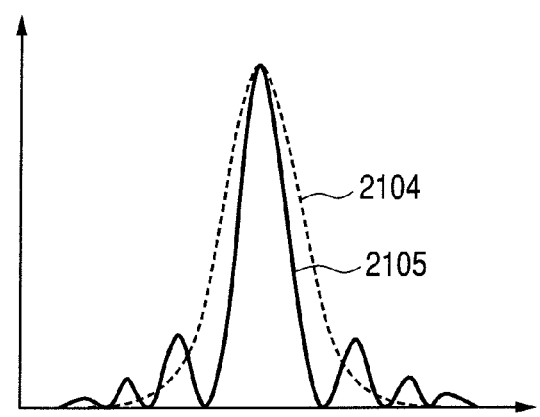
Figure 21C:
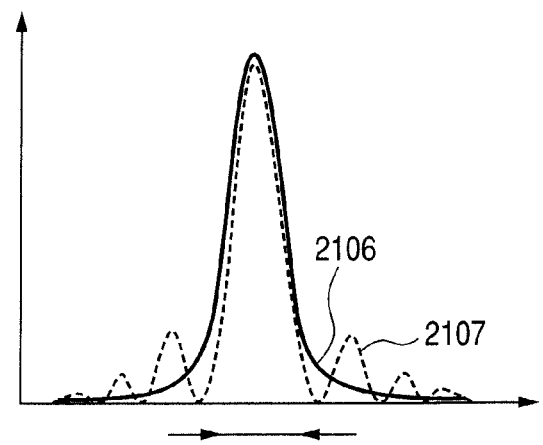

FIGS. 21A to 21C are diagrams illustrating schematically optical spatial mode in an optical fiber 2102 from a condenser lens 2101. In other Examples in the present invention, luminous flux incident on a condenser lens is divided for a center portion and its light quantity is decreased. That is, light quantity of ambient luminous flux is increased. A light intensity distribution in a fiber incident end at the time of condensing such luminous flux by a lens becomes a distribution 2105 with a plurality of large sub peaks although width of a main peak is narrow in comparison with an original fundamental mode 2104. Then, a mode field diameter 2103 of an optical fiber is made to be suitable for the main peak of the distribution 2105. Thereby, the main peaks of an optical fiber propagation mode distribution 2106 and a distribution 2107 overlap, and luminous flux which has a component with a high spatial resolution is guided more efficiently to a detector.

FIGS. 22A and 22B are schematic diagrams illustrating an example of a mode conversion optical system 2205 for guiding a component with such a high spatial resolution to a detector further efficiently. Luminous flux which has a distribution 2202 is converted into luminous flux nearer to a fundamental mode of a Gaussian distribution by a cone prism 2203 and is converted into an optical mode in which an approximate Gaussian distribution 2207 is condensed by a condenser lens 2204, and thereafter, it impinges on the optical fiber 2102. Instead of the cone prism 2203 and condenser lens 2204, a regular interval concentric circle diffraction grating 2209 and a non-regular interval concentric circle diffraction grating 2210 which are etched into both faces on a quartz substrate 2208 by lithography are constructed and can be made to have the same optical mode converting operation. As mentioned above, a component with a high resolution is detected efficiently and a TS-OCT image can be formed.

In addition, when it is desirable to construct an optical mode with a high resolution by the luminous flux for which the pupil division adjustment was performed, a pupil division optical system can be suitably put in between a synthesis optical system and a condenser lens, and an optical mode can be adjusted.

Example 8

Optical Fiber

Figure 23:
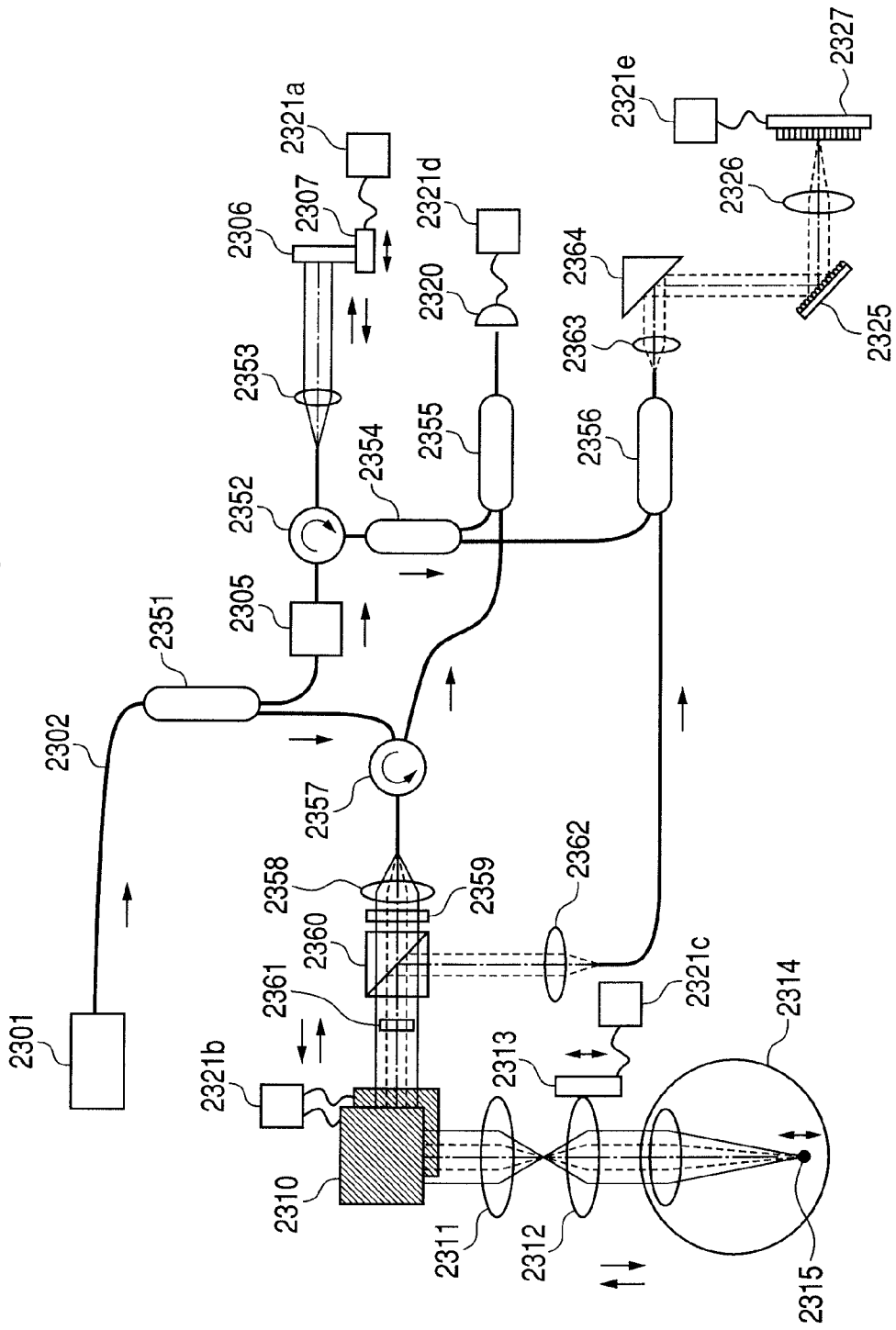
FIG. 23 is a schematic diagram illustrating construction of a light interference measuring apparatus in an eighth example of the present invention.

An Example 8 of the present invention will be described with reference to FIG. 23. Here, this embodiment is a modified example of the Example 1, and an optical fiber was used.

Light emitted from a light source 2301 is optically guided by a single-mode optical fiber 2302, and is divided into reference light and signal light by a division optical system 2351 for a fiber.

As for reference light, its optical frequency is shifted by the frequency shifter 2305 by Δf. Next, after passing an optical circulator 2352, it becomes approximately parallel light by a collimator 2353, and is reflected by an optical delay unit 2306. Here, a position of the optical delay unit is controlled by a position driving unit 2307 so that an optical path may become a predetermined length. Next, the reference light returns to the optical fiber by the collimator 2353, and is sent to synthesis optical systems 2355 and 2356 for a fiber by the optical circulator 2352 by the division optical system 2354 for a fiber, respectively.

The signal light passes an optical circulator 2357 by the division optical system 2351, impinges on a collimator 2358, and becomes parallel light. After that, it is converted into p-polarized light by a half wavelength plate 2359, transmits a polarization beam splitter 2360, and passes a partial area quarter wavelength plate 2361. After the passing concerned, it goes to and from a test optical system formed to an eye 2314 and a fundus examination object site 2315, which are inspection objects, by a light beam scanning optical system 2310, a scanning lens 2311, and a lens 2312 for an eye. Here, a light beam scanning optical system 2310 has an action of making main light of the signal light flux incline so as to make it form inclination angles in two orthogonal directions to an optical axis. Thereby, luminous flux which passes the scanning lens 2311 and the lens 2312 for an eye is given angle scan on a pupil (iris) of an eye. In consequence, it was constructed so that the fundus examination object site 2315 might scan an in-plane of a vertical plane (x-y plane) to the optical axis on an eyeground because of the optical action of an eye.

Light passing through an approximately same optical path at the time of impinging on the fundus examination object site 2315 among reflected light from the fundus examination object site 2315, or back-scattered light, and proceeding to a direction reverse to incident light is polarized by the partial area quarter wavelength plate 2361. Specifically, only a center portion which is a predetermined part is converted into polarized light rotated by 90 degrees from that at the time of incidence by a forward and backward optical action of the wavelength plate. Thereby, in a polarization beam splitter, a center portion of luminous flux is reflected, and peripheral portion of luminous flux transmits and returns the original optical path.

The transmitted peripheral portion of luminous flux is condensed by the collimator 2358, returns to the fiber, and is sent to the synthesis optical system 2355 by the optical circulator 2357. On the other hand, the reflected center portion of luminous flux is condensed by a condenser lens 2362, impinges on the fiber, and is sent to the synthesis optical system 2356. Respective luminous fluxes are multiplexed with the reference light by the synthesis optical systems 2355 and 2356, and a non-spectral interference signal is detected by a photoelectric conversion detector 2320. On the other hand, a spectral interference signal is detected by a spectroscopic diffraction grating 2325, a wavelength division imaging lens 2326, and a line sensor 2327. They are sent to an OCT processing unit 2321 is visualized as a TS-OCT image and a SD-OCT image respectively, and is suitably processed.

A position driving unit 2307, the light beam scanning optical system 2310, a focusing position driving unit 2313, the photoelectric conversion detector 2320, and the line sensor 2327 perform drive and the like by inputs and outputs by the following apparatuses. That is, drive and detection are performed with inputs and outputs by OCT processing apparatuses 2321a, 2321b, 2321c, 2321d, and 2321e.

Example 9

Correction of SD by SD (1)—One Apparatus

Figure 24:
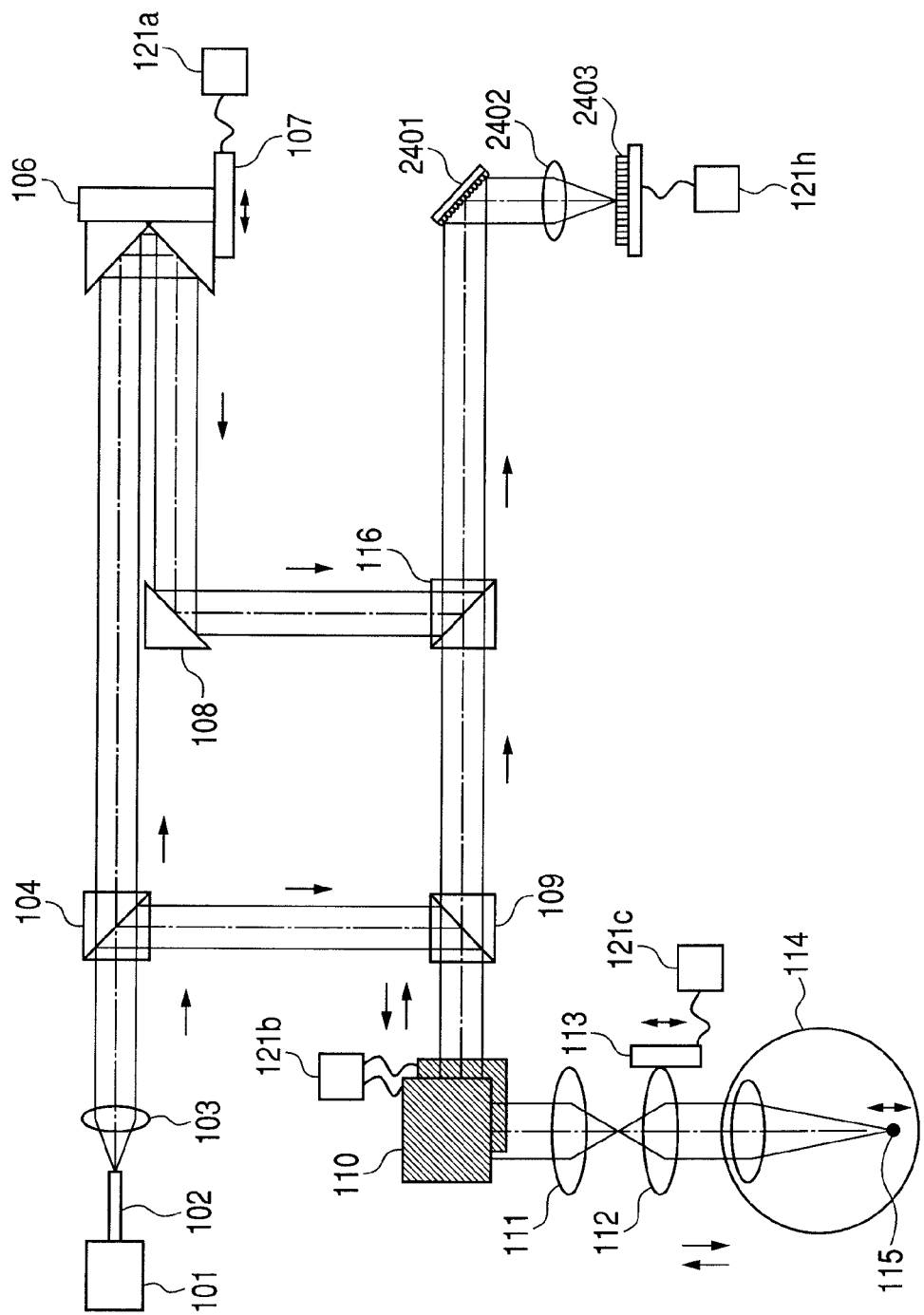
FIG. 24 is a schematic diagram illustrating construction of a light interference measuring apparatus in a ninth example of the present invention.

An Example 9 of the present invention will be described with reference to FIG. 24. Here, this Example specified the Embodiment 2 and performed image pickup of SD-OCT using an imaging system with a high NA, and DF. An SD-OCT image obtained in a high NA is divided into central pixels which have a high lateral resolution, and peripheral pixels for alignment with a low lateral resolution in a depth direction, and correction for alignment was performed.

First, light emitted from the light source 101 is optically guided by the single-mode optical fiber 102, and the light emitted from a fiber edge is converted into parallel light by the collimator lens 103 to be divided into reference light and signal light by the division optical system 104.

The reference light is reflected by the optical delay unit 106, and is next guided to the synthesis optical system 116 by the reflection mirror 108.

After impinging on a light guiding division optical system 109, the signal light is guided to a test optical system for an eye 114 and a fundus examination object site 115 which are inspection objects. Here, the test optical system is formed by the light guiding division optical system 109, a light beam scanning optical system 110, a scanning lens 111, and a lens 112 for an eye. The lens 112 for an eye is driven to the optical axis direction of incident light by the focusing position driving unit 113. In addition, the light beam scanning optical system 110 has an action of making main light of the signal light flux incline so as to make it form inclination angles in two orthogonal directions to an optical axis. Thereby, luminous flux which passes the scanning lens 111 and the lens 112 for an eye is given angle scan on a pupil (iris) of an eye. In consequence, it was constructed so as to scan an in-plane of a vertical plane (x-y plane) to the optical axis direction (depth direction) on an eyeground in the fundus examination object site 115 because of an optical action of an eye. A part of light passing through an approximately same optical path at the time of impinging on the fundus examination object site 115 among reflected light from the fundus examination object site 115, or back-scattered light, and proceeding to a direction reverse to incident light is guided to the synthesis optical system 116 by the light guiding division optical system 109.

Next, the reference light and signal light are synthesized by the synthesis optical system 116, and coherent light with the synthetic amplitude added as a complex amplitude impinges on a spectroscopic diffraction grating 2401. Then, it is condensed by a wavelength division imaging lens 2402, is given strength detection every wavelength by a line sensor 2403, and is sent to an OCT processing unit 121h in order to obtain an SD-OCT image.

Only the pixels with a high lateral resolution which can be obtained by a focus mechanism constructed by the lens 112 for an eye, and the focusing position driving unit 113 are used as final image components. In addition, pixels obtained simultaneous in addition to them are used for alignment.

Next, alignment of this Example will be described. As to relationship with alignment points and alignment images which are used for this alignment, FIGS. 9 to 13D which are described in the examples of the alignment of the second example can be used.

A summary of an SD-OCT pixel for alignment obtained in an alignment point is illustrated in FIGS. 25A and 25B. FIG. 25A expresses an aspect that the luminous flux which transmits a condensing optical system 2501 impinges on a fundus examination object site 2502 and is condensed through the same optical path. The SD-OCT in this Example is sharp because of luminous flux with a high NA, and DOF is narrowly imaged. In addition, an SD-OCT pixel 2503, which is an alignment point, and an SD-OCT pixels 2504 and 2506 above and below it which are used for alignment are schematically illustrated in FIG. 25B.

Figure 26A:
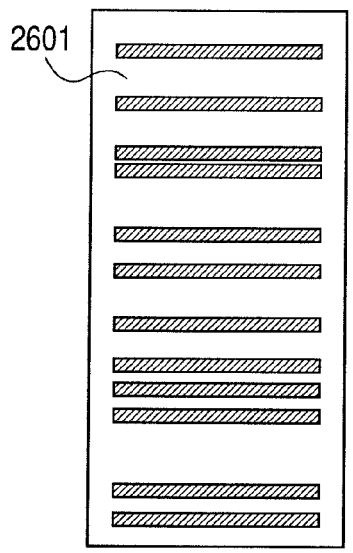
FIGS. 26A, 26B, 26C and 26D are schematic diagrams illustrating SD-OCT images in the ninth example of the present invention.

An example of an image pickup target which becomes an object is illustrated in FIG. 26A. The SD-OCT pixels 2503, 2504, and 2505 in FIG. 25B superposed on an image pickup target 2601 is reference numeral 2602 in FIG. 26B. Then, a schematic diagram which visualizes signal strength obtained in each pixel is an SD-OCT image 2603. Here, it was made an image pickup target approximately uniform in a lateral direction (x direction). In such an image pickup target, as schematically illustrated in the SD-OCT image 2603, it is well resolved in the depth direction (z direction). A specific example of alignment can be performed similarly to what is illustrated in the second example.

Figure 26C:
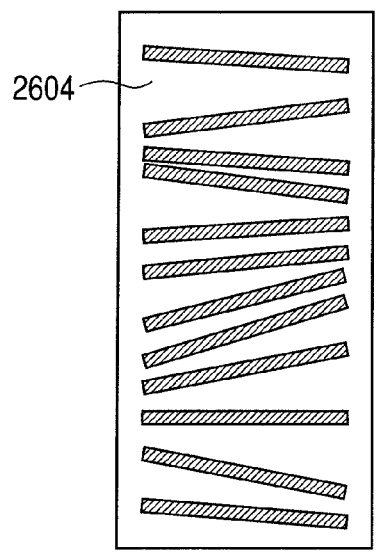
Figure 26B:
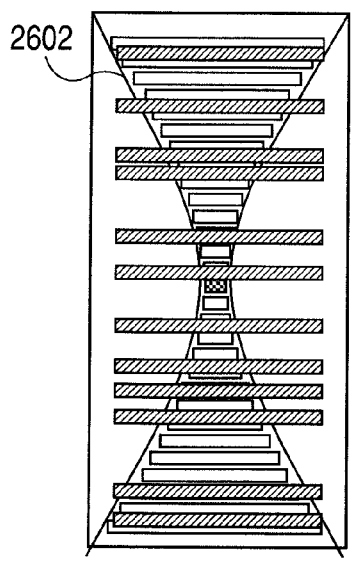
Figure 26D:
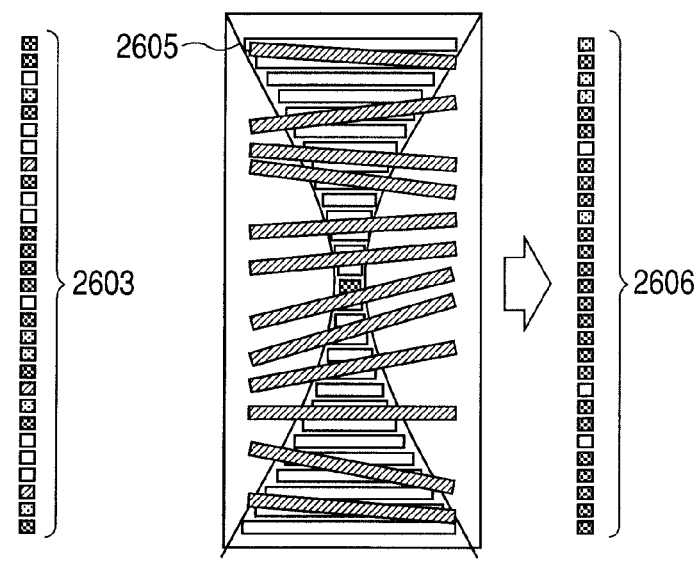

Next, a case where it is not an image pickup target approximately uniform in the lateral direction (x direction) will be described. For example, as shown in FIG. 26C, let it be an image pickup target 2604 which has elements which incline in the lateral direction (x direction). Here, the SD-OCT pixels 2503, 2504, and 2505 in FIG. 25B superposed on the image pickup target 2604 is reference numeral 2605 in FIG. 26D. When an inclination is sharp in comparison with a lateral resolution of an SD-OCT pixel, since it is no longer resolved in a depth direction (z direction) as illustrated in an SD-OCT image 2606, it becomes hard to use this for the alignment in the depth direction. Therefore, this example is suitable for an image pickup target which has many lateral (x direction) constituents and is constructed in structure with a small inclination.

Thereby, by dividing an SD-OCT image into pixels with a high resolution in a center portion of its image pickup depth, and pixels for alignment in a peripheral portion of the image pickup depth, and using them, an image whose position is corrected and which has a high lateral resolution can be obtained by only one SD-OCT measurement system. Nevertheless, since the image information for one dimension is not used as an image even if it is SD-OCT, the same scanning as TS-OCT is necessary.

Example 10

Correction of SD by SD (2)—Two Apparatuses

Figure 27:
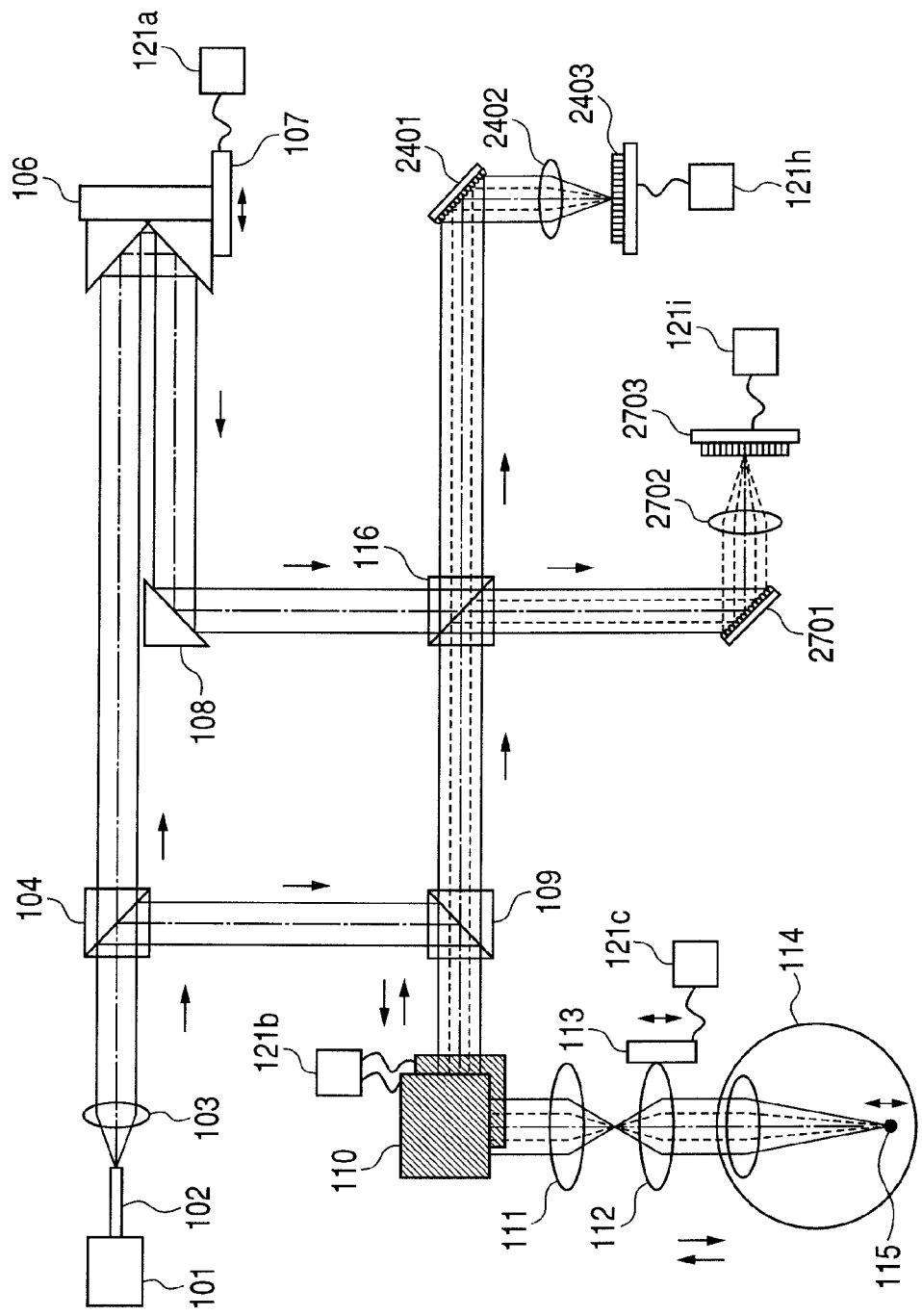
FIG. 27 is a schematic diagram illustrating construction of a light interference measuring apparatus in a tenth example of the present invention.

Example 10 will be described with reference to FIG. 27. Here, this Example is a modified example of the Example 9, and a spectroscopic diffraction grating 2701, a wavelength division imaging lens 2702, a line sensor 2703, and an OCT processing unit 121i were newly added to the construction. Thereby, besides the SD-OCT image processing unit with a high resolution, images for alignment can be acquired.

Here, in this Example, an image equivalent to one scan line of an A-scan (scanning in a depth direction) is always acquirable by batch in the SD-OCT image processing with a high resolution. However, since only one focused pixel portion is used in an image equivalent to one scan line, it is desirable to remove the image in a depth direction except it.

Figure 28:
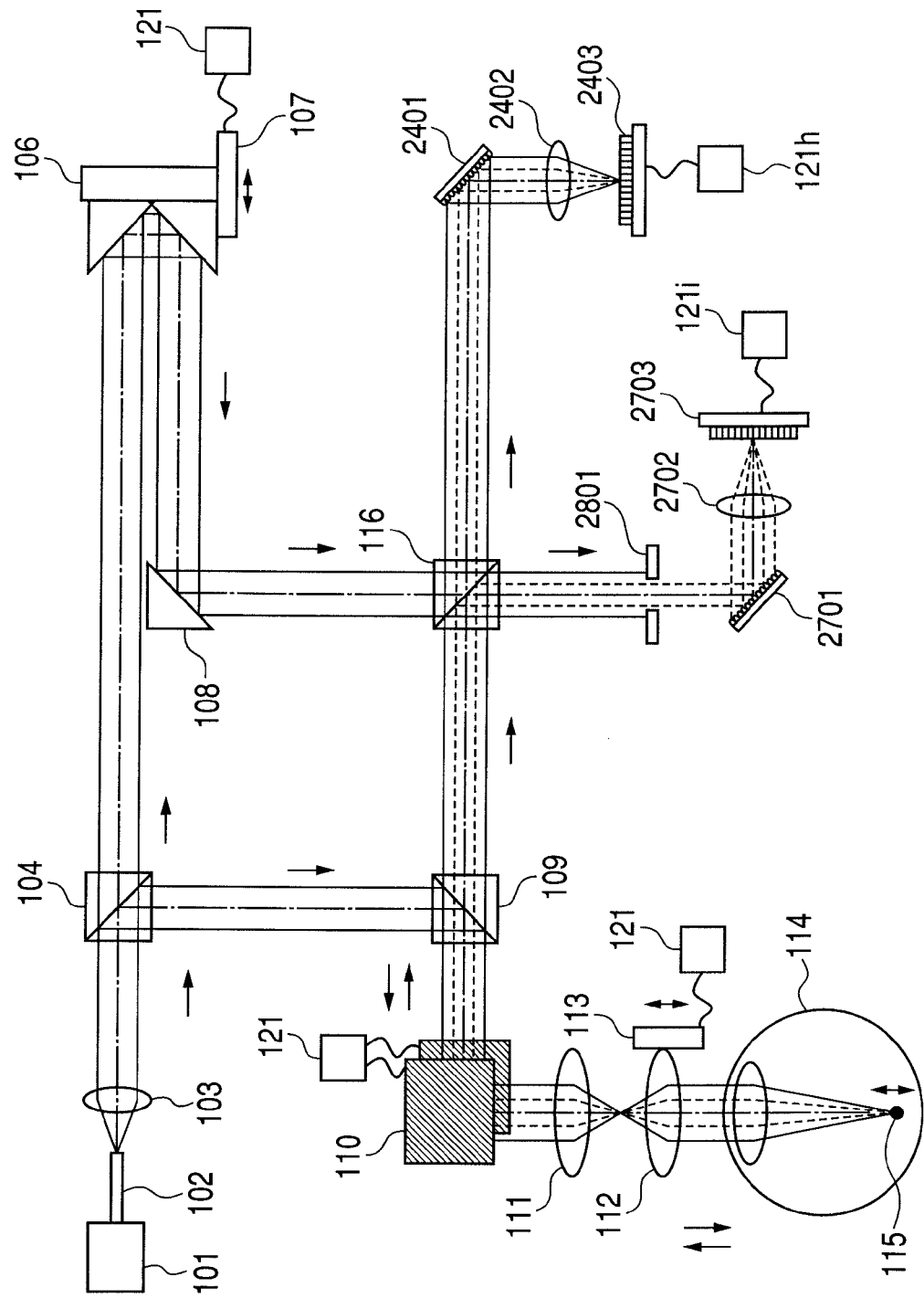
FIG. 28 is a schematic diagram illustrating a modified example in the tenth example of the present invention.

In addition, as a further modified example of the Example, there is also a method of newly adding the luminous flux limitation unit to the construction as shown in FIG. 28.

A luminous flux limitation unit 2801 as a stop was arranged in an optical path which arrived at a spectroscopic diffraction grating 2701, a wavelength division imaging lens 2702, and a line sensor 2703. An action of the luminous flux limitation unit 2801 is to make only a center portion of luminous flux selectively transmit and to block the remainder in order that a deep depth of focus may be obtained. Thereby, the SD-OCT image detected by the OCT processing unit 121i through spectral interference signal detection becomes an image with a deep depth of focus. For this reason, accuracy of position correction in a depth direction can be increased.

In addition, an optical delay unit may be driven in synchronization with a focus driving apparatus. By this construction, an image pickup center portion in a depth direction can be specified.

Example 11

Correction of TD by SS

Figure 36:
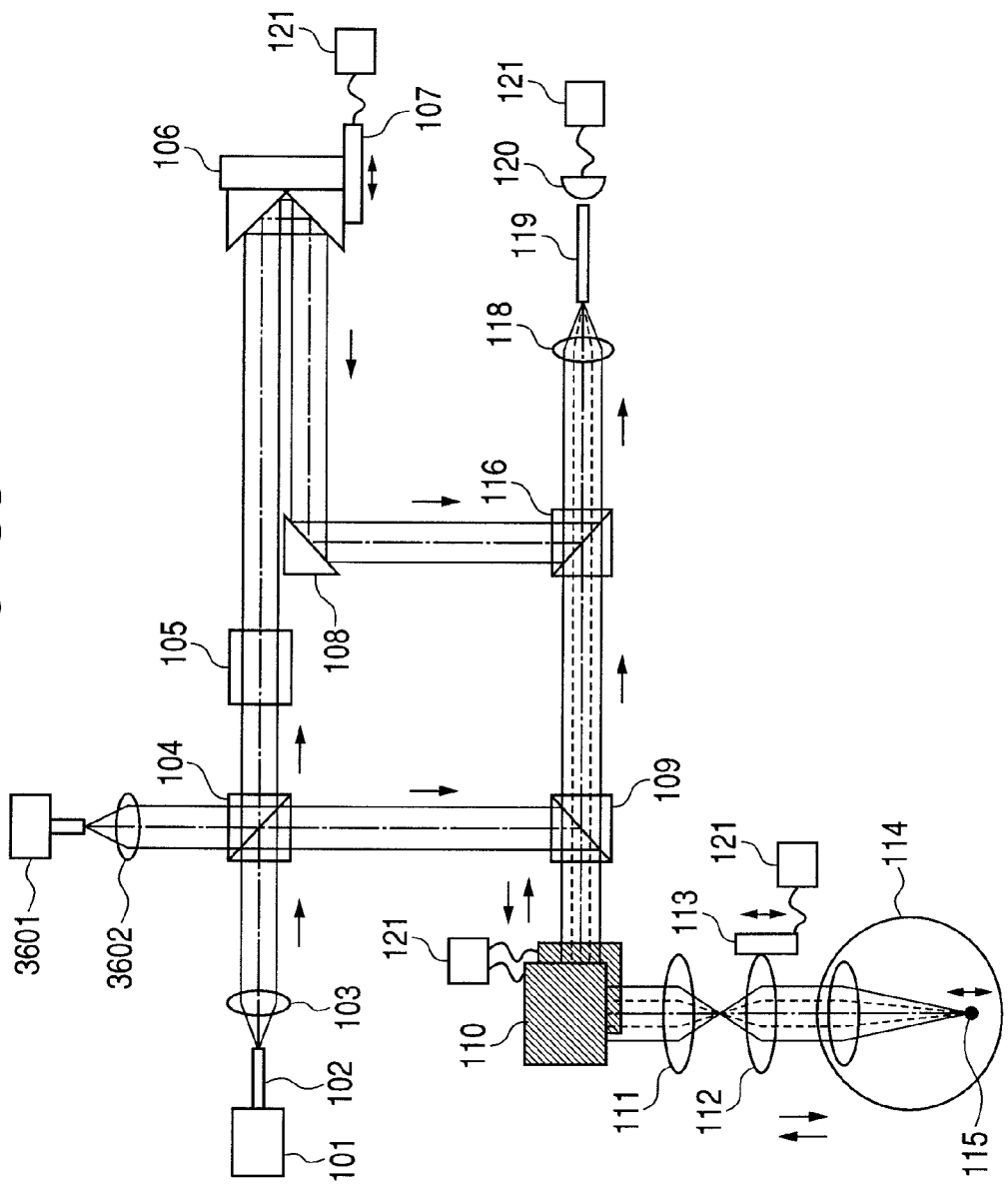
FIG. 36 is a schematic diagram illustrating construction of a light interference measuring apparatus in an eleventh example of the present invention.

Example 11 will be described with reference to FIG. 36. Here, this Example is a modified example of the first example, and it has construction of using the SS-OCT instead of the SD-OCT, and performing position correction. Since the TD-OCT and SS-OCT used different light sources, a wavelength scanning light source 3601 and a collimator 3602 for the SS-OCT were newly added. On the other hand, in the SS-OCT, since spectroscopy of an interference signal is not required unlike the SD-OCT, tomography information can be obtained by analyzing an irradiation wavelength and a detection signal by the wavelength scanning light source 3601. An interference signal can be obtained using the same photoelectric conversion detector 120 as that of the TD-OCT.

Here, in this Example, an example of performing TD-OCT and SS-OCT measurement in time sharing at high speed will be shown.

Light radiated from the light source 101 for the TD-OCT is optically guided similarly to the Example 1, and an interference signal is finally detected by the photoelectric conversion detector 120.

Figure 37:
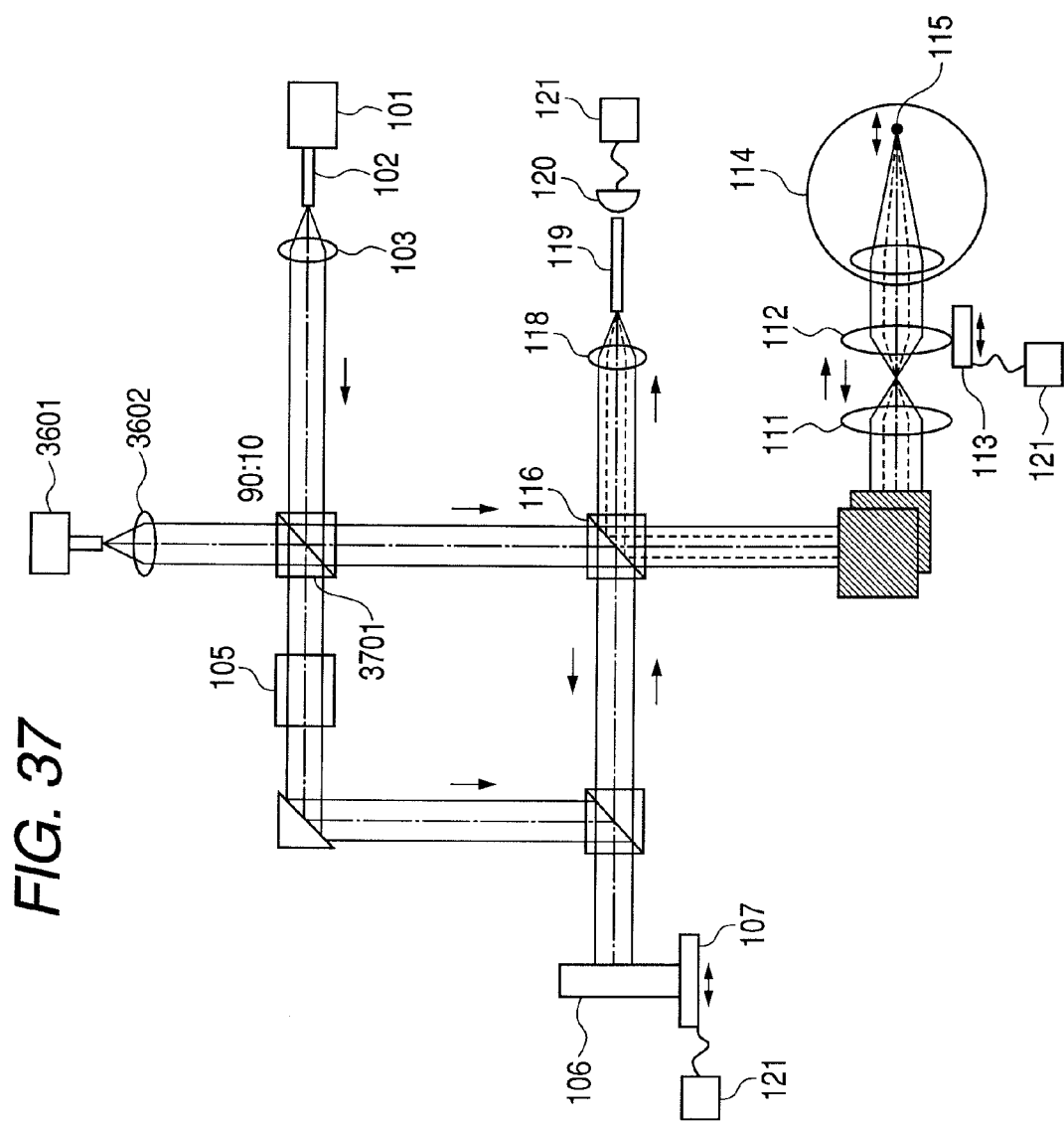
FIG. 37 is a schematic diagram illustrating another structural example in the eleventh example of the present invention.

On the other hand, light radiated from the wavelength scanning light source 3601 for SS-OCT is made into parallel light by the collimator 3602, and is divided into reference light and signal light by the division optical system 104. The reference light passes the frequency shifter 105, and is reflected by the optical delay unit 106 to be guided to the synthesis optical system 116 by the reflection mirror 108. Here, since signal strength fluctuates by a frequency shift similarly to the case of SD-OCT also in SS-OCT, it is also sufficient to stop a frequency shift in approximate synchronization with light irradiation, or to integrate a detection signal in an integral or half-integral multiple times. In addition, in order not to stop a frequency shift, construction as shown in FIG. 37 is also possible. FIG. 37 is based on the Michelson interferometer. The light radiated from the wavelength scanning light source 3601 hardly branches to a frequency shifter 105 side in an asymmetric division optical system 3701, but advances to the division optical system 116. On the other hand, many pass the frequency shifter 105 and the reference light of the light radiated from the light source 101 of TD-OCT follows the same path as that in the Example 1.

After the signal light which branches from the division optical system 104 or the asymmetric division optical system 3701 is guided to an eye 114 similarly to the path of TD-OCT, it is guided to the synthesis optical system 116. Then, the reference light and signal light are synthesized, and a part of coherent light with the synthetic amplitude added as a complex amplitude impinges on the condensing optical system 118. Then, it is optically coupled to a single-mode optical fiber 119, a component which coincides with a mode of the fiber is selected to propagate inside the fiber, and impinges on a photoelectric conversion detector 120. Furthermore, it is converted into an electric signal and is transmitted to an OCT processing apparatus 121*d*. Here, tomography information is obtained using the interference signal obtained and the light source scanning signal obtained in synchronization. A multiple image of TD-OCT is corrected using the SS-OCT information obtained in this way. In addition, by performing pupil division like that in the last Example, a deep depth of focus can be also obtained at the time of SS-OCT measurement.

Figure 38:
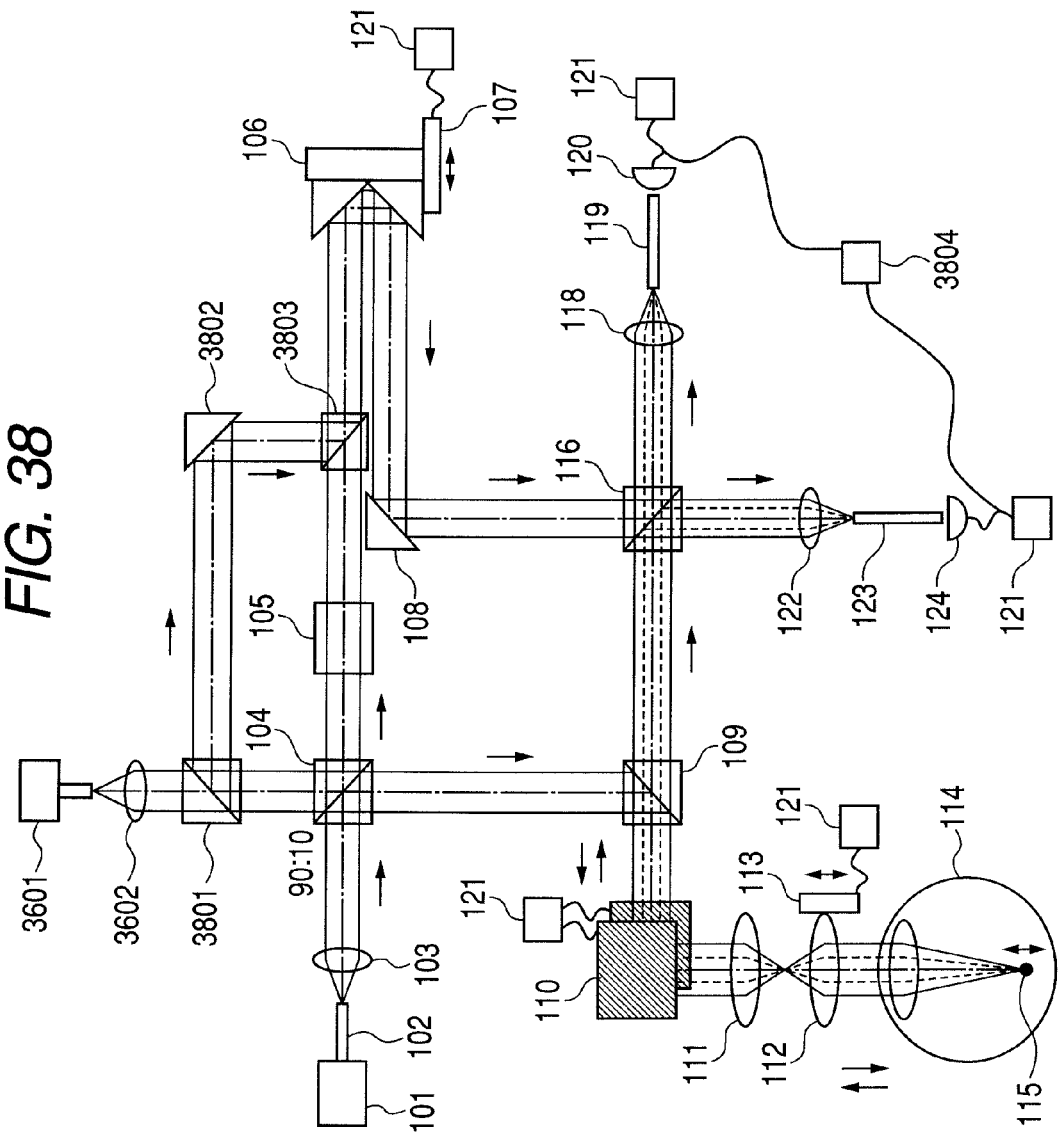
FIG. 38 is a schematic diagram illustrating a further structural example in the eleventh example of the present invention.

Furthermore, another Example of correction by SS-OCT will be described with reference to FIG. 38. In FIG. 38, light of SS-OCT is guided to a division optical system 3801 from the wavelength scanning light source 3601 and collimator 3602. Here, light branches to reference light and signal light, reference light is optically guided to the division optical system 104, and the reference light is optically guided to a mirror 3802. The signal light is further divided into signal light 3802 optically guided to the division optical system 109, and second reference light, which goes to the frequency shifter 105, in the division optical system 104. The reference light which does not receive a frequency shift, and the second reference light which is given a frequency shift are synthesized by a synthesis optical system 3803, and advances the same reference light path as that of TD-OCT. In this way, although there are a component, which receives a frequency shift, and a component, which does not receive it, in the reference light, what does not pass the frequency shifter 105 is stronger as signal strength. Furthermore, when making a transmission-to-reflection ratio of the division optical system 104 asymmetric, such as 90:10, for example, an influence of a frequency shift can be further reduced. A subsequent path is the same as that of TD-OCT, and passes the eye 114, and the signal light and reference light are synthesized by the synthesis optical system 116 and impinge on the photoelectric conversion detectors 120 and 124. On the other hand, the light radiated from the light source 101 for TD-OCT is optically guided by the division optical system 104 similarly to that in the Example 1, the signal light is optically guided to the division optical system 109, and the reference light is optically guided to the frequency shifter 105. Similarly to that in the Example 1, the signal light and reference light which are divided impinge on the synthesis optical system 116 through the eye 114 or mirror 106, are synthesized and are detected by the photoelectric conversion detectors 120 and 124.

An interference signal of TD-OCT and an interference signal of SS-OCT impinge on the photoelectric conversion detectors 120 and 124 similarly. Here, the signal detected by the photoelectric conversion detectors 120 and 124 can be divided by letting it pass a frequency filter 3804 by making a signal frequency of TD-OCT and a signal frequency of SS-OCT into different frequencies. A signal frequency of TD-OCT is frequency shift quantity of the reference light, and a signal frequency of SS-OCT is determined by a sweep period and purity of the wavelength of the wavelength scanning light source 3601. A corrected tomography image can be obtained from interference signals of respective TD-OCT and SS-OCT which are divided.

Example 12

No presence of SD Detection System in TD Signal Path

Figure 39:
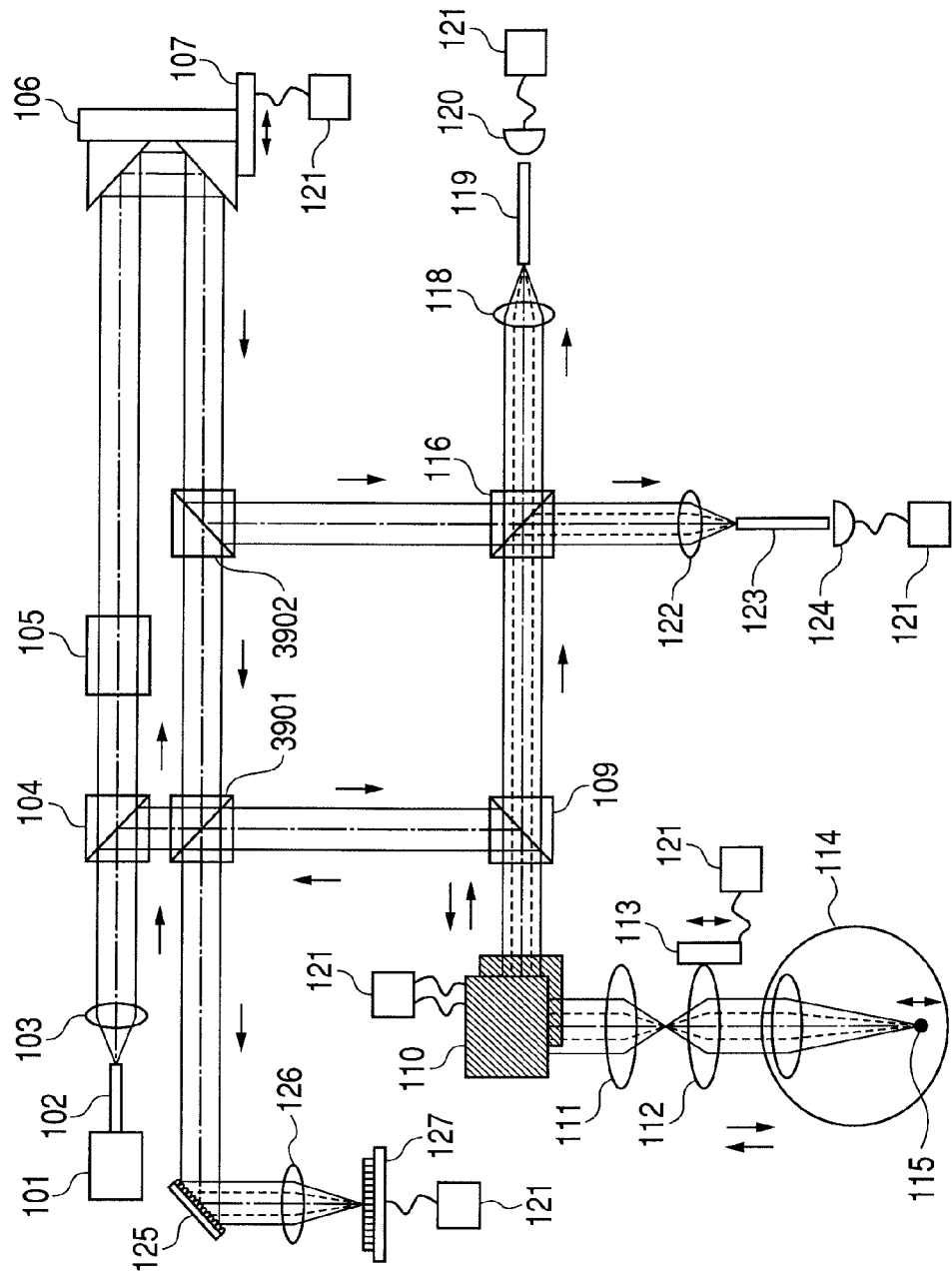
FIG. 39 is a schematic diagram illustrating construction of a light interference measuring apparatus in a twelfth example of the present invention.

Example 12 will be described with reference to FIG. 39. In order to enhance image quality of TD-OCT, it is advantageous to cause light to directly impinge on a photoelectric conversion detector without any optical component interposed in an optical path from an eye to the detector.

The Example 12 is a modified example of the Example 2, an SD-OCT detection system for position correction is equipped in another position. It includes branch optical systems 3901 and 3902.

First, light emitted from a light source 101 is optically guided by a single-mode optical fiber 102, and the light emitted from a fiber edge is converted into parallel light by a collimator lens 103 to be divided into reference light and signal light by a division optical system 104.

The signal light passes the branch optical system 3901, and is optically guided to an eye similarly to TD-OCT. The signal light returned from the eye is guided to the light guiding division optical system 109, and branches to signal light of TD-OCT which goes to the synthesis optical system 116, and signal light of SD-OCT which goes to the branch optical system 3901.

The reference light is reflected by the optical delay unit 106 after its optical frequency is shifted by Δf by the frequency shifter 105, and is guided to the synthesis optical system 116 by the reflection mirror 108. Here, a position of the optical delay unit 106 is controlled by a position driving unit 107 so that an optical path may become a predetermined length.

The reference light from the optical delay unit 106 is branched by the branch optical system 3902 into a path of the reference light of TD-OCT, and the reference light of SD-OCT which goes to the branch optical system 3901. The reference light of TD-OCT is synthesized by the synthesis optical system 116 with the signal light, heterodyne detection is performed similarly to the Example 2, and image information is obtained.

On the other hand, the signal light and reference light of SD-OCT are synthesized by the branch optical system 3901. An interference signal synthesized here impinges on the spectroscopic diffraction grating 125, condenses by the wavelength division imaging lens 126, and is given strength detection every wavelength by the line sensor 127. Tomography information is obtained from the detected spectral interference signal, and information on TD-OCT is corrected by a previous period correction method.

Other Examples

Figure 29:
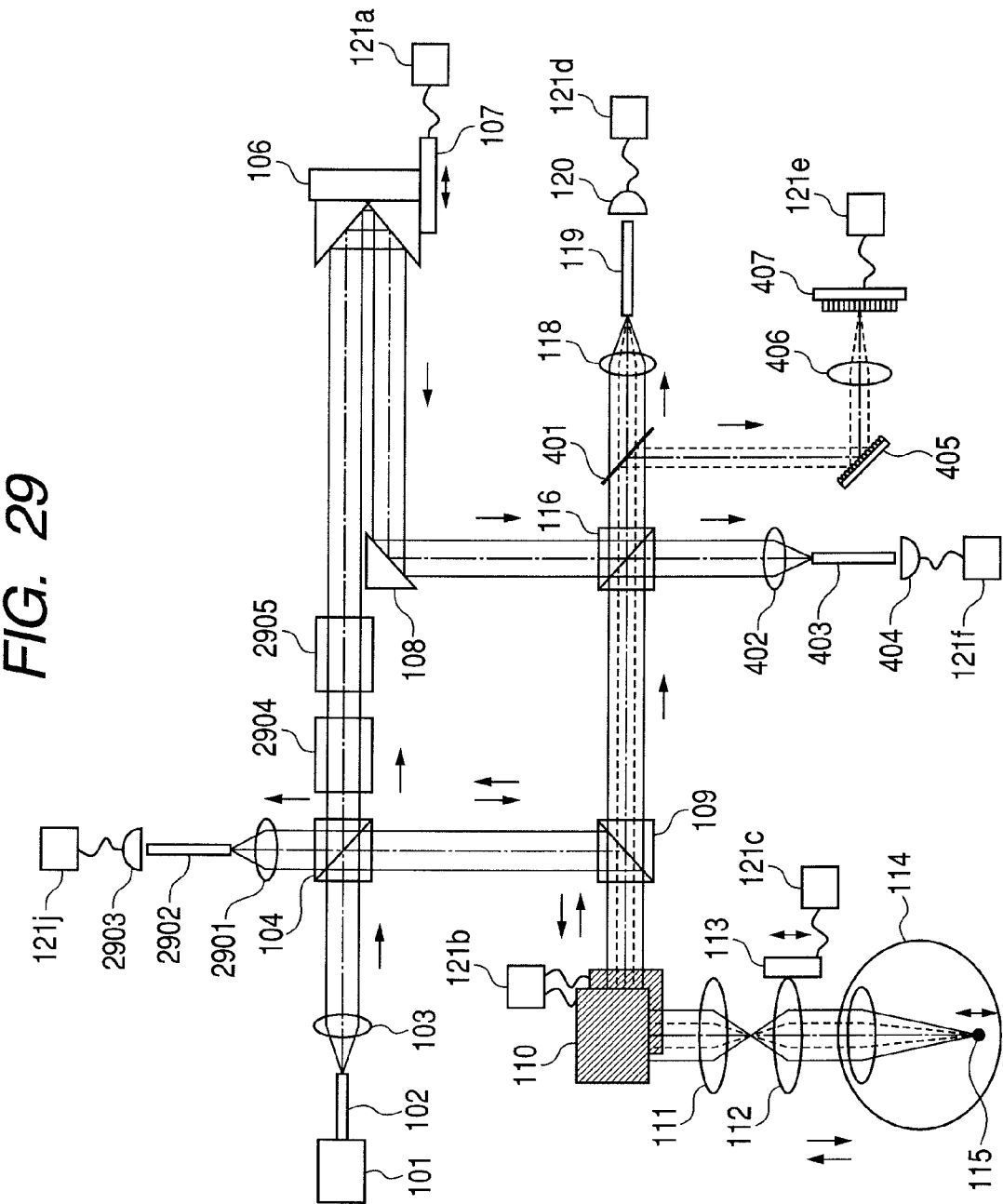
FIG. 29 is a schematic diagram illustrating construction of a light interference measuring apparatus in another example of the present invention.

Another Example will be described with reference to FIG. 29. The reflected light from the inspection object which is reflected by the light guiding division optical system 109 transmits the division optical system 104, and impinges on a condenser lens 2901. It impinges on a single-mode optical fiber 2902 by the condenser lens 2901, a light intensity signal is detected by a photoelectric conversion detector 2903, and it is transmitted to an OCT processing unit 121*j*.

Figure 30:
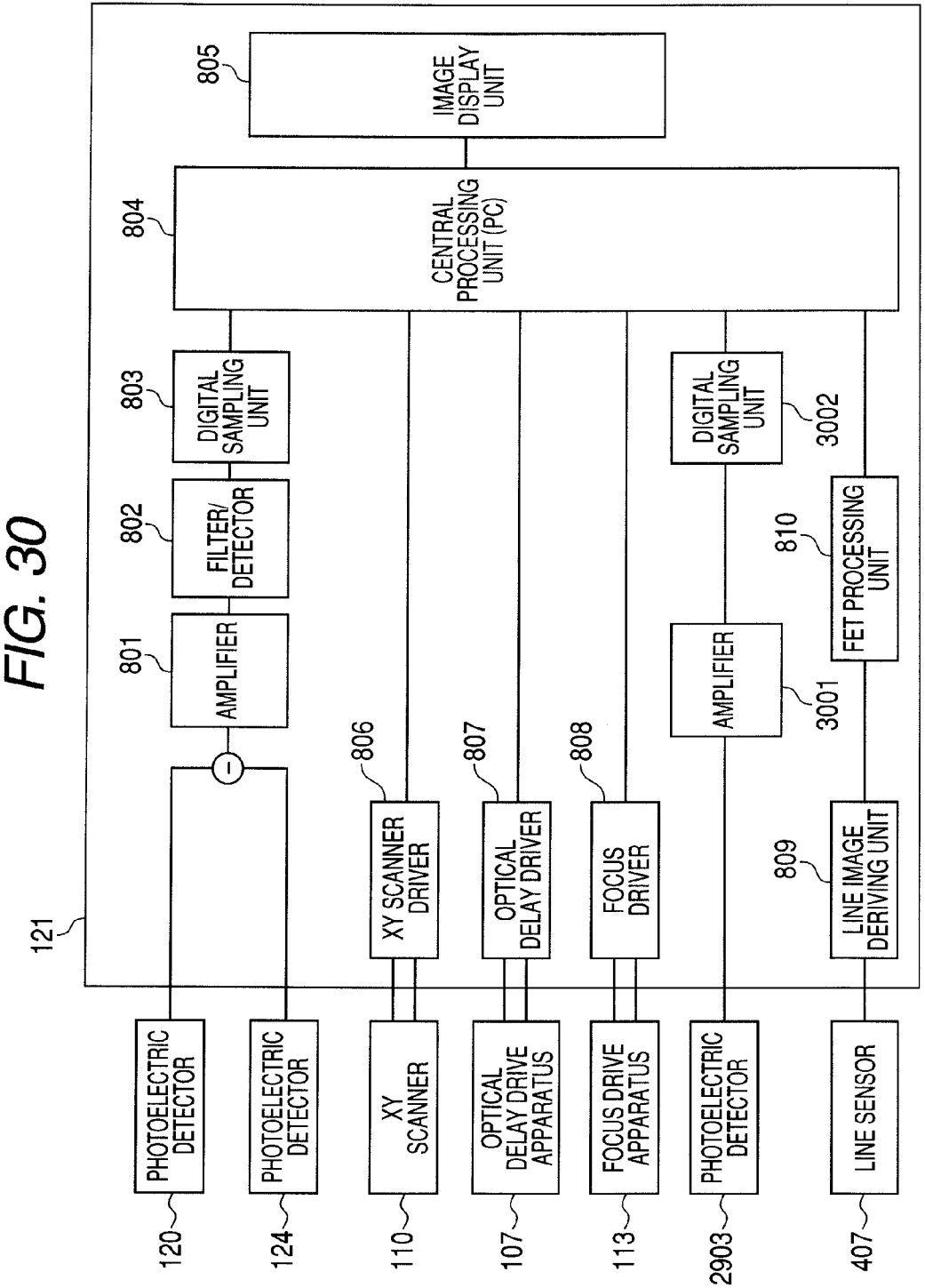
FIG. 30 is a schematic diagram illustrating functional blocks of an OCT processing unit in another example of the present invention.

Here, the OCT processing unit 121 which performs signal processing, control, and imaging of the optical interference detection system of this Example will be described with reference to FIG. 30. FIG. 30 illustrates schematically a functional block diagram of the OCT processing unit 121. An electric signal obtained from the photoelectric conversion detector 2903 is amplified by an amplifier 3001, and digitalization is performed in a digital sampling unit 3002. Then, a position in an inspection object can be determined by performing correspondence with the XY scanner driver 805 from this electric signal in a central process unit 804, and an SLO (Scanning Laser Ophtalmoscope) image can be obtained.

Figure 40:
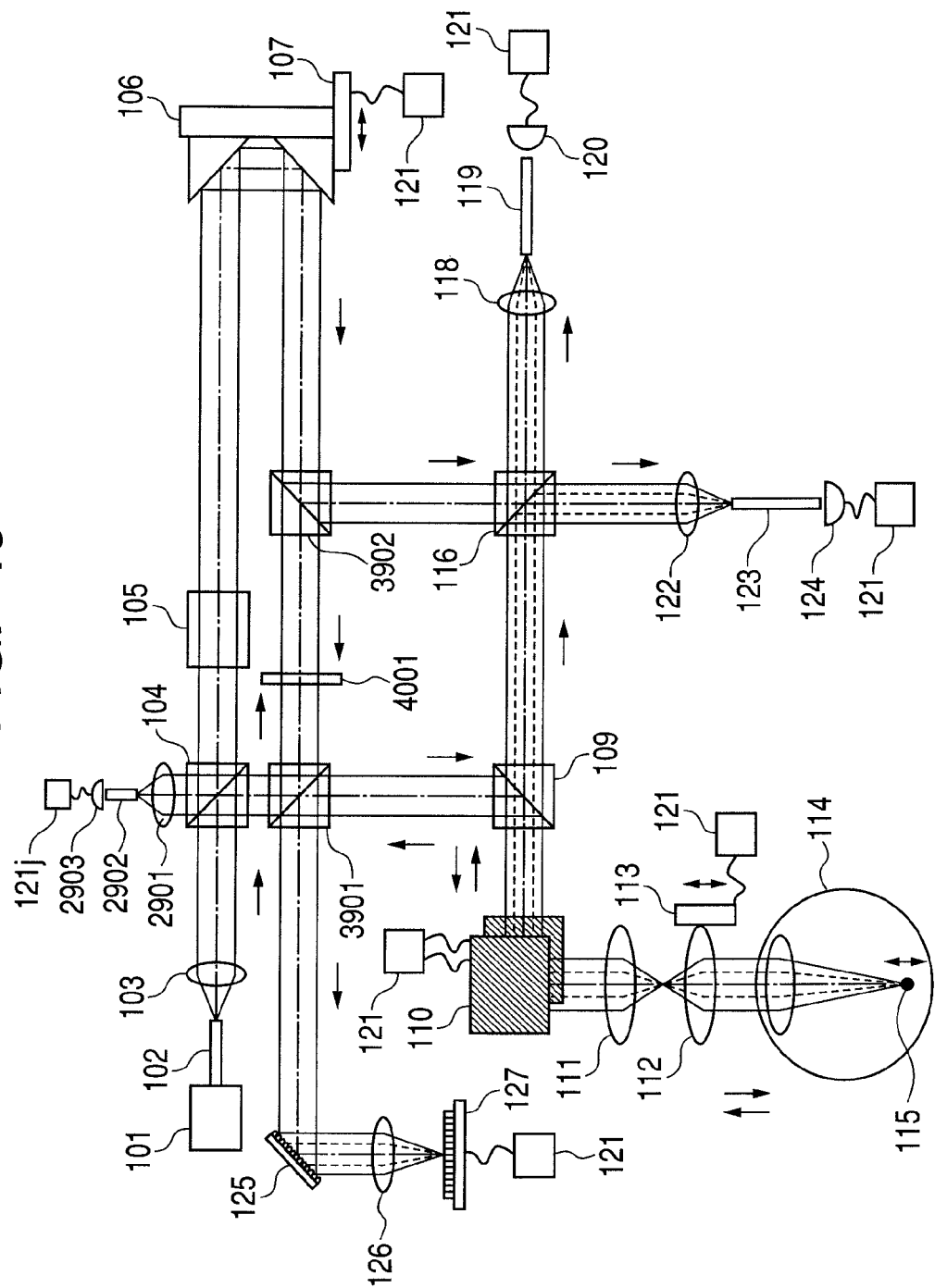
FIG. 40 is a schematic diagram illustrating a structural example including an SLO in the twelfth example of the present invention.

In addition, construction that a function of SLO is added to the construction of the Example 12 is illustrated in FIG. 40. Although it is the same as that of the Example 12 to include the branch optical systems 3901 and 3902, it is desirable not to enter in an SLO image acquisition system the reference light which passes the frequency shifter 105. Then, a switch 4001 is provided in a path of the reference light of SD-OCT. Shutting off the switch 4001 prevents reference light from impinging on the photoelectric transducer 2903 for SLO through the branch optical system 3901. Signal detection of SD-OCT and SLO image acquisition are switched, and what is necessary is just to make the switch 4001 turn on and off in synchronization with its timing.

Figure 41:
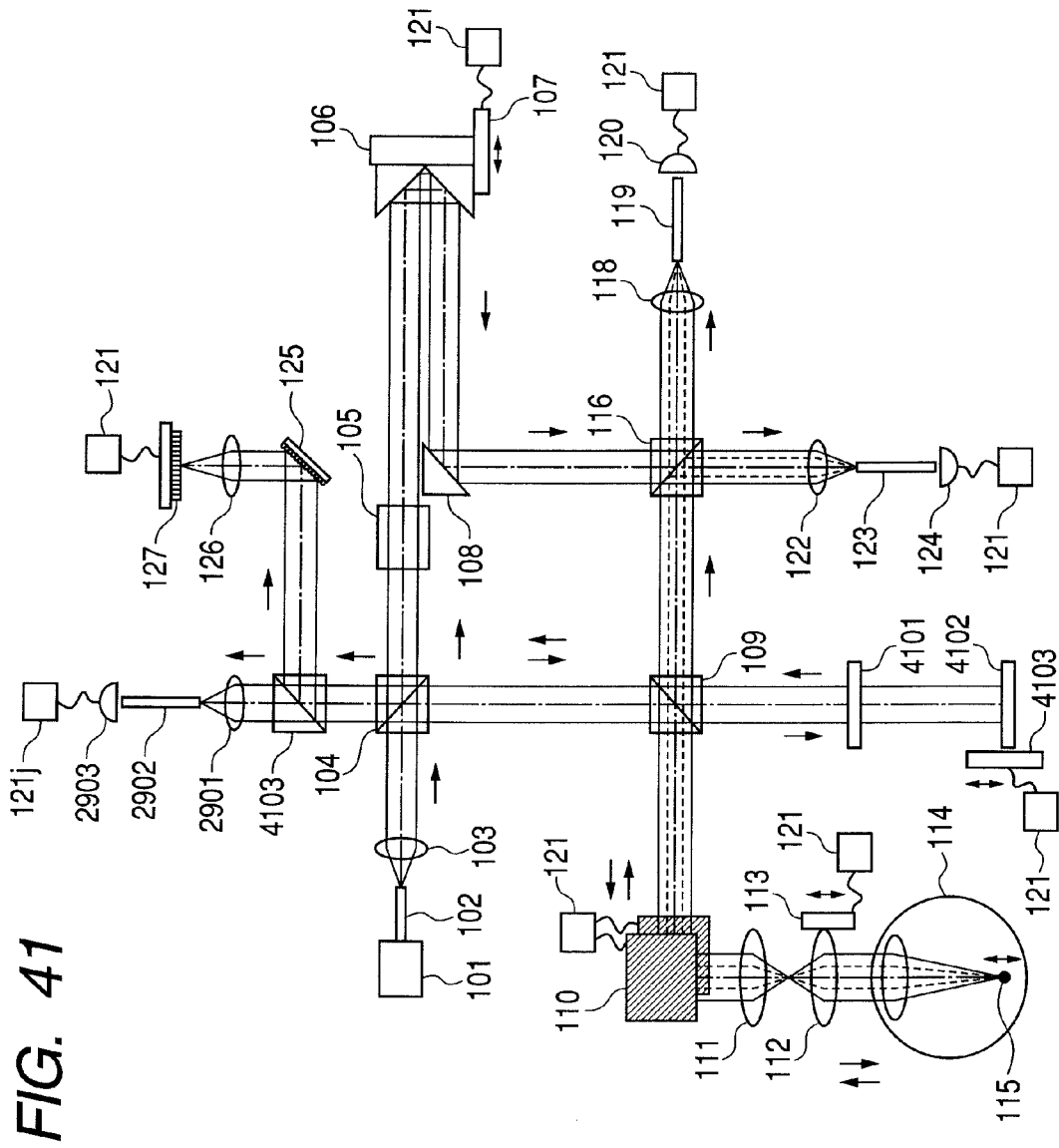
FIG. 41 is a schematic diagram of a combination example of SD-OCT and TD-OCT in the present invention.

Furthermore, another construction is illustrated in FIG. 41. This branches a path of the reference light of TD-OCT from a path of the reference light of SD-OCT. By branching the reference light, it does not arise that the reference light of SD-OCT is given a frequency shift, and hence, special processing such as integration of a signal and a stop of a frequency shifter becomes unnecessary.

The signal light incident on the light guiding division optical system 109 from the branch optical system 104 is branched into reference light for SD-OCT which advances to the switch 4101, and the original signal light which goes to the light beam scanning optical system 110. The signal light which goes to the light beam scanning optical system 110 impinges on an eye, and is optically guided again to the light guiding division optical system 109. On the other hand, the reference light of SD-OCT which goes to the switch 4101 is reflected by the mirror 4102 driven by the position drive apparatus 4103, and is optically guided by the light guiding division optical system 109. In the light guiding division optical system 109, the reference light and signal light are synthesized and are optically guided toward the branch optical system 104. The light which goes straight to the branch optical system 104 is branched to the photoelectric conversion detector 2903 of SLO, and the spectroscope 125 of SD-OCT by the branch optical system 4103. When measuring SD-OCT, the switch 4101 is opened, and the switch is closed when measuring SLO.

On the other hand, the signal light of TD-OCT goes straight in the light guiding division optical system 109, and is synthesized with the reference light in the synthesis optical system 116 to become an interference signal, and signal detection is performed by the photoelectric conversion detectors 120 and 124, and image information is obtained.

By obtaining suitably information on TD-OCT, SD-OCT, and SLO, longitudinal and lateral position correction of image information of TD-OCT can be performed, and a higher quality image can be obtained.

In addition, another Example will be described with reference to FIG. 29. A construction of using two photoacoustic modulators as a frequency shifter was adopted. A 1-MHz frequency shift can be obtained by causing plus first order diffracted light, which is given a +41-MHz frequency shift by a photoacoustic modulator 2904 driven at 41 MHz, to impinge on a photoacoustic modulator 2905 which is driven at 40 MHz, and using this minus first order diffracted light. Thereby, a high frequency shift of a photoacoustic modulator can be adjusted to a lower frequency shift. Furthermore, the dependency of an angle of diffraction of diffracted light on a wavelength is cancelled, traveling directions of rays of light having respective wavelength components become parallel to each other, and even if they proceed, a spread among one another can be suppressed.

Figure 31:
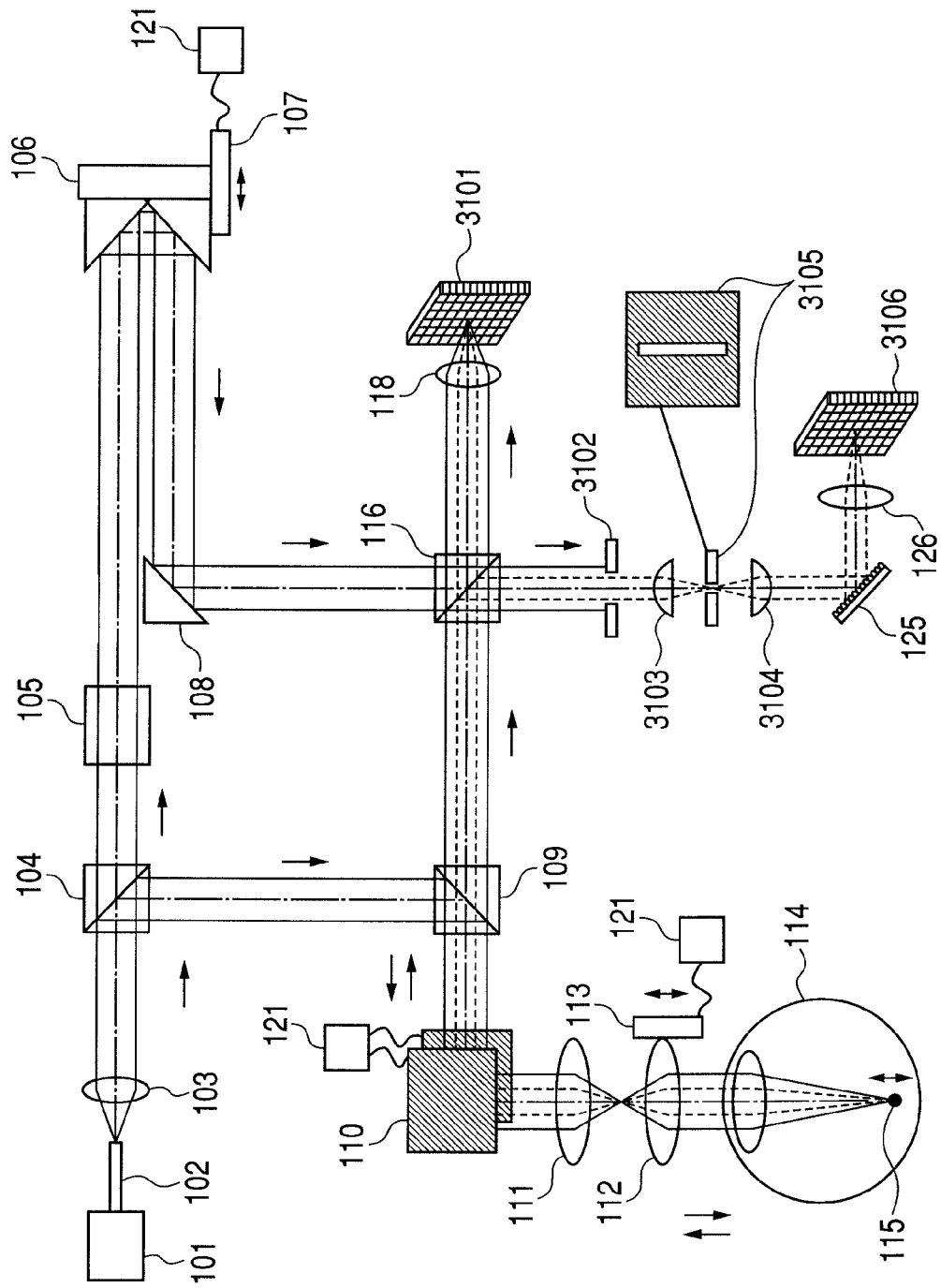
FIG. 31 is a schematic diagram illustrating construction of a light interference measuring apparatus in another example of the present invention.

Furthermore, another Example will be described with reference to FIG. 31. Also full field OCT which uses a high-order area sensor for a change of the confocal optical system and point sensor as a photodetection optical system for obtaining a TS-OCT image can be made. In this Example, a line condensing type SD-OCT using area sensors 3101 and 3106 which were a higher dimension of sensors to the construction of SD-OCT was used. Here, reference numerals 3103 and 3104 denote cylindrical lenses and reference numeral 3105 denotes a line slit.

In addition, in the Examples of the present invention, a sequence flow and the like can be modified variously in the range which does not deviate from the gist of the present invention.

The frequency shifter used in the above-mentioned Example is incorporable also into the construction in the case of obtaining a TS-OCT image.

In this case, since an output (light intensity vs wavelength) of a line sensor of SD-OCT may be fluctuated temporally (in the same form) in a period of a shift frequency (carrier frequency) of the frequency shifter, it is desirable to acquire it by performing integration in a time longer than the period of this fluctuation. Thus, a frequency shifter can also be used for device structure in the case of obtaining a SD-OCT image.

In addition, it is desirable that the shift frequency of a frequency shifter, that is, a carrier frequency is 1 to 10 MHz. In addition, it is satisfactory that sampling speed of a pixel of TS-OCT in the case that the carrier frequency is 1 to 10 MHz is several 100 kHz to several MHz.

In addition, when the image sampling of a TS-OCT image can be performed more quickly than that of an SD-OCT image, even if SD-OCT is not always performed to all the pixels of TS-OCT, SD-OCT can be performed only to a pixel necessary for alignment.

INDUSTRIAL APPLICABILITY

The high resolution OCT light interference measuring apparatus of the present invention can be used for various kinds of diagnostic systems and inspection apparatuses including somatoscopies, such as a fundus examination, a skin, and an endoscope, industrial quality control, etc.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-121745, filed May 2, 2007, and Japanese Patent Application No. 2008-066055, filed Mar. 14, 2008, which are hereby incorporated by reference herein in their entirety.

The invention claimed is:

1. An image forming method using optical coherence tomography comprising:
   acquiring first tomography image information of an object at a first focus position;

shifting a focus position along an optical axis of a signal light incident on the object from the first focus position into a second focus position different from the first focus position;

acquiring second tomography image information of the object at the second focus position, wherein the first tomography image information partially overlaps the second tomography image information in a direction of the optical axis; and correcting a positional gap between the first tomography image information and the second tomography image information based on tomography image information in a region in which the first tomography image information partially overlaps with the second tomography image information.

2. The image forming method according to claim 1, wherein the first tomography image information and the second tomography image information are acquired by Spectral Domain Optical coherence tomography.

3. The image forming method according to claim 1, further comprising:

acquiring first image information of the object in a direction crossing the optical axis at the first focus position;

acquiring second image information of the object in a direction crossing the optical axis at the second focus position; and correcting a positional gap between the first image information and the second image information based on the corrected position gap between the first tomography image information and the second tomography image information.

4. An optical coherence tomography apparatus that executes the image forming method according to claim 3, comprising:

a light source of a light incident in an object;

a first light dividing unit that divides the light from said light source into a signal light and a reference light; and a detecting unit that detects a coherent light between the reference light and the signal light.

5. The optical coherence tomography apparatus according to claim 4, further comprising:

a frequency shifter that forms a difference between a frequency of the signal light and a frequency of the reference light; and a control unit that controls said frequency shifter so as to shift the frequency of the signal light or the frequency of the reference light when acquiring first image information and second image information.

6. The optical coherence tomography apparatus according to claim 4, further comprising:

a light path conversion unit that converts a light path though which a coherent light passes; and a control unit that controls said light path conversion unit so that the coherent light passes through a light path for acquiring an image by Time Domain Optical coherence tomography when acquiring first image information or second image information, and that controls said light path conversion unit so that the coherent light passes through another light path for acquiring an image by Fourier Domain Optical coherence tomography when acquiring first tomography image information and second tomography image information.

7. The optical coherence tomography apparatus according to claim 4, further comprising:

a second light dividing unit that divides the coherent light into a light for acquiring an image by Time Domain Optical coherence tomography, and a light for acquiring an image by Spectral Domain Optical coherence tomography;

a spatial polarization converter that converts a polarization of light passing though said second light dividing unit; and a control unit that controls said spatial polarization converter so that the light for acquiring an image by Time Domain Optical coherence tomography is stronger than the light for acquiring an image by Spectral Domain Optical coherence tomography when acquiring first image information and second image information, and that controls said spatial polarization converter so that the light for acquiring an image by Spectral Domain Optical coherence tomography is stronger than the light for acquiring an image by Time Domain Optical coherence tomography when acquiring first image information and second image information.

8. The optical coherence tomography apparatus according to claim 4, further comprising:

a frequency shifter that forms a difference between a frequency of the signal light and a frequency of the reference light;

a second light dividing unit that divides the coherent light into a light for acquiring an image by Time Domain Optical coherence tomography, and a light for acquiring an image by Spectral Domain Optical coherence tomography;

a spatial polarization converter that converts a polarization of light passing though said second light dividing unit; and a control unit that controls said frequency shifter so as to shift the frequency of the reference light or the frequency of the signal light for acquiring the first and second image information, wherein said control unit controls said spatial polarization converter so that the light for acquiring an image by Time Domain Optical coherence tomography is stronger than the light for acquiring an image by Spectral Domain Optical coherence tomography when acquiring first image information and second image information, and wherein said control unit controls said spatial polarization converter so that the light for acquiring an image by Spectral Domain Optical coherence tomography is stronger than the light for acquiring an image by Time Domain Optical coherence tomography when acquiring first tomography image information and second tomography image information.

9. The optical coherence tomography apparatus according to claim 4, further comprising a light beam dividing unit for pupil division.

10. The optical coherence tomography apparatus according to claim 4, further comprising:

a frequency shifter that forms a difference between a frequency of the signal light and a frequency of the reference light, wherein said light source includes a first light source of a light having a plurality of center wavelengths, and a second light source of a light having a single center wavelength, wherein said frequency shifter is disposed on a light path of said second light source, and wherein a light path of said first light source is different from the light path of said second light source.

11. The image forming method according to claim 1, further comprising:

acquiring the positional gap in the direction of the optical axis based on a correlation between signal intensities of the first tomography image information and the second tomography image information in the region.

12. The image forming method according to claim 1, wherein the first tomography image information is acquired by Fourier Domain Optical coherence tomography, and the second tomography image information is acquired by the Fourier Domain Optical coherence tomography.

13. The image forming method according to claim 3, further comprising:

dividing a light from a light source into the signal light and a reference light; and scanning the object with the signal light in a direction crossing the optical axis, wherein the reference light interferes with the signal light reflected by or scattered by the object, and wherein the first image information and the second image information are acquired by Time Domain Optical coherence tomography.

14. The image forming method according to claim 3, wherein the first image information is acquired by Time Domain Optical coherence tomography as C-scan image of the object at the first focus position, and wherein the second image information is acquired by Time Domain Optical coherence tomography as C-scan image of the object at the second focus position.

15. An image forming method using optical coherence tomography comprising:

acquiring first tomography image information of an object at a first focus position by Fourier Domain Optical coherence tomography;

shifting a focus position along an optical axis of a signal light incident on the object from the first focus position into a second focus position different from the first focus position;

acquiring second tomography image information of the object at the second focus position by Fourier Domain Optical coherence tomography; and correcting a positional relation between the first tomography image information and the second tomography image information in a direction of the optical axis based on tomography image information in a region in which the first tomography image information partially overlaps with the second tomography image information.

16. The image forming method according to claim 15, wherein the first tomography image information and the second tomography image information are derived by Spectral Domain Optical coherence tomography.

17. An optical coherence tomography apparatus that executes the image forming method according to claim 15, comprising:

a light source of a light incident in an object;

a light dividing unit that divides the light from said light source into a signal light and a reference light; and a detecting unit that detects a coherent light between the reference light and the signal light.

18. An image forming method using optical coherence tomography comprising:

acquiring first image information of an object at a first focus position;

shifting a focus position from the first focus position into a second focus position different from the first focus position;

acquiring second image information of the object at the second focus position; and correcting a positional relation between the first image information and the second image information based on tomography image information in a region in which the first image information partially overlaps with the second image information.

19. The image forming method according to claim 18, further comprising:

acquiring tomography image information at a third focus position different from the first focus position and the second focus position by Fourier Domain Optical coherence tomography, wherein the tomography image information partially overlaps with the first image information and the second image information in a direction of an optical axis.

* * * * *